United States Patent [19]

Light et al.

[11] 4,439,354
[45] * Mar. 27, 1984

[54] TRICYCLIC ALCOHOLS, ETHERS AND ESTERS, PROCESS FOR PREPARING SAME AND USE THEREOF IN AUGMENTING OR ENHANCING THE ORGANOLEPTIC PROPERITES OF CONSUMABLE MATERIALS

[75] Inventors: Kenneth K. Light, N. Ogden, Utah; Joseph A. McGhie, Montclair, N.J.; Futoshi Fujioka, Wanamassa, N.J.; Takao Yoshida, West Long Branch, N.J.

[73] Assignee: International Flavors & Fragrances Inc., New York, N.Y.

[*] Notice: The portion of the term of this patent subsequent to Oct. 25, 2000 has been disclaimed.

[21] Appl. No.: 311,291

[22] Filed: Oct. 13, 1981

Related U.S. Application Data

[62] Division of Ser. No. 206,649, Nov. 13, 1980.

[51] Int. Cl.³ .......................................... C07C 49/453
[52] U.S. Cl. .............................. 252/522 R; 560/256; 568/665; 568/817
[58] Field of Search .................... 252/522 R; 560/256; 568/665, 817

[56] References Cited

U.S. PATENT DOCUMENTS

| | | | |
|---|---|---|---|
| 3,879,466 | 4/1975 | Light | 568/374 |
| 3,925,486 | 12/1975 | Greuter et al. | 252/522 R |
| 4,250,338 | 2/1981 | Sprecker et al. | 252/522 R |
| 4,275,251 | 6/1981 | Sprecker et al. | 252/522 R |
| 4,311,852 | 1/1982 | Skorianetz et al. | 252/522 R |

*Primary Examiner*—John F. Niebling
*Attorney, Agent, or Firm*—Arthur L. Liberman

[57] ABSTRACT

Described are compounds having the generic structure:

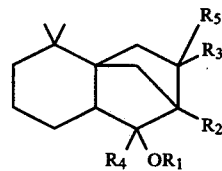

wherein $R_1$ represents hydrogen, methyl or acetyl and wherein $R_2$, $R_3$, $R_4$ and $R_5$ represent the same or different hydrogen, methyl or ethyl; a process for preparing same using compounds designed according to the generic structure:

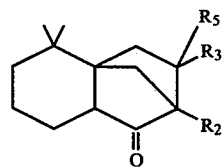

and organoleptic uses thereof in perfumes, colognes and perfumed articles.

14 Claims, 70 Drawing Figures

NMR SPECTRUM FOR EXAMPLE I.

IR SPECTRUM FOR EXAMPLE I.

GLC PROFILE FOR EXAMPLE III.

NMR SPECTRUM FOR EXAMPLE IV.

IR SPECTRUM FOR EXAMPLE V.

GLC PROFILE FOR EXAMPLE V.

IR SPECTRUM FOR EXAMPLE IV.

NMR SPECTRUM FOR EXAMPLE V.

NMR SPECTRUM FOR EXAMPLE VII.

NMR SPECTRUM FOR EXAMPLE VII, FRACTION 16 $^{13}C$.

NMR SPECTRUM FOR EXAMPLE VI.

IR SPECTRUM FOR EXAMPLE VI.

GLC PROFILE FOR EXAMPLE X(a).

NMR SPECTRUM FOR EXAMPLE VIII.

IR SPECTRUM FOR EXAMPLE VIII.

MASS SPECTRUM FOR EXAMPLE X(a).

NMR SPECTRUM FOR EXAMPLE X(a) FRACTION 5.

IR SPECTRUM FOR FRACTION 5 OF EXAMPLE X(a).

NMR SPECTRUM FOR EXAMPLE X(b).

MASS SPECTRUM FOR FRACTION 2 OF EXAMPLE X(c).

NMR SPECTRUM FOR FRACTION 2 OF EXAMPLE X(c).

IR SPECTRUM FOR FRACTION 2 OF EXAMPLE X(c).

GLC PROFILE
EXAMPLE XI A

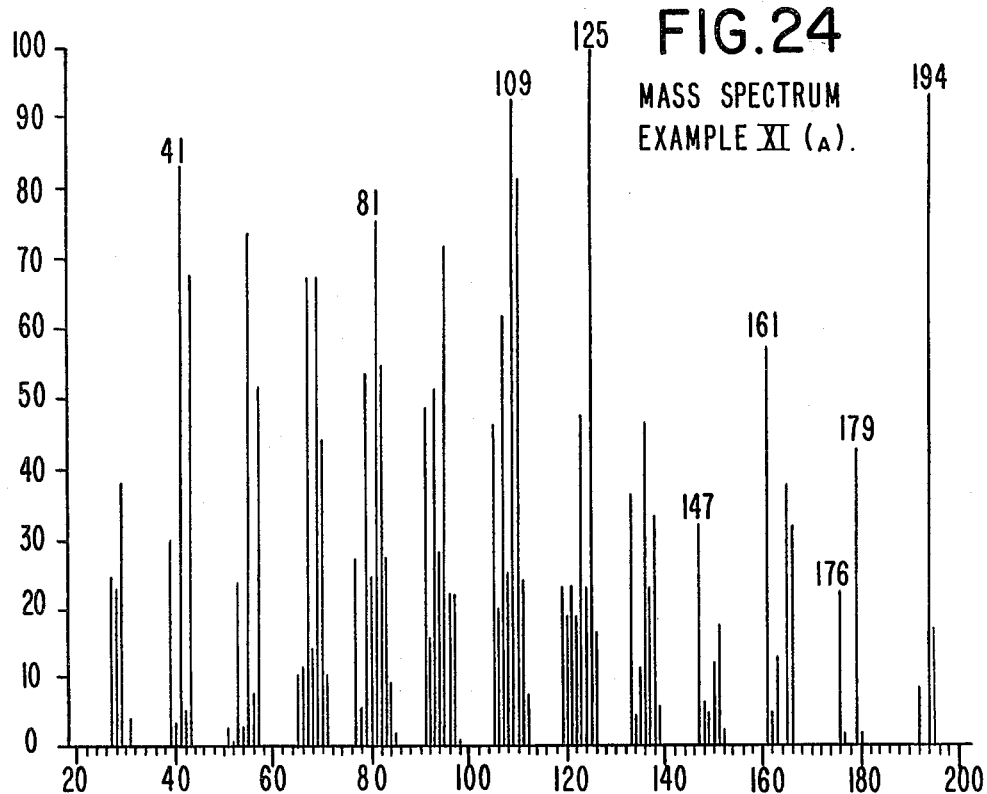
FIG. 24 MASS SPECTRUM EXAMPLE XI (A).
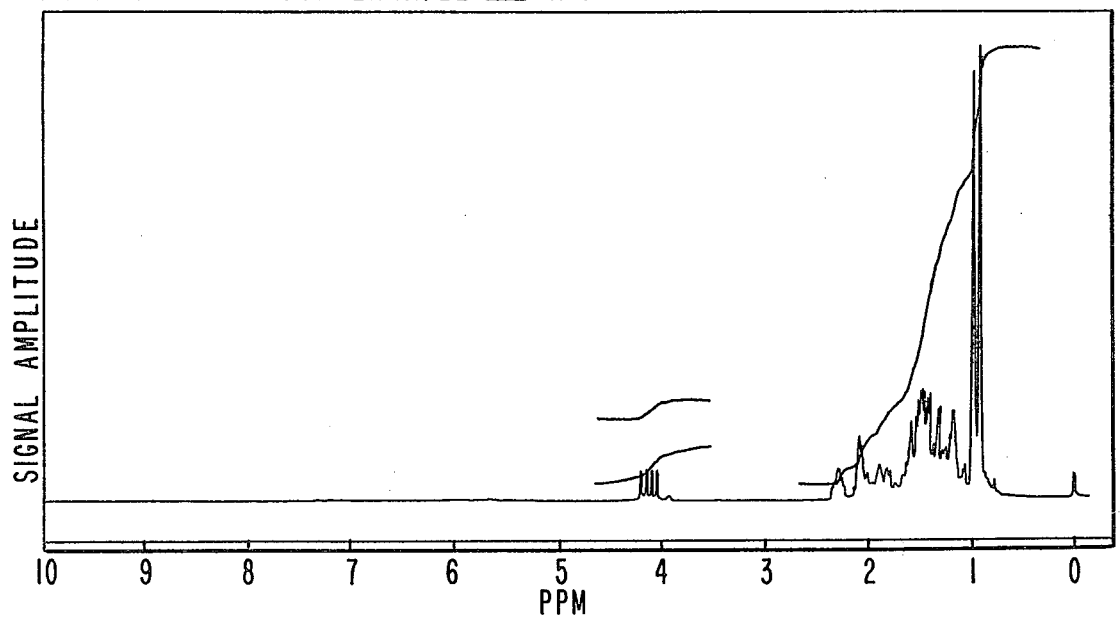
FIG. 25
NMR SPECTRUM FOR EXAMPLE XI A.

GLC PROFILE FOR EXAMPLE XI (B).

MASS SPECTRUM FOR EXAMPLE XI (B).

NMR SPECTRUM FOR EXAMPLE XI(B), BULKED FRACTIONS 1 & 2.

IR SPECTRUM FOR EXAMPLE XI B, (BULKED FRACTIONS 1 & 2).

MASS SPECTRUM FOR EXAMPLE XI(C).

NMR SPECTRUM FOR FRACTION 3 OF EXAMPLE XI(C).

IR SPECTRUM FOR FRACTION 3 OF EXAMPLE XI(C).

MASS SPECTRUM FOR EXAMPLE XII(A).

NMR SPECTRUM FOR FRACTION 3 OF EXAMPLE XIIA

IR SPECTRUM FOR FRACTION 3 OF EXAMPLE XII A.

MASS SPECTRUM FOR EXAMPLE XII B.

NMR SPECTRUM FOR FRACTION 2 OF EX. XII B.

IR SPECTRUM FOR FRACTION 2 OF EXAMPLE XII B.

MASS SPECTRUM FOR EXAMPLE XIII (A)

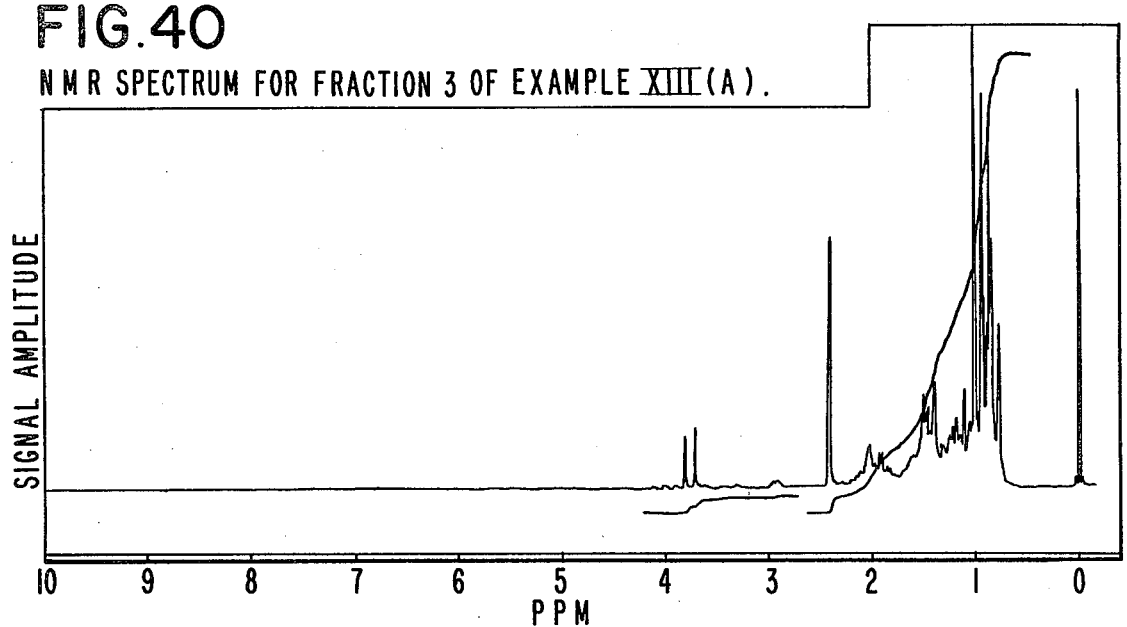
FIG.40 NMR SPECTRUM FOR FRACTION 3 OF EXAMPLE XIII(A).
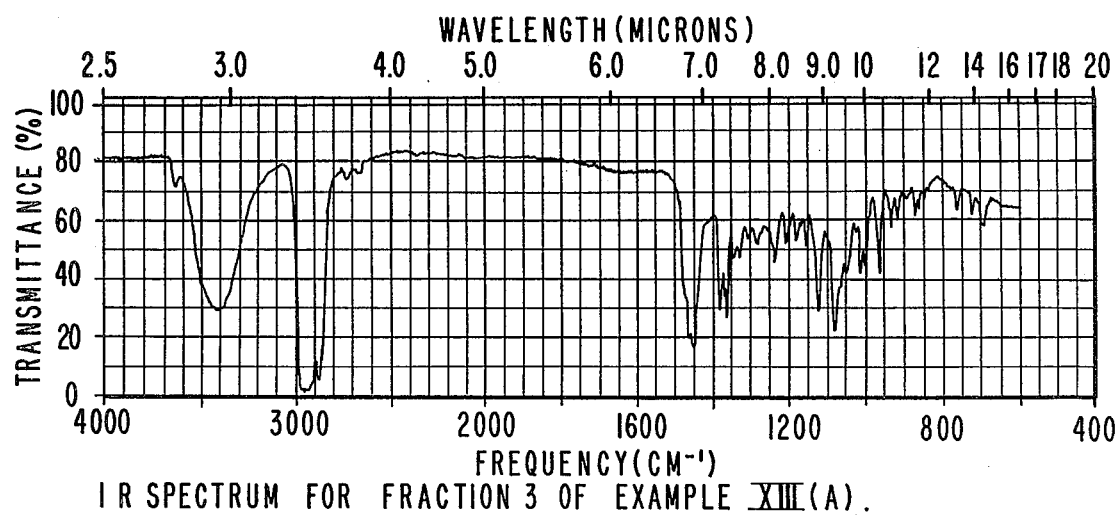
FIG.41
IR SPECTRUM FOR FRACTION 3 OF EXAMPLE XIII(A).

NMR SPECTRUM FOR FRACTION 3 OF EXAMPLE XIII B.

IR SPECTRUM FOR FRACTION 3 OF EXAMPLE XIII B.

EXAMPLE XIV (A)
MASS SPECTRUM

NMR SPECTRUM FOR FRACTION 4 OF EXAMPLE XIV (A).

IR SPECTRUM FOR FRACTION 4 OF EXAMPLE XIV (A)

EXAMPLE XIV (B)
MASS SPECTRUM

NMR SPECTRUM FOR FRACTION 4 OF EXAMPLE XIV B.

IR SPECTRUM FOR FRACTION 4 OF EXAMPLE X

GLC PROFILE
EXAMPLE XV(A)

MASS SPECTRUM
EXAMPLE XV(A)

NMR SPECTRUM FOR FRACTION I OF EXAMPLE XV(A).

IR SPECTRUM FOR FRACTION I OF EXAMPLE XV(A).

MASS SPECTRUM EXAMPLE XV(B)

NMR SPECTRUM FOR FRACTION 2 OF EXAMPLE XV(B).

IR SPECTRUM FOR FRACTION 2 OF EXAMPLE XV (B)

GLC PROFILE FOR EXAMPLE XV(C)

MASS SPECTRUM FOR FRACTION 2 OF EXAMPLE XV(C).

NMR SPECTRUM FOR FRACTION 2 OF EXAMPLE XV(C).

IR SPECTRUM FOR FRACTION 2 OF EXAMPLE XV(C).

GLC PROFILE FOR EXAMPLE XVI
(AFTER RUSHOVER DISTILLATION)

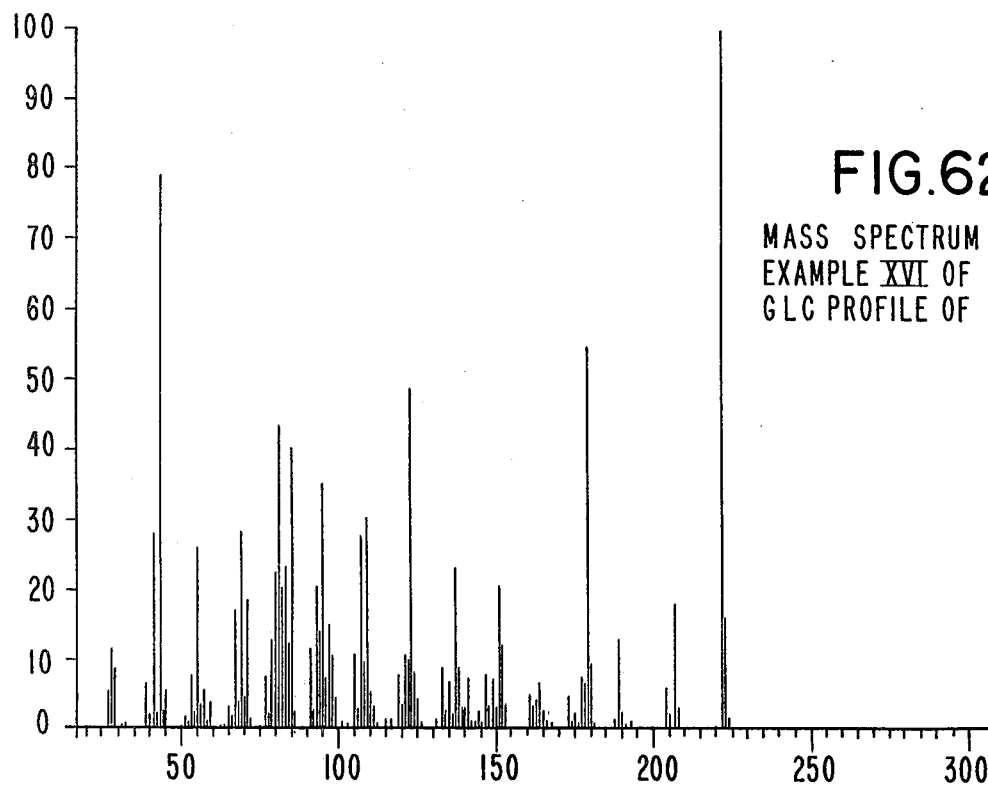
FIG. 62
MASS SPECTRUM FOR EXAMPLE XVI OF PEAK I OF GLC PROFILE OF FIG. 61.
FIG. 63
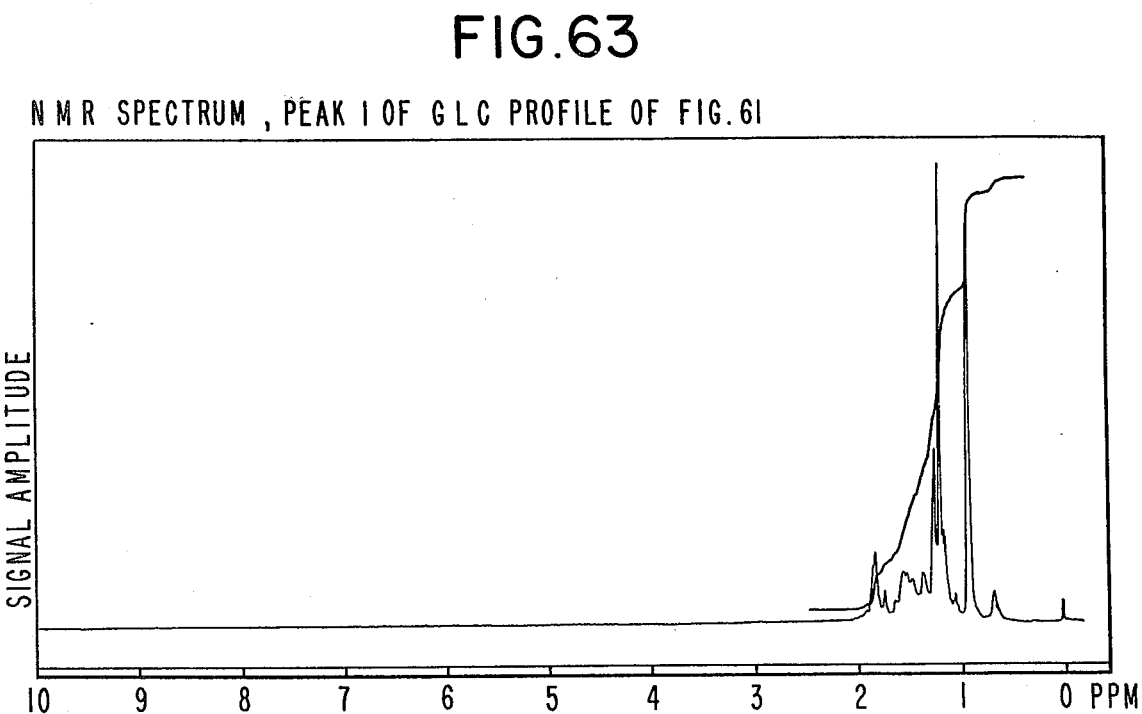
NMR SPECTRUM, PEAK I OF GLC PROFILE OF FIG. 61

NMR SPECTRUM, EXAMPLE XVI, PEAK 2 OF GLC PROFILE OF FIG. 61

IR SPECTRUM, EXAMPLE XVI, PEAK 2 OF GLC PROFILE OF FIG. 61.

NMR SPECTRUM FOR EXAMPLE XVI, PEAK 3 OF GLC PROFILE OF FIG. 61

IR SPECTRUM, EXAMPLE XVI, PEAK 3 OF GLC PROFILE OF FIG. 61.

NMR SPECTRUM FOR EXAMPLE XVI, PEAK 4 OF GLC PROFILE OF FIG. 61

NMR SPECTRUM EXAMPLE XVI, PEAK 5 OF GLC PROFILE OF FIG. 61

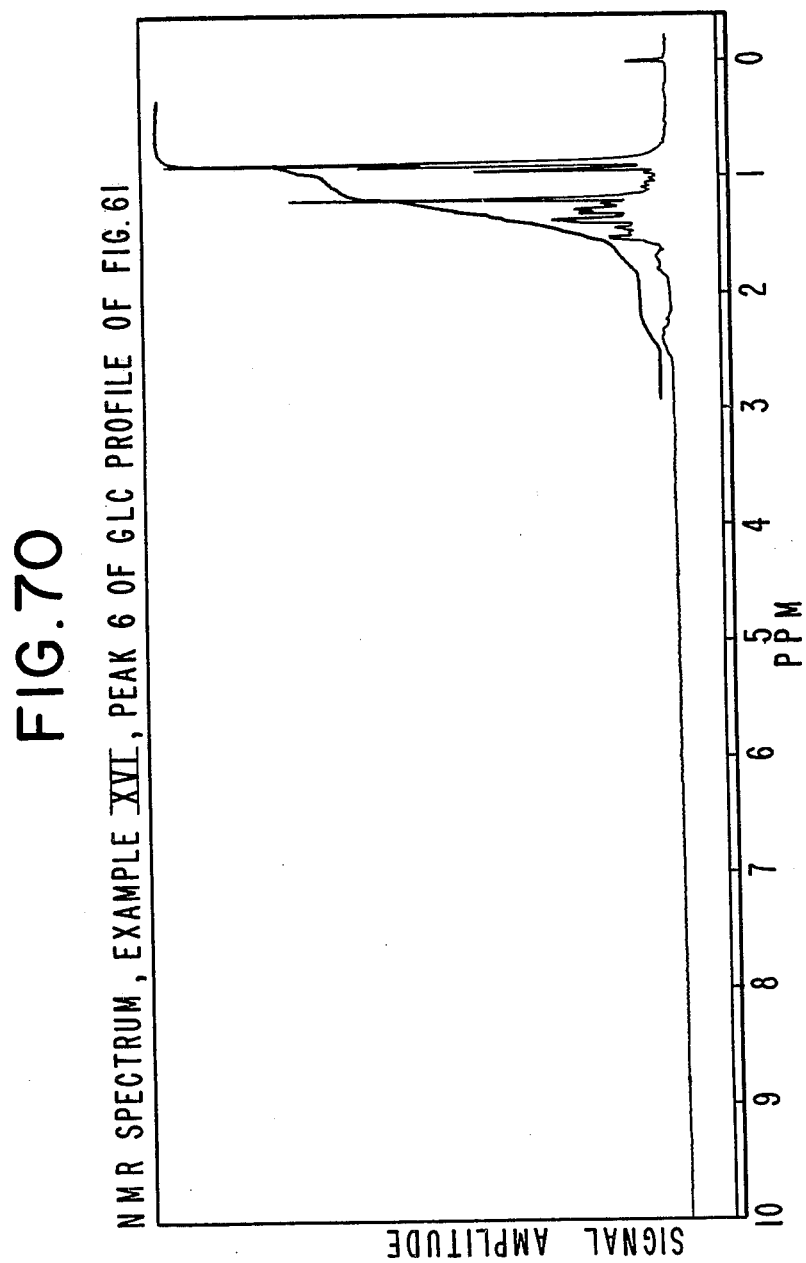

TRICYCLIC ALCOHOLS, ETHERS AND ESTERS, PROCESS FOR PREPARING SAME AND USE THEREOF IN AUGMENTING OR ENHANCING THE ORGANOLEPTIC PROPERITES OF CONSUMABLE MATERIALS

This is a divisional of application Ser. No. 206,649, filed Nov. 13, 1980.

BACKGROUND OF THE INVENTION

The present invention relates to compounds having the generic structure:

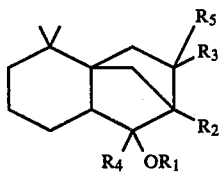

wherein $R_1$ represents hydrogen, ethyl or acetyl and wherein $R_2$, $R_3$, $R_4$ and $R_5$ represent the same or different hydrogen, methyl or ethyl and to uses thereof in augmenting or enhancing the organoleptic properties of consumable materials.

Materials which can provide dry woody (cedary, vetiver, thymol-like, camphoraceous, amber, sandalwood-like, fresh, sweaty, fruity, castoreum, cedrus atlantica-like, patchouli, labdanum-like, green, fruity, amber, cigar box-like, sandalwood-like, oriental, cedarwood-like, minty, spicy, floral (rose), vetiver-like, and grapefruit oil-like aromas with warm and rich aromas on dry-out are highly useful in the art of perfumery and are also known in the art of perfumery. Many of the natural materials which provide such fragrances and contribute desired nuances to the perfumery compositions are high in cost, vary in quality from one batch to another and/or are generally subject to the usual variations of natural products.

Materials which can provide oriental/incense-like, herbaceous, minty, earthy, tobacco-like, woody, and cedarwood-like aromas and tastes in foodstuffs, chewing tobaccos, smoking tobaccos and smoking tobacco articles are highly desirable in the manufacture of such materials. Such aroma nuances are known in the art of food flavoring, chewing tobacco flavoring, and smoking tobacco flavoring. Many of the natural materials which provide such aromas and tastes and contribute desired nuances to smoking tobaccos, chewing tobaccos and foodstuffs are high in cost, vary in quality from one batch to another and/or are generally subject to the usual variations of natural products.

There is, accordingly, a continuing effort to find synthetic materials which will replace the essential flavor and fragrance notes provided by natural essential oils or compositions thereof in consumable materials including foodstuffs, perfume compositions, perfumed articles, colognes, smoking tobaccos, chewing tobaccos and the like. Unfortunately, many of these synthetic materials either have the desired nuances only to a relatively small degree or else contribute undesirable or unwanted odor to the compositions. The search for materials which can particularly provide more refined patchouli, vetiver cedarwood and sandalwood and amber fragrances and oriental-like, natural tobacco-like and cedarwood aromas and tastes in tobaccos, particularly smoking tobaccos, has been difficult and relatively costly in the areas of both natural products and synthetic products.

Light et al. in U.S. Pat. No. 4,139,650 issued on Feb. 13, 1979 discloses compositions for altering the flavor and/or aroma of consumable products including foods, tobacco and perfumes utilizing as the essential ingredient at least one organic tricyclic alcohol having the formula:

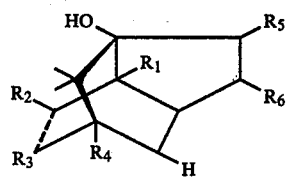

wherein each of $R_1$, $R_2$, $R_3$, $R_4$, $R_5$, and $R_6$ is selected from the group consisting of hydrogen and methyl; wherein the dashed line is a carbon-carbon single bond or a carbon-carbon double bond; and wherein when the dashed line is a carbon-carbon single bond, one of $R_2$ or $R_3$ is hydrogen.

The use in perfumery of the compound having the structure:

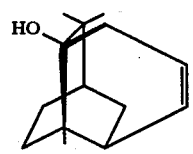

("norpatchoulinol") is disclosed in the following patents:

1. Belgium No. 788,301 issued Mar. 1, 1973
2. German Offenlegungschrift No. 2,242,913 published Mar. 8, 1973
3. Dutch published application No. 72/11760 published Mar. 5, 1973

A product of the reduction of this compound is also disclosed ("dihydro norpatchoulinol"). This product has the structure:

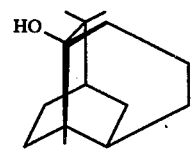

The compounds of our invention have properties considered to be unobvious, unexpected and advantageous with respect to the properties of the above-mentioned prior art compounds.

Nothing set forth in either of U.S. Pat. No. 3,907,908 or U.S. Pat. No. 4,139,650 discloses the processes or the compounds or the uses of the instant invention.

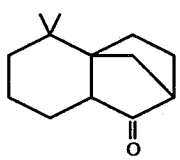

produced according to Example I.

Figure 2:
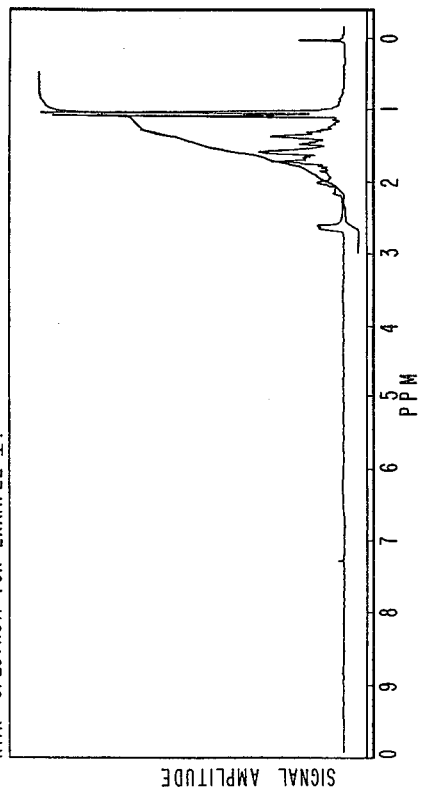

FIG. 2 represents the infra-red spectrum for the tricyclic ketone compound having the structure:

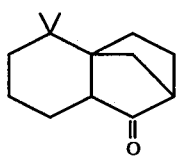

prepared according to Example I.

Figure 3:
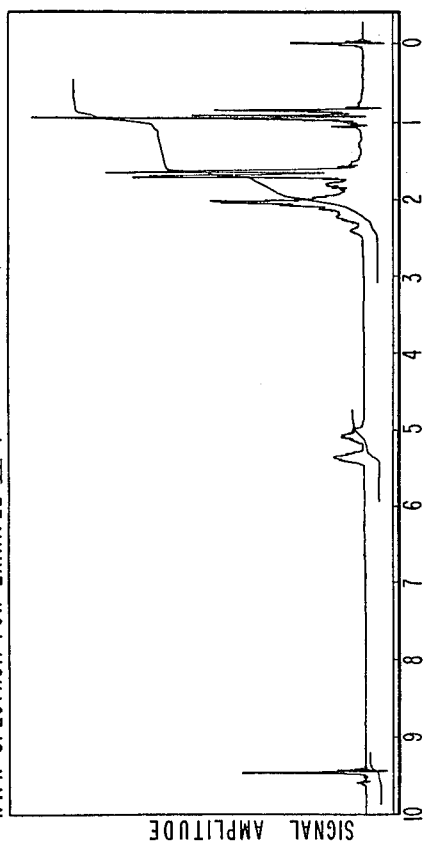

FIG. 3 represents the GLC profile for the reaction product of Example III.

Figure 4:
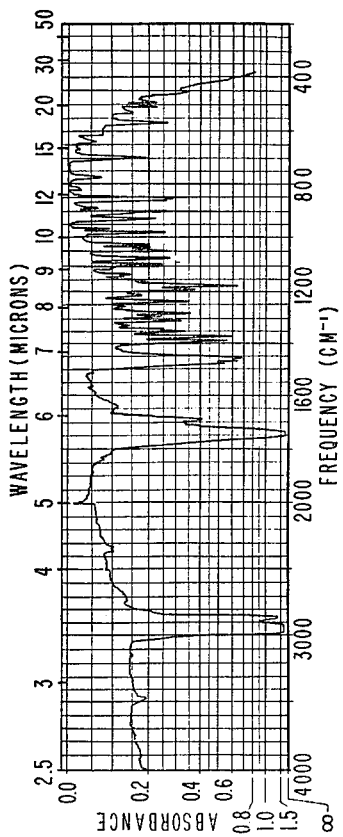

FIG. 4 represents the NMR spectrum for the aldehyde produced according to Example IV, having the structure:

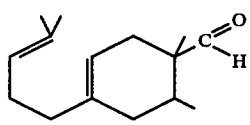

Figure 5:
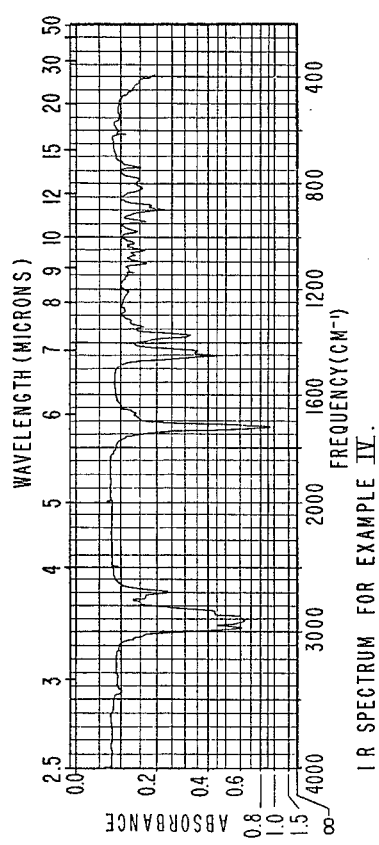

FIG. 5 represents the infra-red spectrum for the aldehyde having the structure:

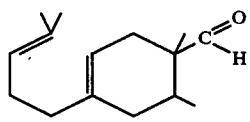

produced according to Example IV.

Figure 6:
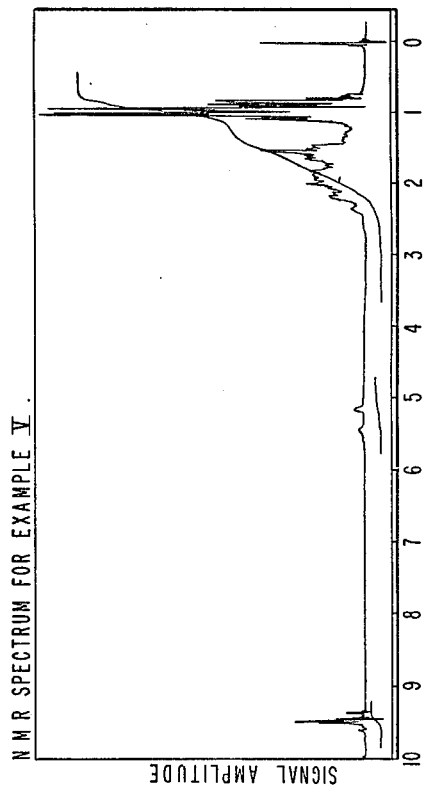

FIG. 6 represents the NMR spectrum for the mixture of aldehydes produced according to Example V, having the generic structure:

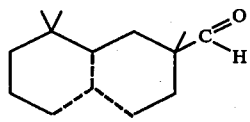

Figure 7:
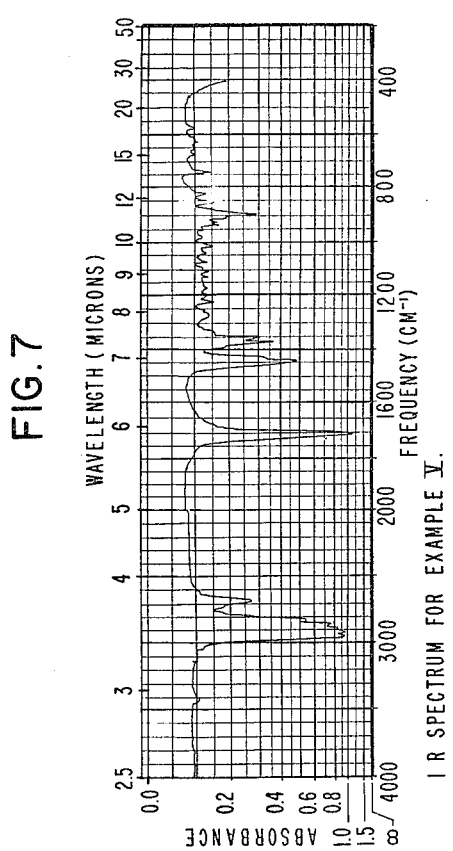

FIG. 7 represents the infra-red spectrum for the mixture of aldehydes produced according to Example V, having the generic structure:

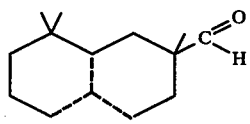

wherein one of the dashed lines represents a carbon-carbon double bond and the other of the dashed lines represents carbon-carbon single bonds.

Figure 8:
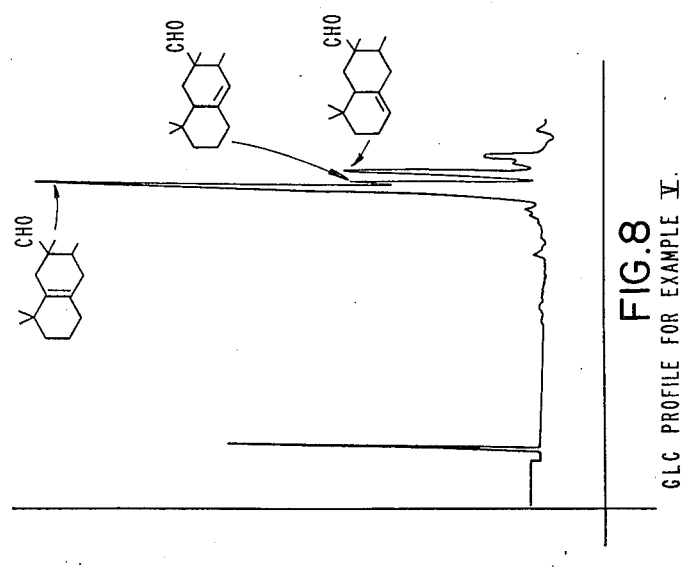

FIG. 8 represents the GLC profile for the product produced according to Example V, containing the aldehydes having the generic structure:

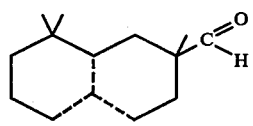

Figure 9:
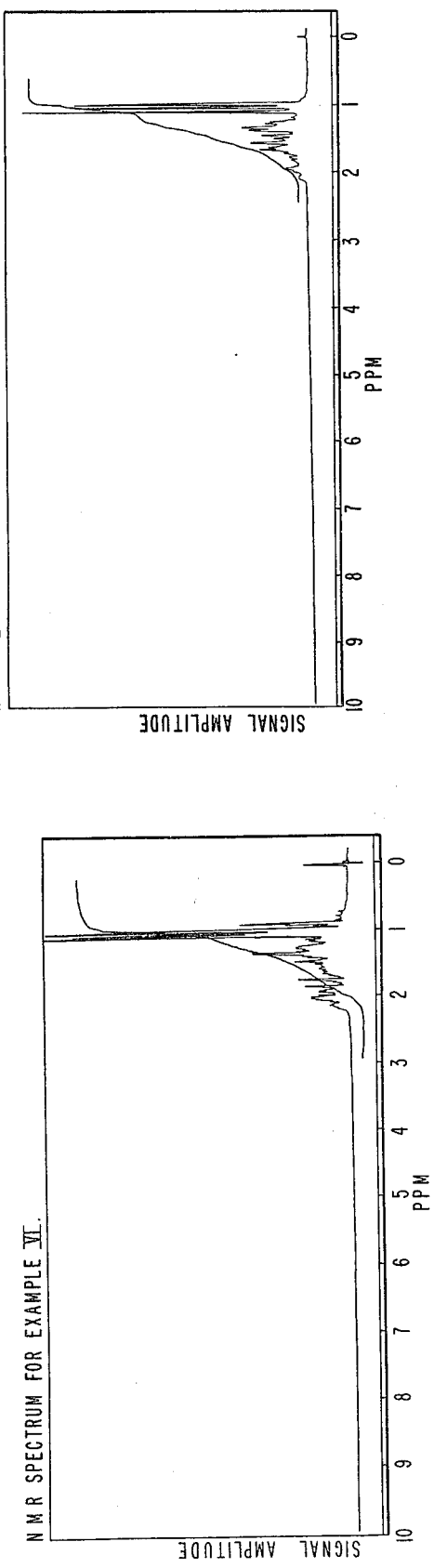

FIG. 9 represents the NMR spectrum for the tricyclic ketone having the structure:

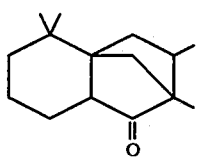

produced according to Example VI.

Figure 10:
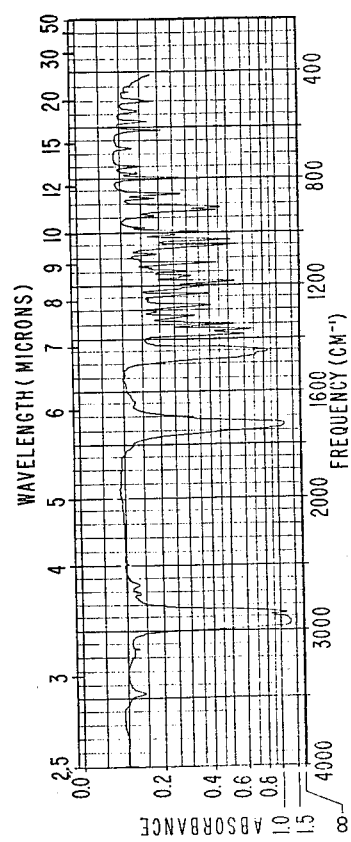

FIG. 10 represents the infra-red spectrum for the tricyclic ketone having the structure:

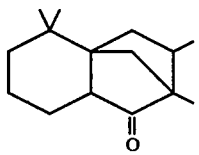

produced according to Example VI.

Figure 11:
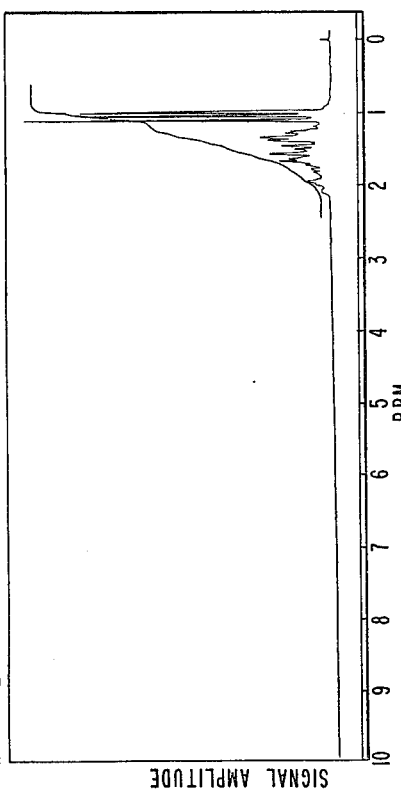

FIG. 11 represents the NMR spectrum for the tricyclic ketone produced according to Example VII, having the structure:

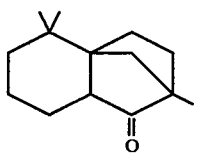

Figure 12:
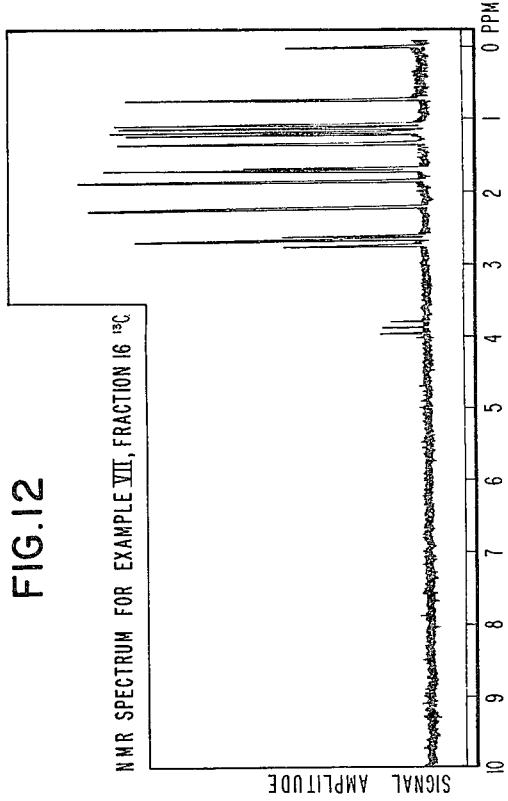

FIG. 12 represents the $^{13}C$ NMR spectrum for the tricyclic ketone having the structure:

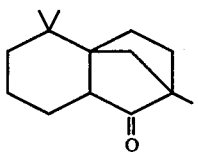

produced according to Example VII.

Figure 13:
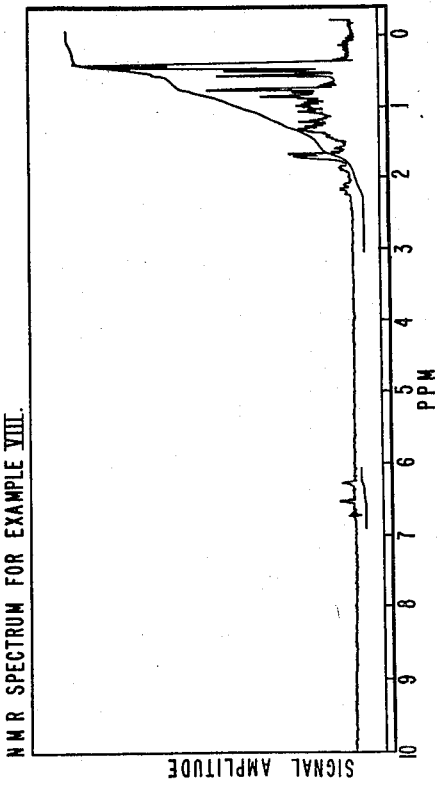

FIG. 13 represents the NMR spectrum for the tricyclic ketone having the structure:

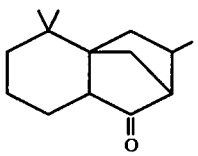

produced according to Example VIII.

Figure 14:
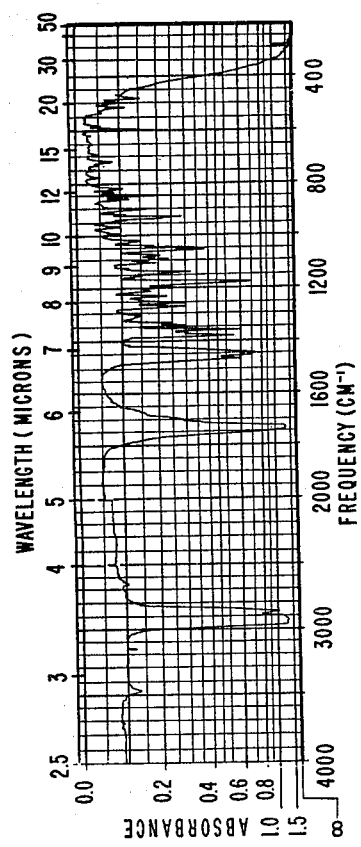

FIG. 14 represents the infra-red spectrum for the tricyclic ketone having the structure:

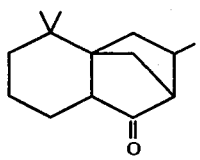

produced according to Example VIII.

Figure 15:
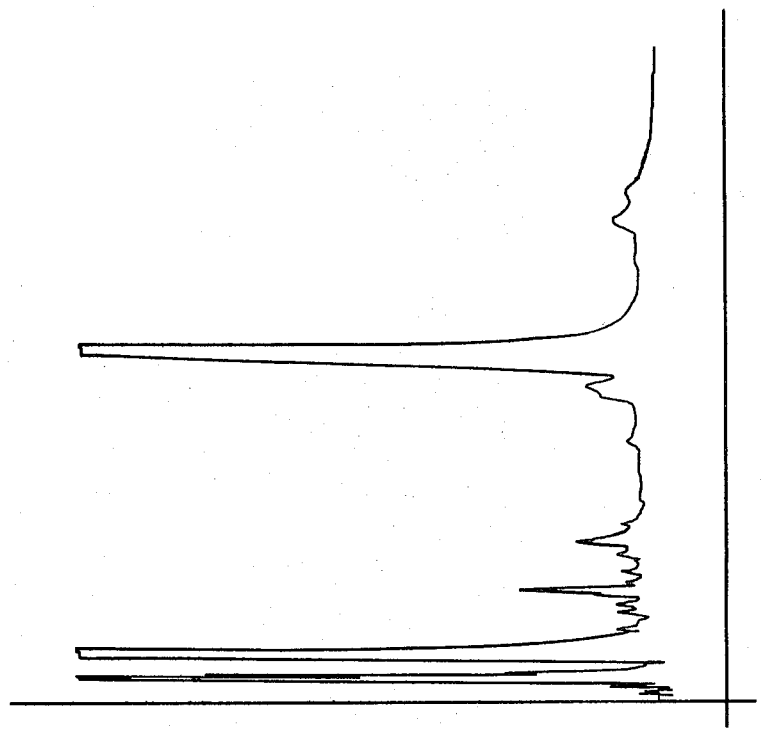

FIG. 15 represents the GLC profile for the reaction product of Example X(A) containing the compound having the structure:

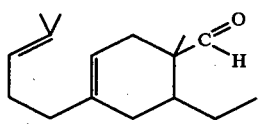

Figure 16:
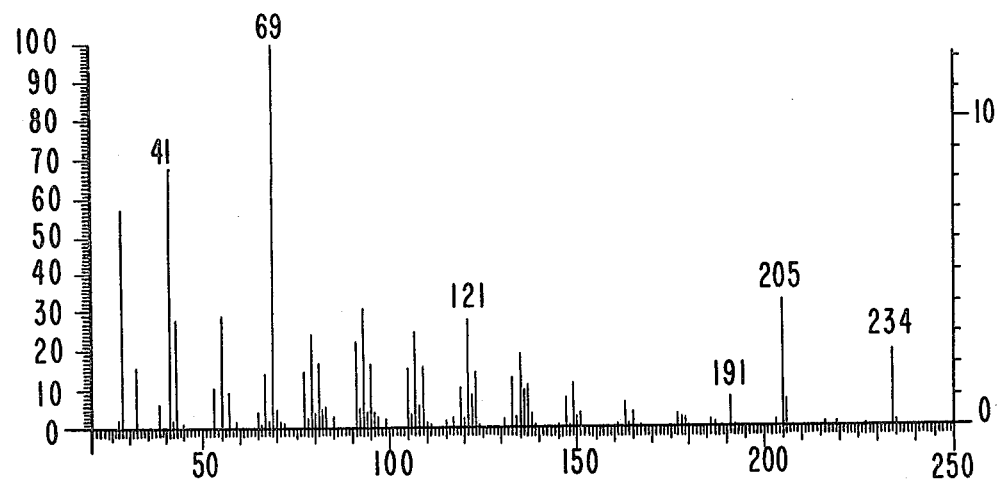

FIG. 16 is the mass spectrum for the compound having the structure:

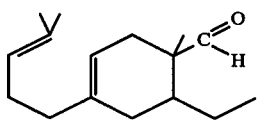

produced according to Example X(A).

Figure 17:
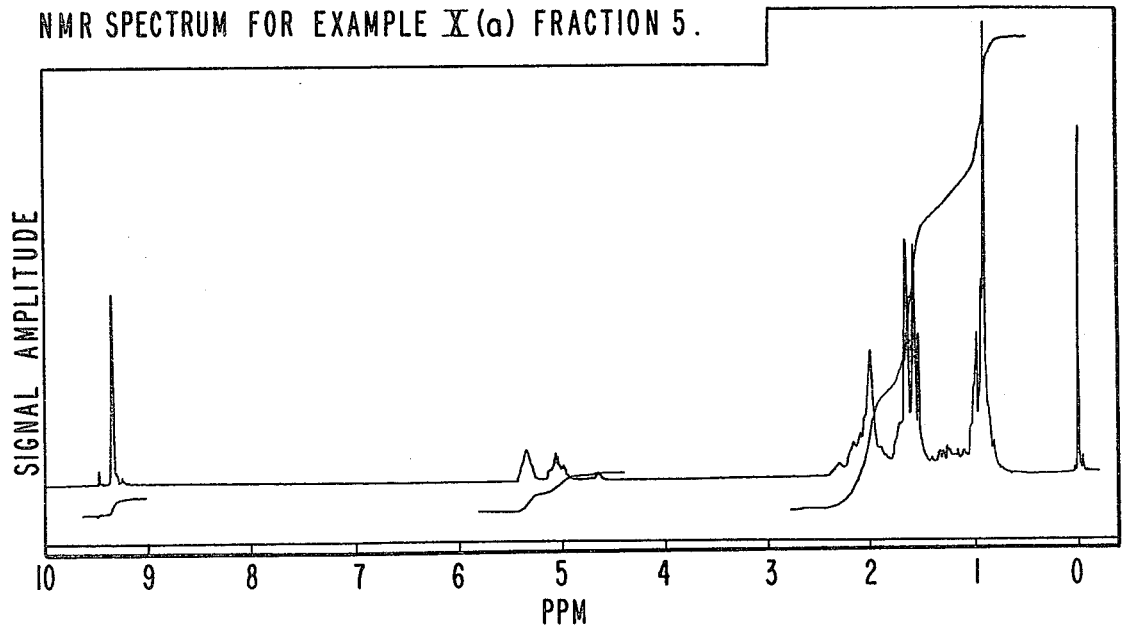

FIG. 17 is the NMR spectrum for the compound having the structure:

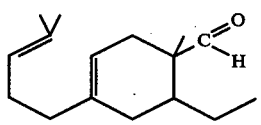

produced according to Example X(A), Fraction 5 of the distillation product.

Figure 18:
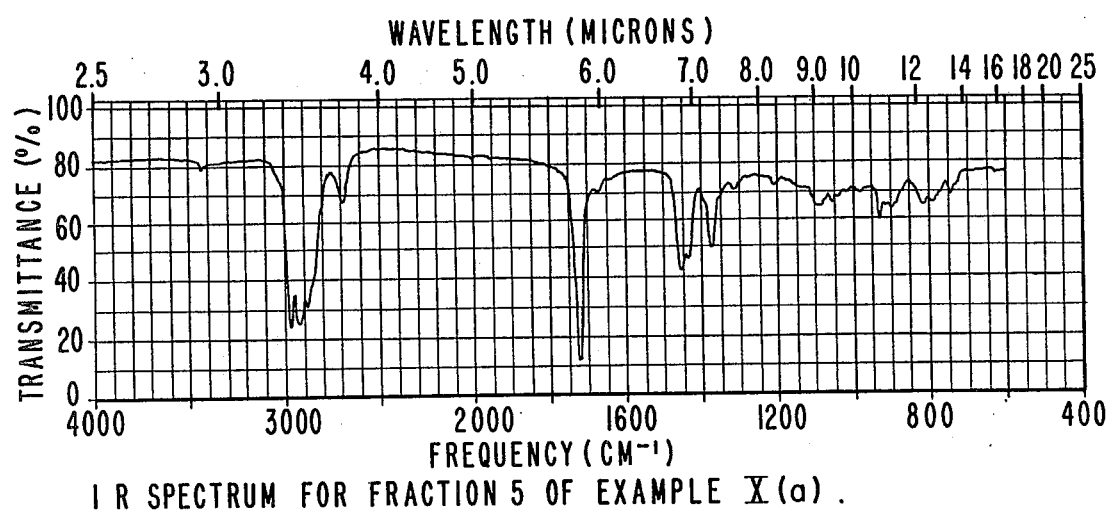

FIG. 18 is the infra-red spectrum for Fraction 5 of the distillation product of the reaction product of Example X(A) having the structure:

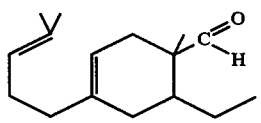

Figure 19:
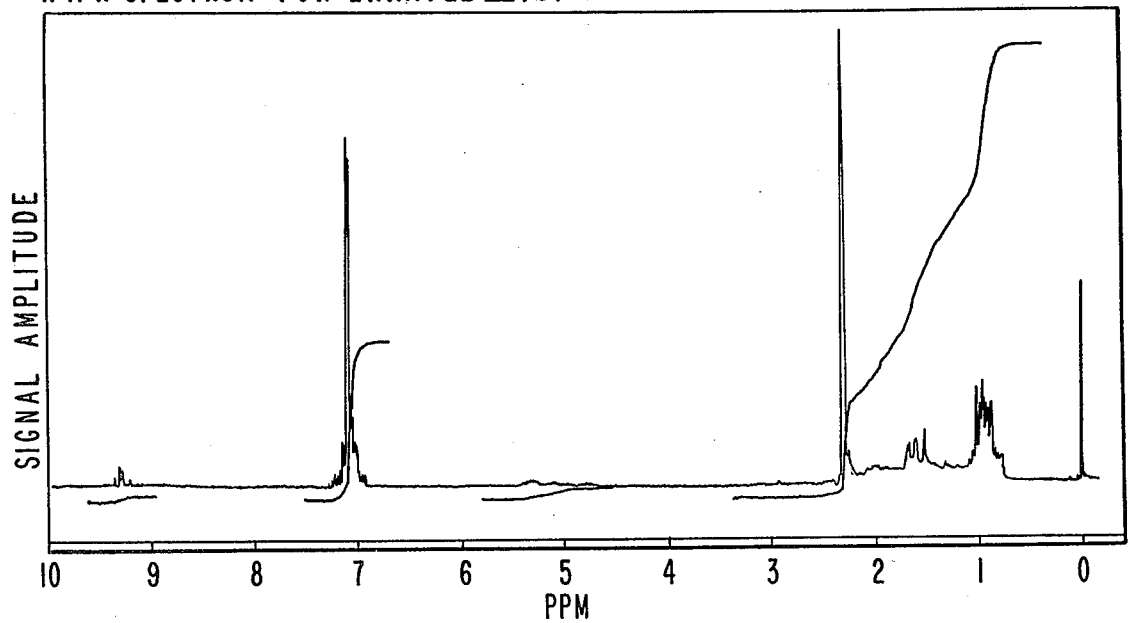

FIG. 19 is the NMR spectrum for the product having the structure:

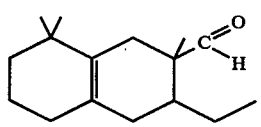

produced according to Example X(B).

Figure 20:
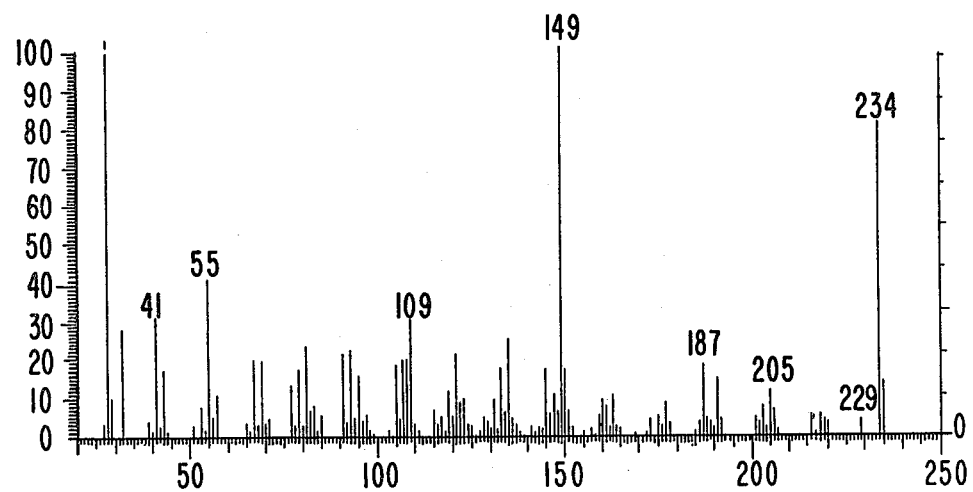

FIG. 20 is the mass spectrum for Fraction 2 of the distillation product of the reaction product of Example X(C) having the structure:

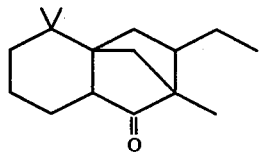

Figure 21:
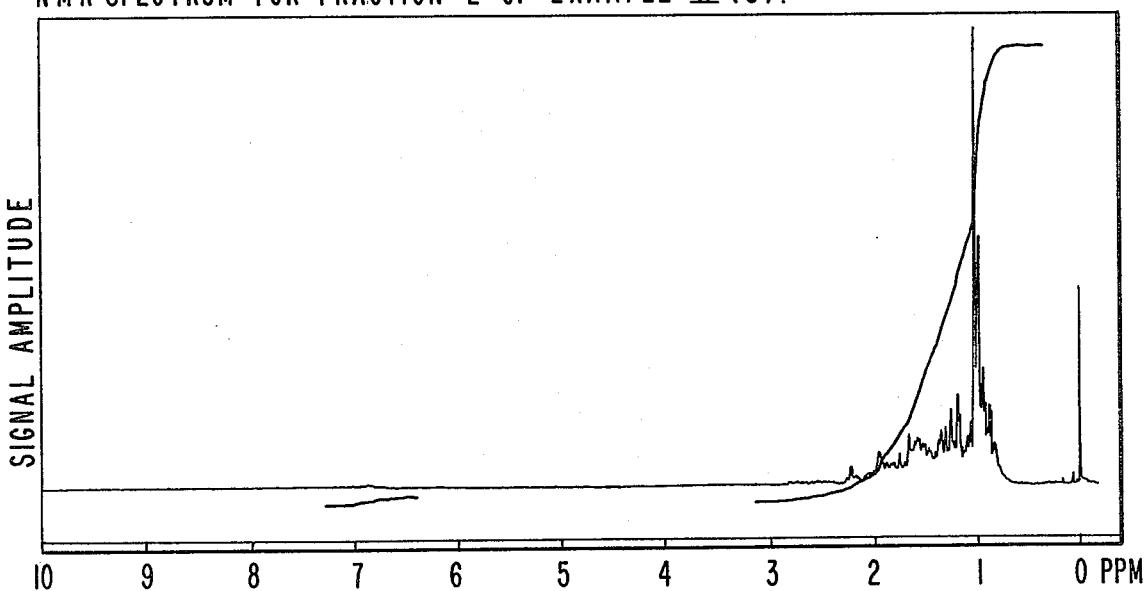

FIG. 21 is the NMR spectrum for Fraction 2 of the distillation product of the reaction product of Example X(C) having the structure:

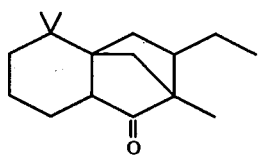

Figure 22:
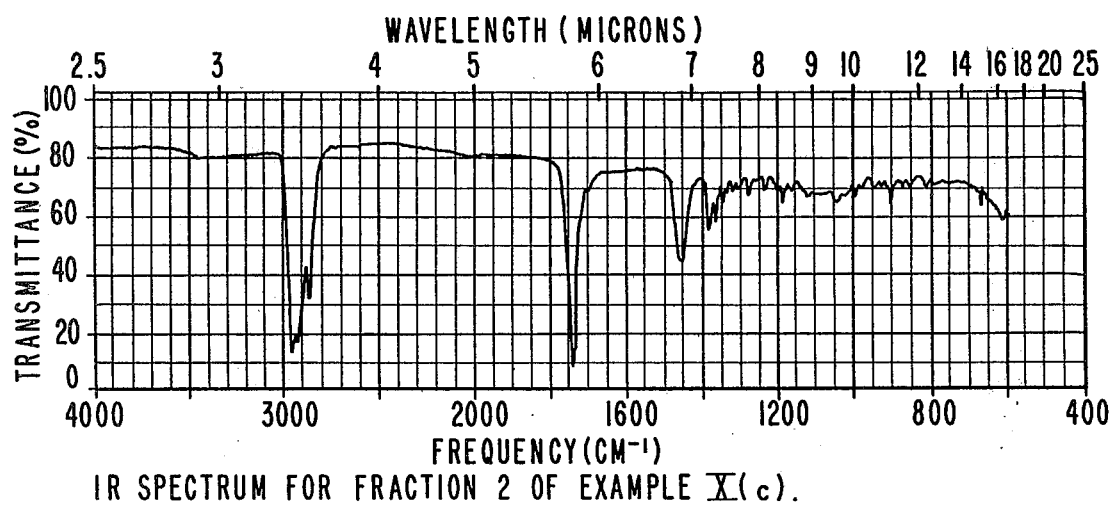

FIG. 22 is the infra-red spectrum for Fraction 2 of the distillation product of the reaction product of Example X(C) having the structure:

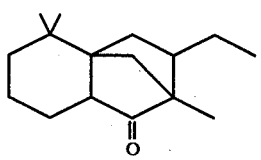

Figure 23:
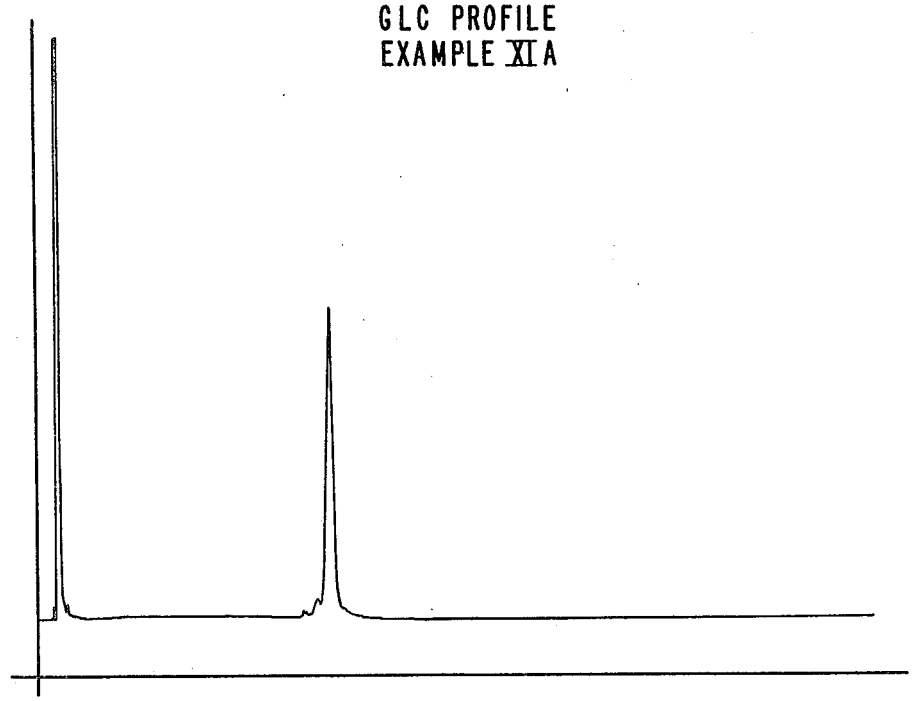

FIG. 23 is the GLC profile for the reaction product of Example XI(A) containing the compound having the structure:

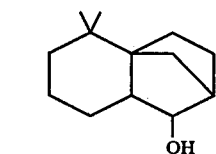

FIG. 24 is the mass spectrum of the reaction product of Example XI(A) containing the compound having the structure:

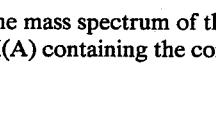

FIG. 25 is the NMR spectrum for the reaction product of Example XI(A) containing the compound having the structure:

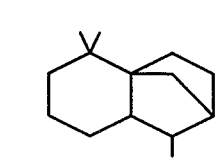

Figure 26:
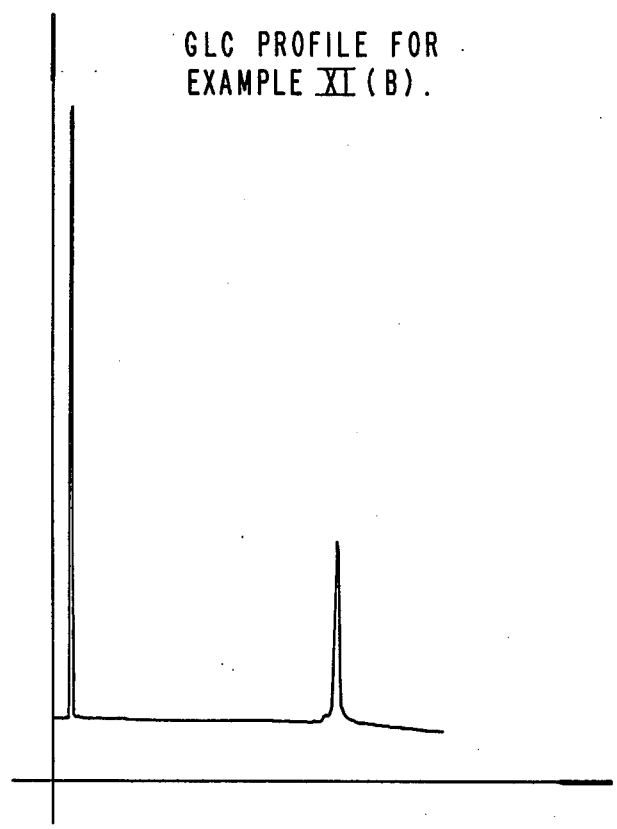

FIG. 26 is the GLC profile of the reaction product of Example XI(B) containing the compound having the structure:

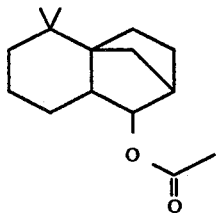

Figure 27:
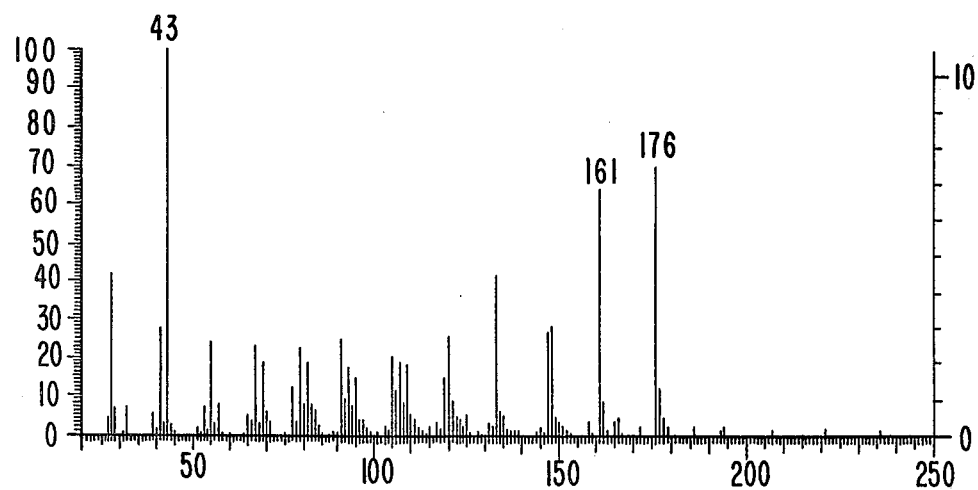

FIG. 27 is the mass spectrum for the reaction product of Example XI(B) containing the compound having the structure:

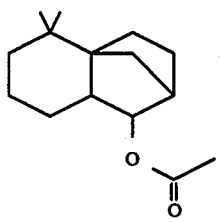

(bulked Fractions 1 and 2).

Figure 28:
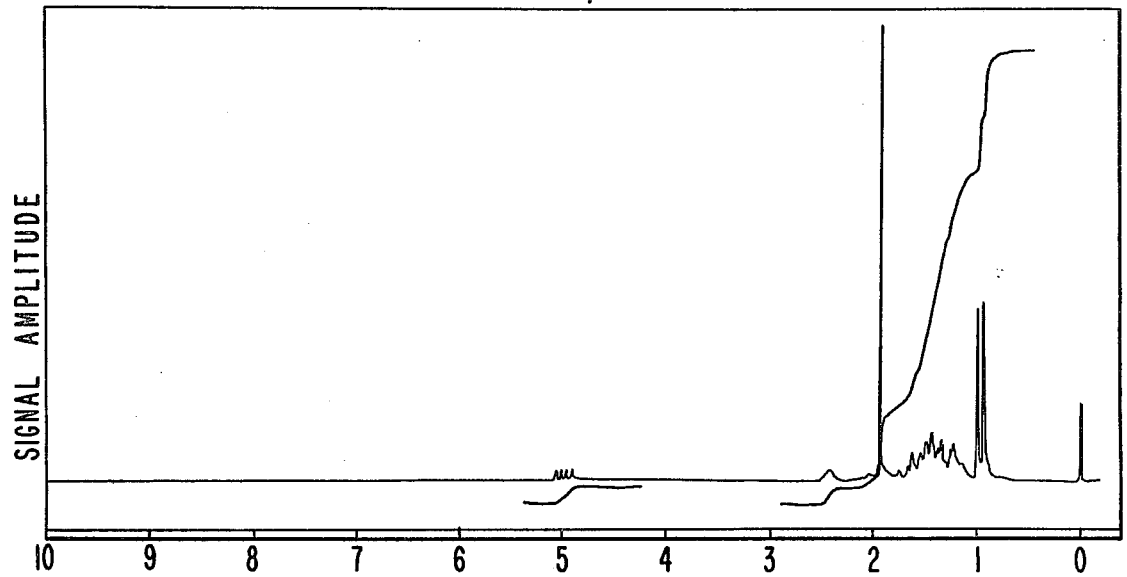

FIG. 28 is the NMR spectrum for bulked Fractions 1 and 2 of the distillation product of the reaction product of Example XI(B) containing the compound having the structure:

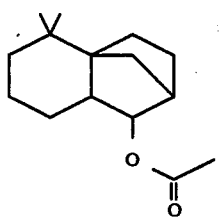

Figure 29:
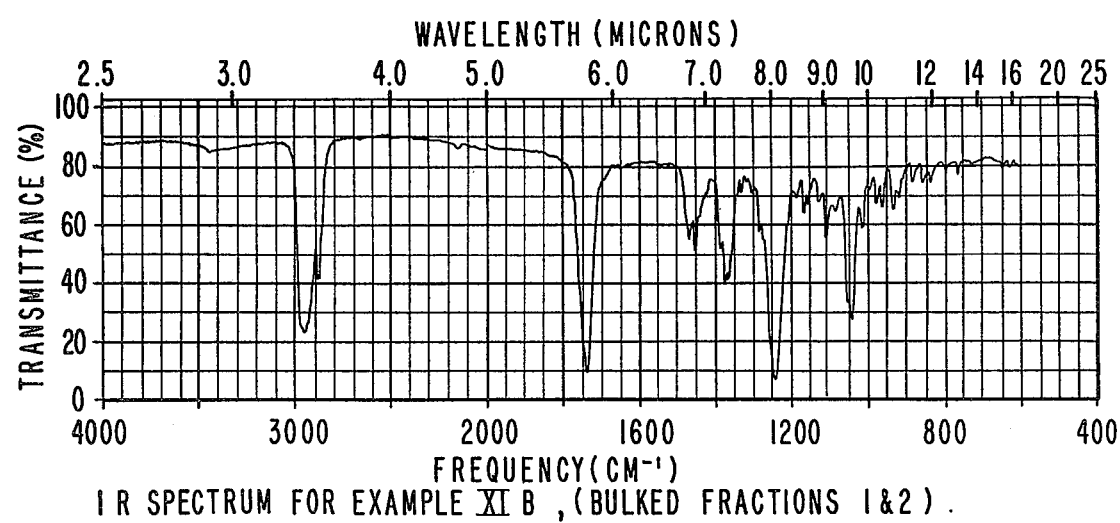

FIG. 29 is the infra-red spectrum for bulked Fractions 1 and 2 of the distillation product of the reaction product of Example XI(B) containing the compound having the structure:

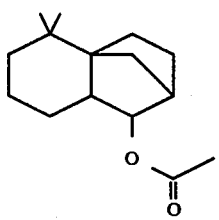

Figure 30:
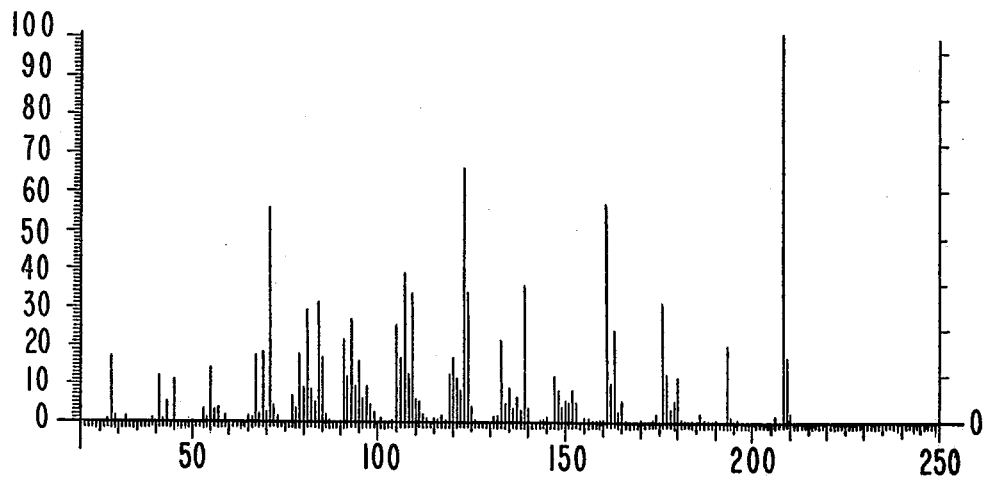

FIG. 30 is the mass spectrum for Fraction 3 of the distillation product of the reaction product of Example XI(C) containing the compound having the structure:

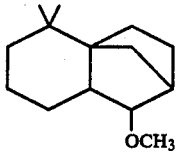

Figure 31:
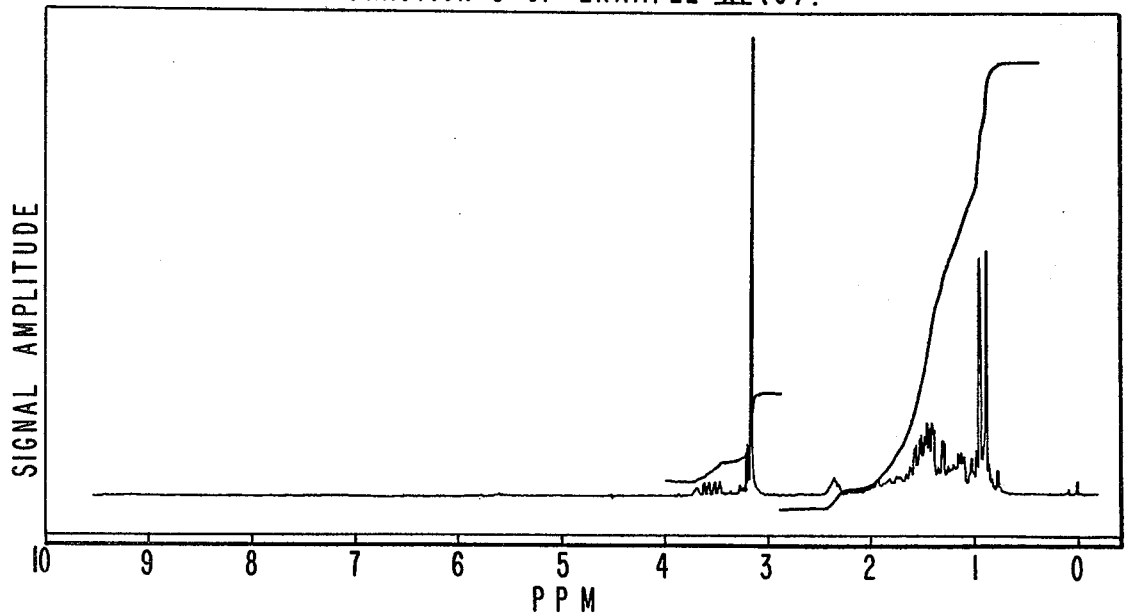

FIG. 31 is the NMR spectrum for Fraction 3 of the distillation product of the reaction product of Example XI(C) containing the compound having the structure:

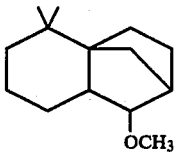

Figure 32:
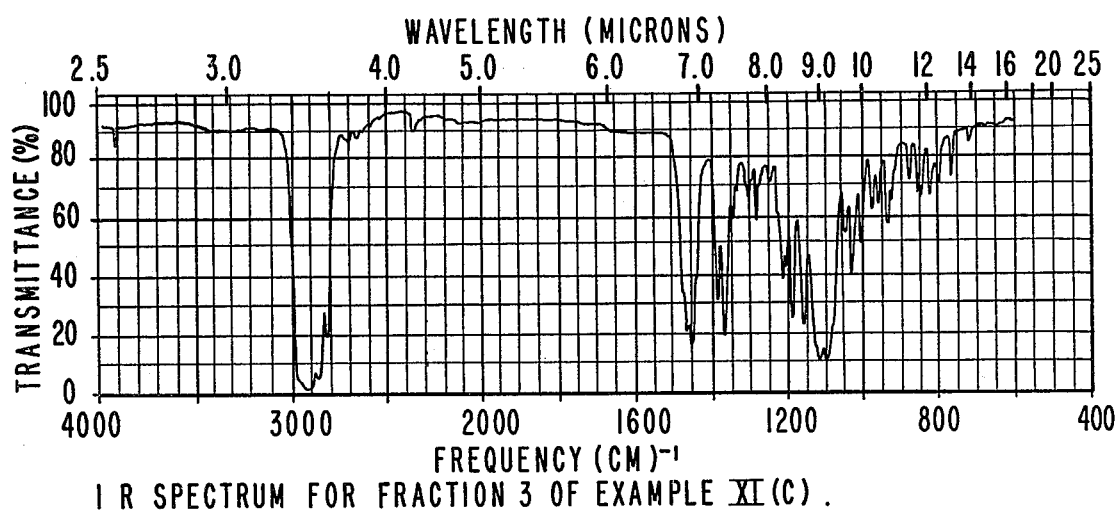

FIG. 32 is the infra-red spectrum for Fraction 3 of the distillation product of the reaction product of Example XI(C) containing the compound having the structure:

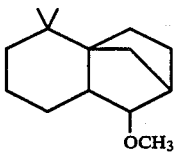

Figure 33:
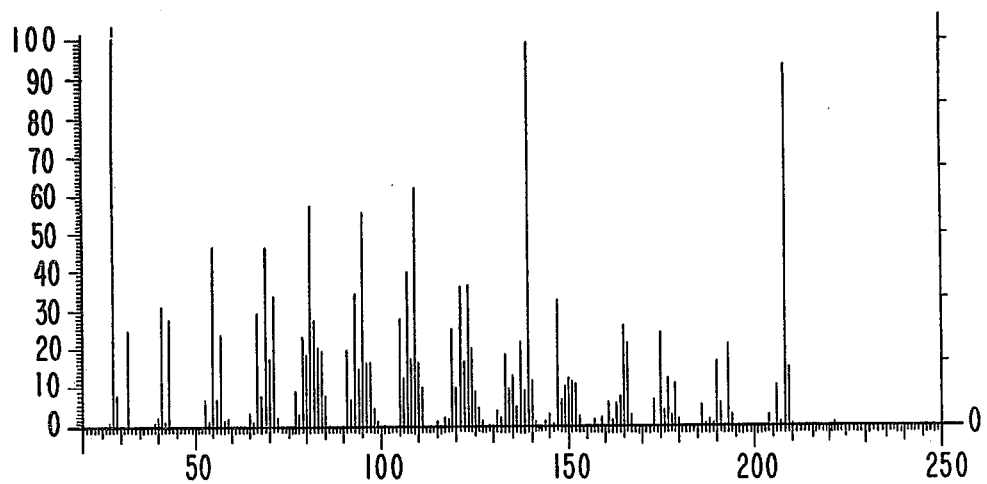

FIG. 33 is the mass spectrum for the reaction product of Example XII(A) containing the compound having the structure:

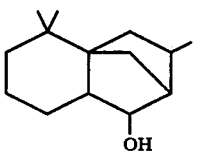

Figure 34:
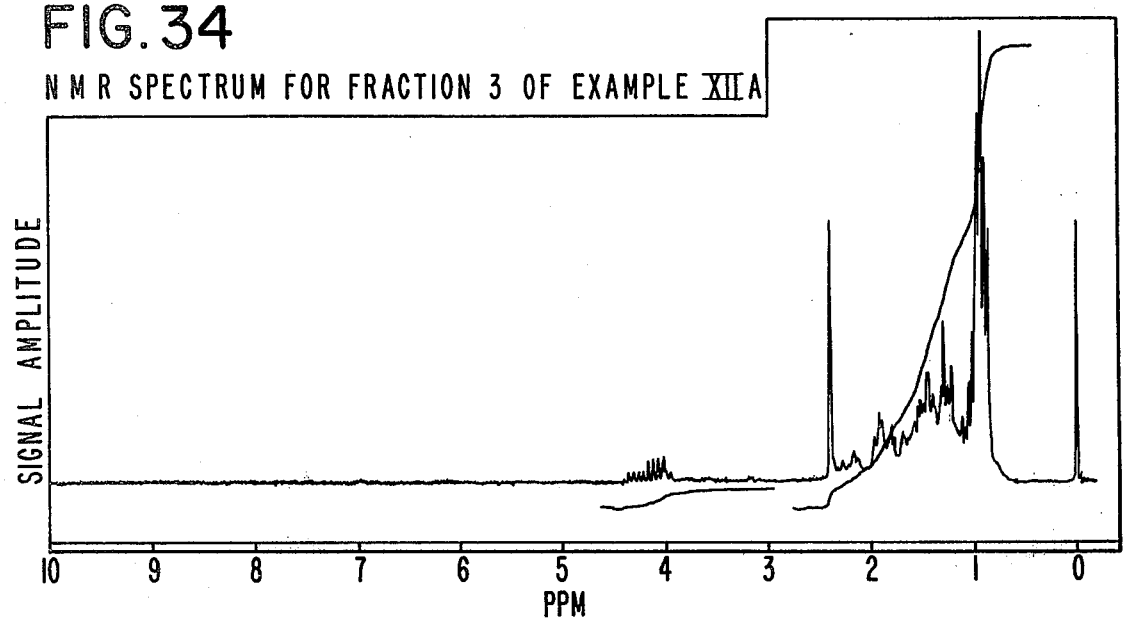

FIG. 34 is the NMR spectrum for Fraction 3 of the distillation product of the reaction product of Example XII(A) containing the compound having the structure:

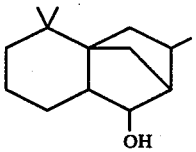

Figure 35:
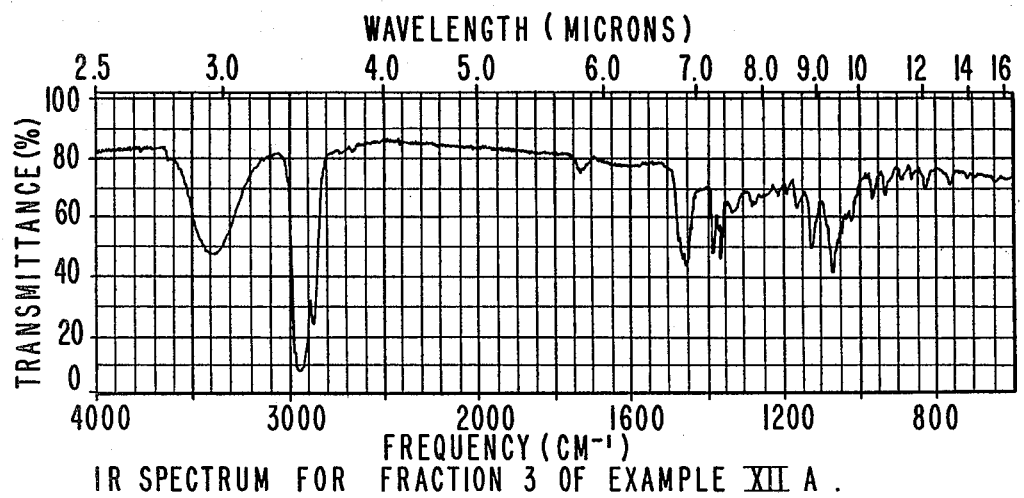

FIG. 35 is the infra-red spectrum for Fraction 4 of the distillation product of the reaction product of Example XII(A) containing the compound having the structure:

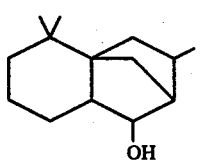

Figure 36:
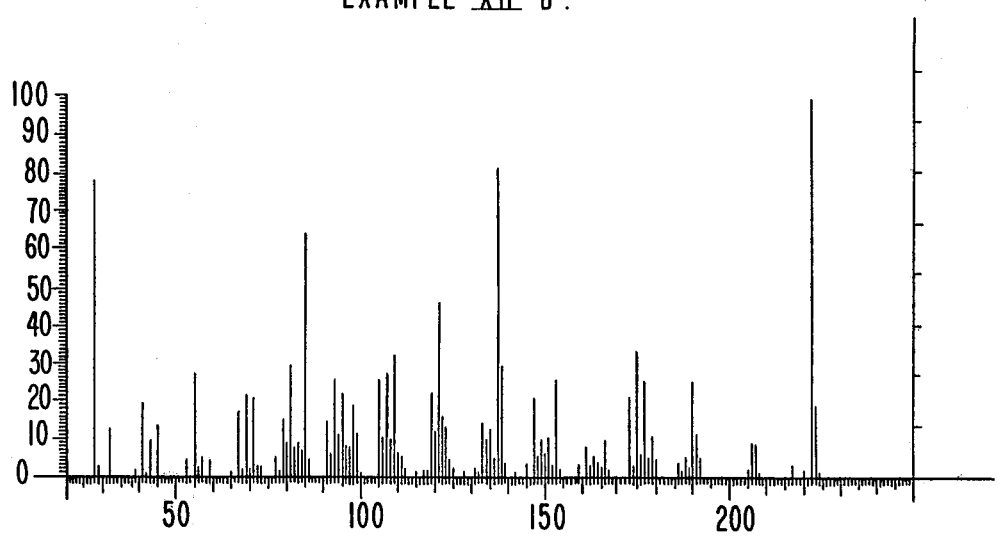

FIG. 36 is the mass spectrum of the reaction product of Example XII(B) containing the compound having the structure:

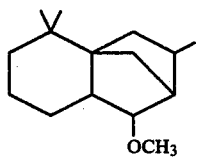

Figure 37:
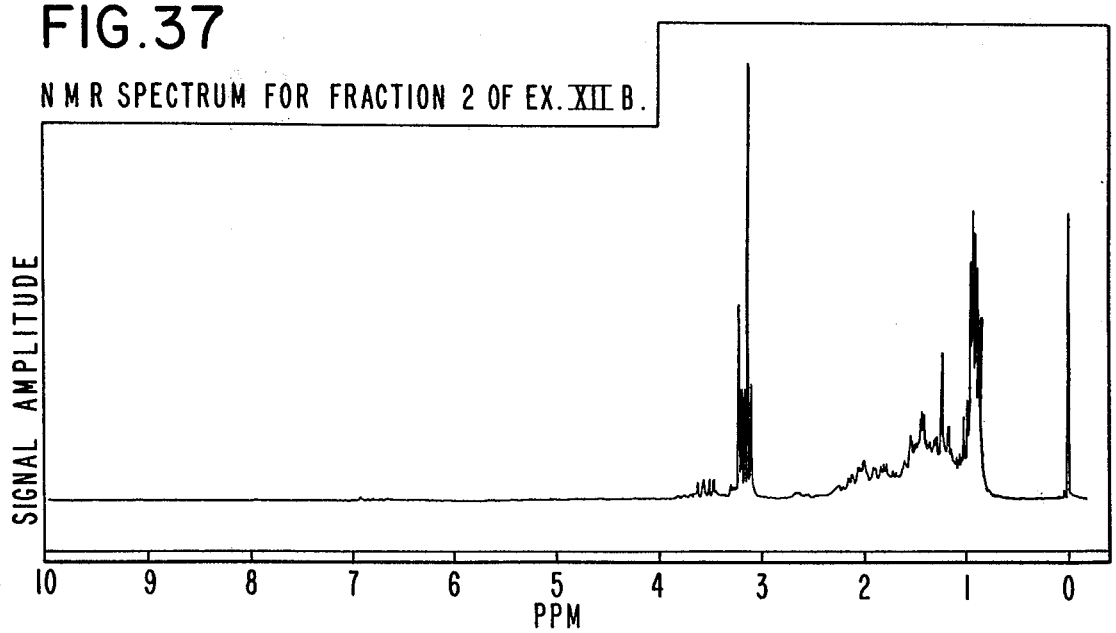

FIG. 37 is the NMR spectrum for Fraction 2 of the distillation product of the reaction product of Example XII(B) containing the compound having the structure:

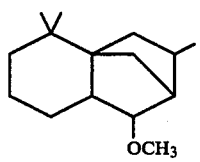

Figure 38:
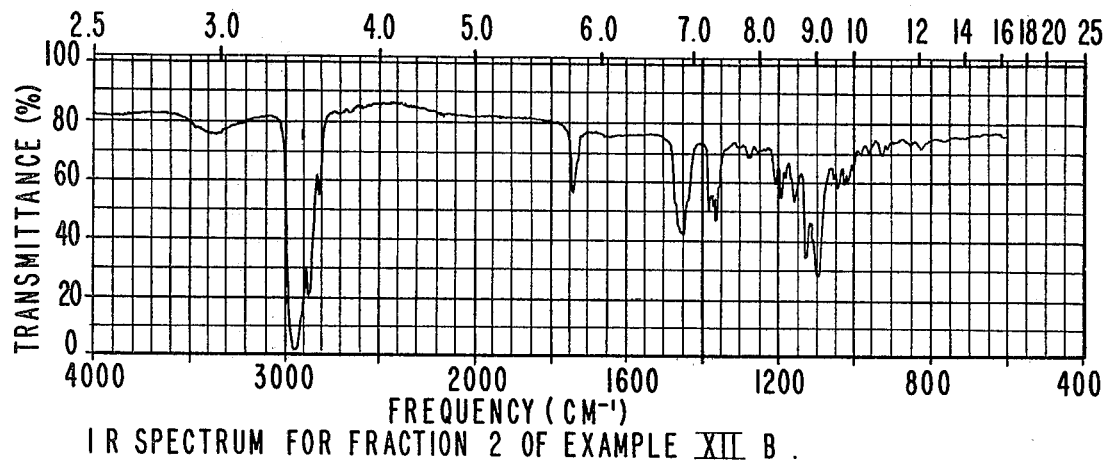

FIG. 38 is the infra-red spectrum for Fraction 2 of the distillation product of the reaction product of Example XII(B) containing the compound having the structure:

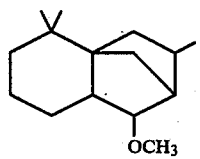

Figure 39:
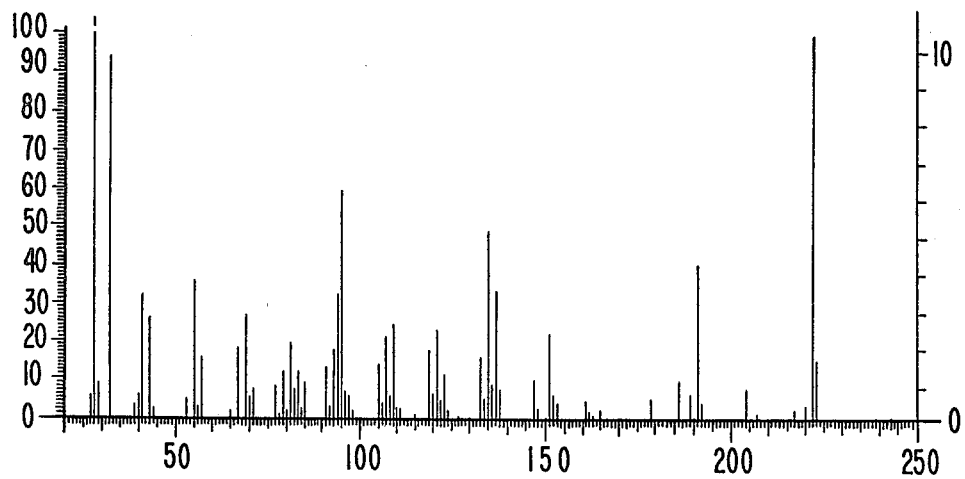

FIG. 39 is the mass spectrum for the reaction product of Example XIII(A) containing the compound having the structure:

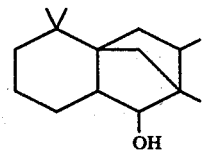

FIG. 40 is the NMR spectrum for Fraction 3 of the distillation product of the reaction product of Example XIII(A) containing the compound having the structure:

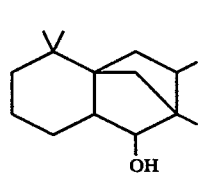

FIG. 41 is the infra-red spectrum for the distillation product of the reaction product of Example XIII(A) containing the compound having the structure:

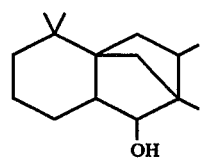

Figure 42:
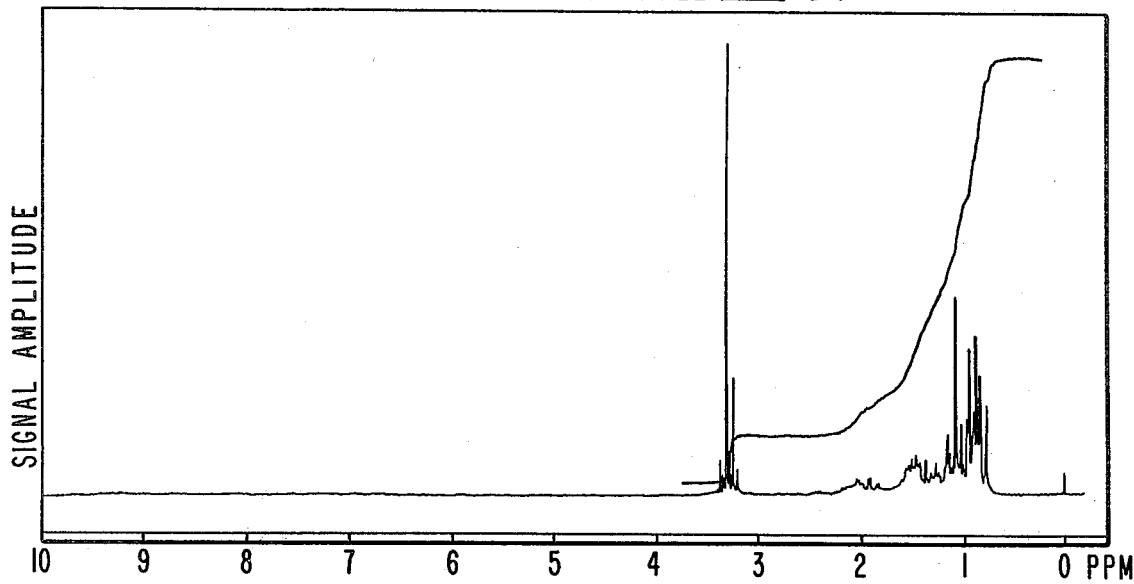

FIG. 42 is the NMR spectrum for Fraction 3 of the distillation product of the reaction product of Example XIII(B) containing the compound having the structure:

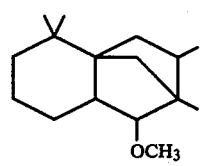

Figure 43:
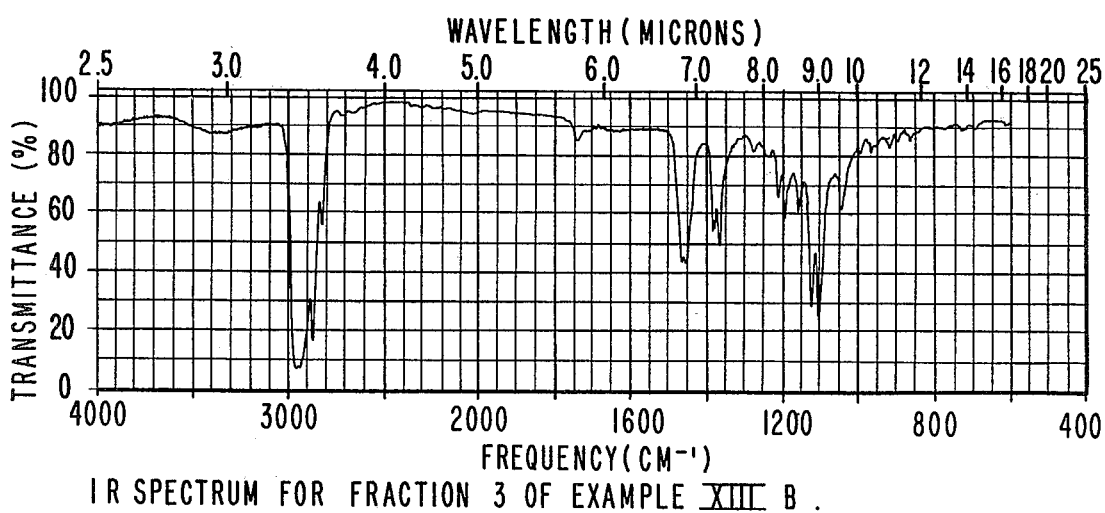

FIG. 43 is the infra-red spectrum for Fraction 3 of the distillation product of the reaction product of Example XIII(B) containing the compound having the structure:

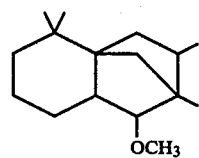

Figure 44:
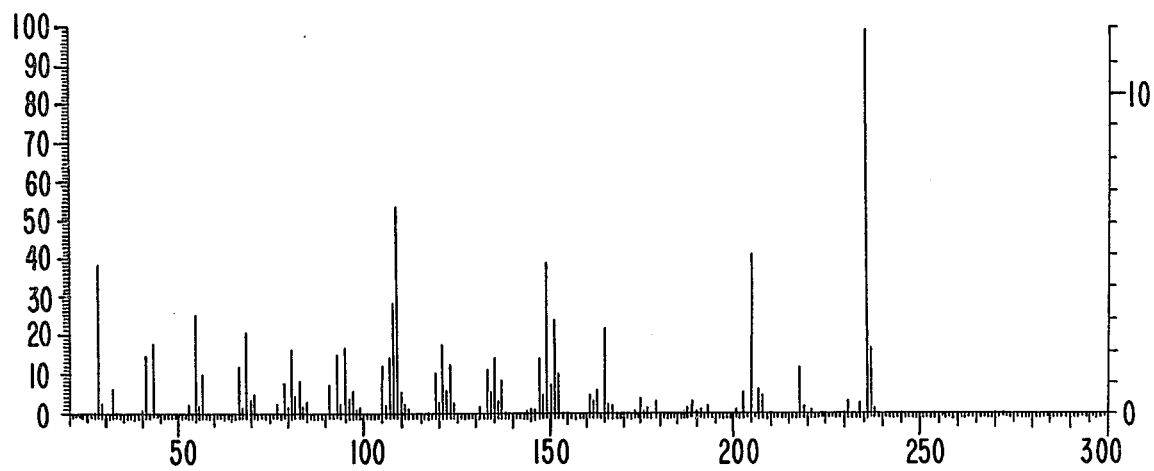

FIG. 44 is the mass spectrum for the reaction product of Example XIV(A) containing the compound having the structure:

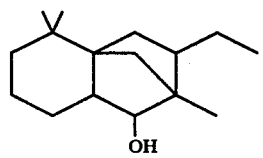

Figure 45:
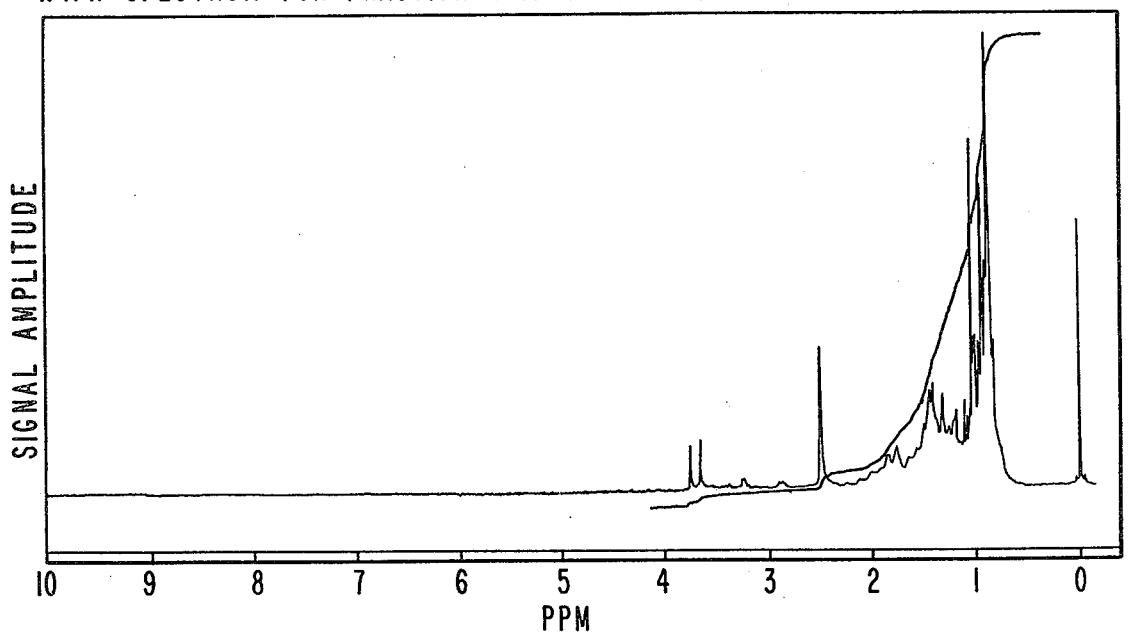

FIG. 45 is the NMR spectrum for Fraction 4 of the distillation product of the reaction product of Example XIV(A) containing the compound having the structure:

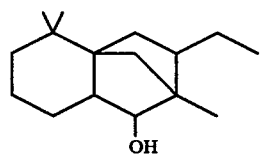

Figure 46:
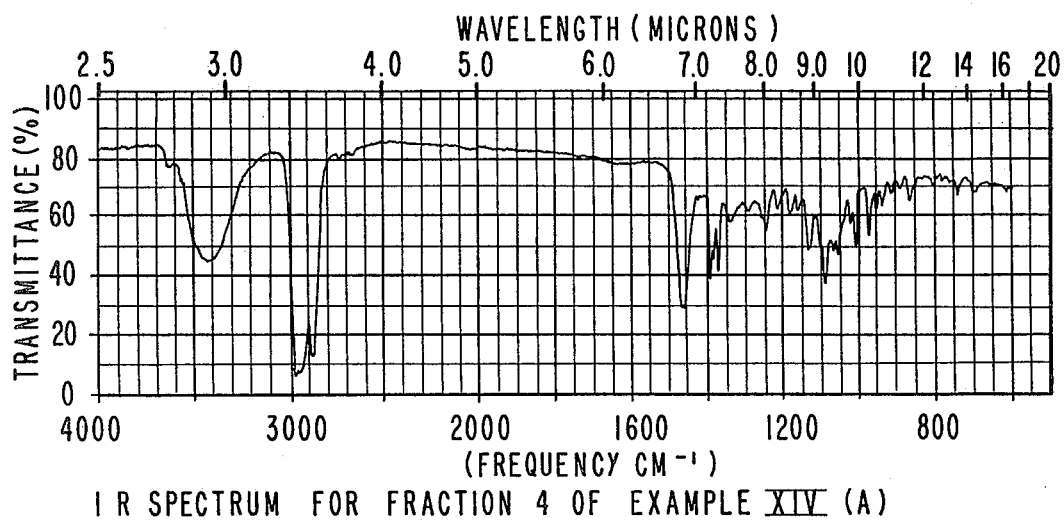

FIG. 46 is the infra-red spectrum for Fraction 4 of the distillation product of the reaction product of Example XIV(A) containing the compound having the structure:

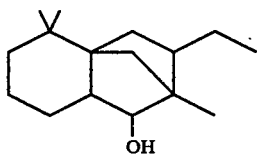

Figure 47:
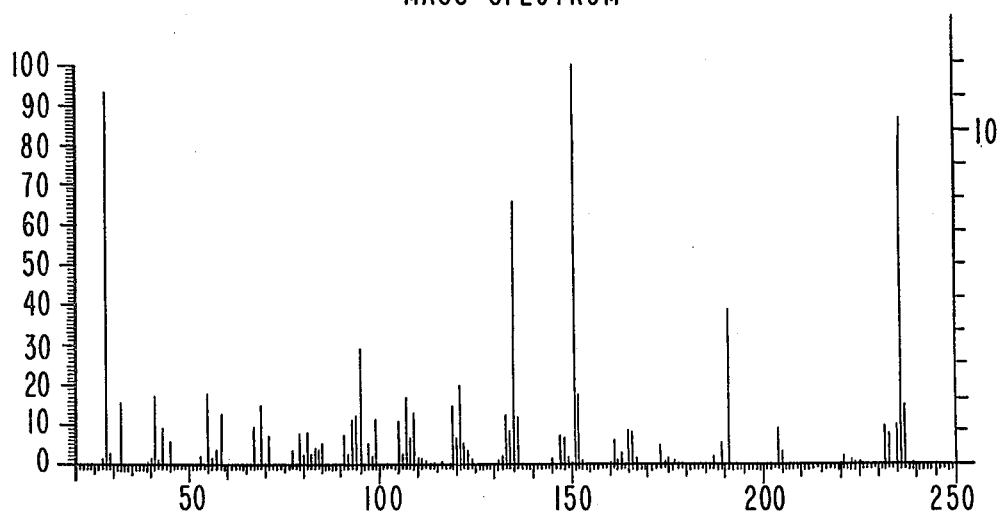

FIG. 47 is the mass spectrum for the reaction product of Example XIV(B) containing the compound having the structure:

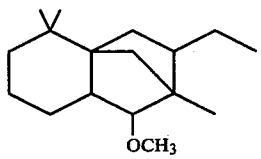

Figure 48:
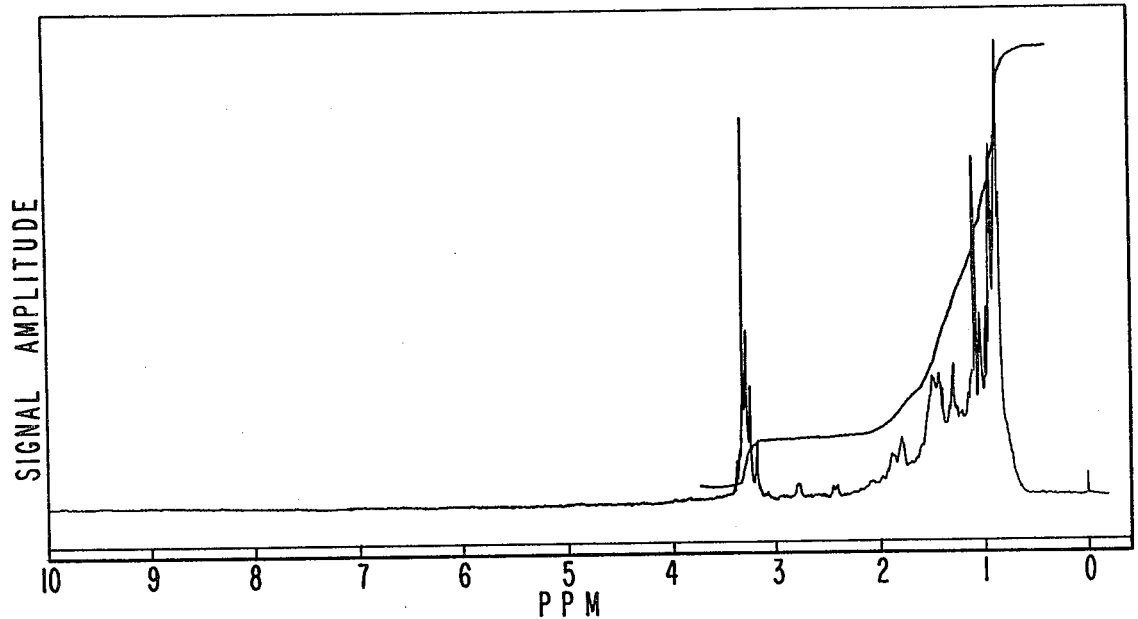

FIG. 48 is the NMR spectrum for Fraction 4 of the distillation product of the reaction product of Example XIV(B) containing the compound having the structure:

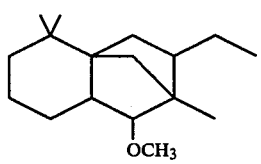

Figure 49:
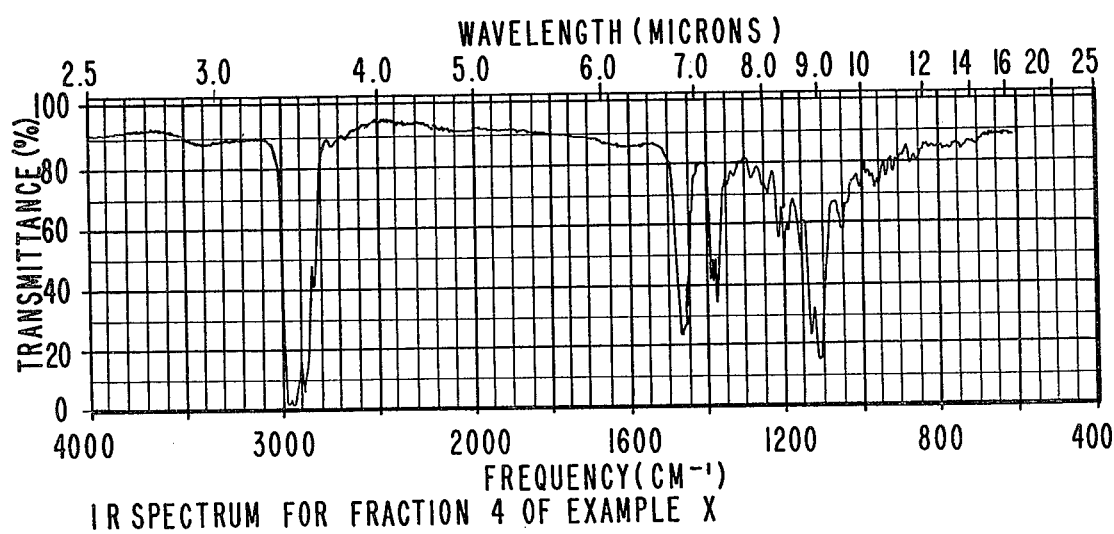

FIG. 49 is the infra-red spectrum for Fraction 4 of the distillation product of the reaction product of Example XIV(B) containing the compound having the structure:

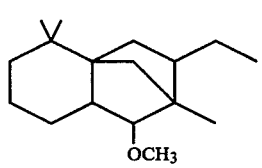

Figure 50:
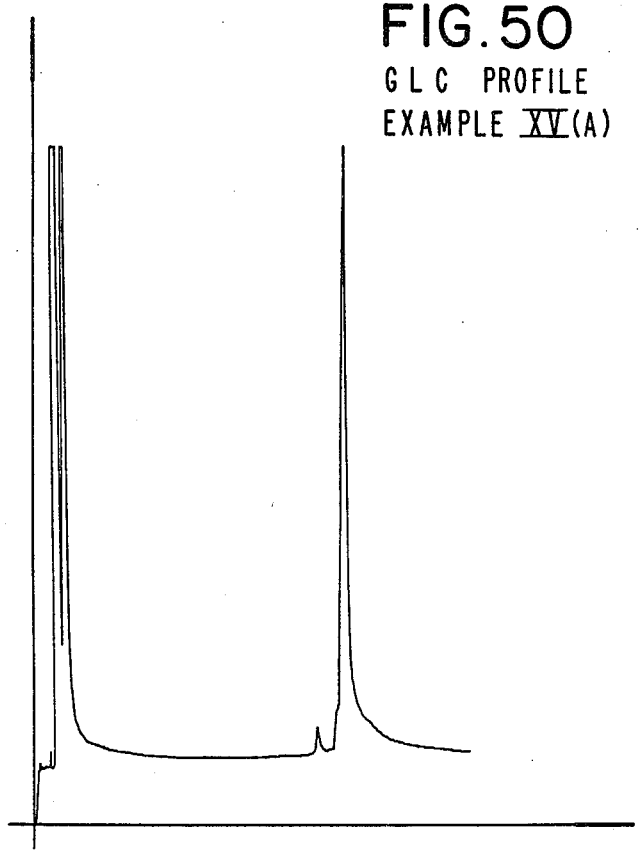

FIG. 50 is the GLC profile for the reaction product of Example XV(A) containing the compound having the structure:

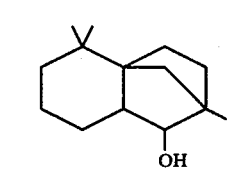

Figure 51:
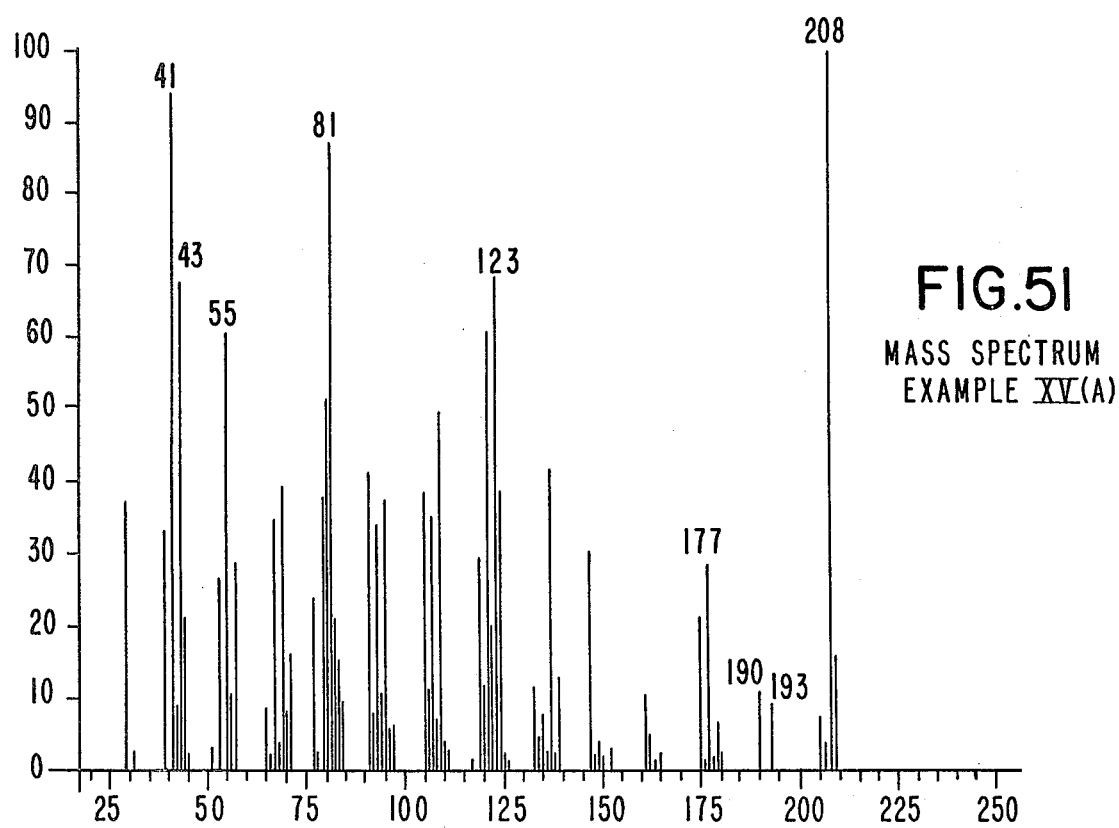
Figure 52:
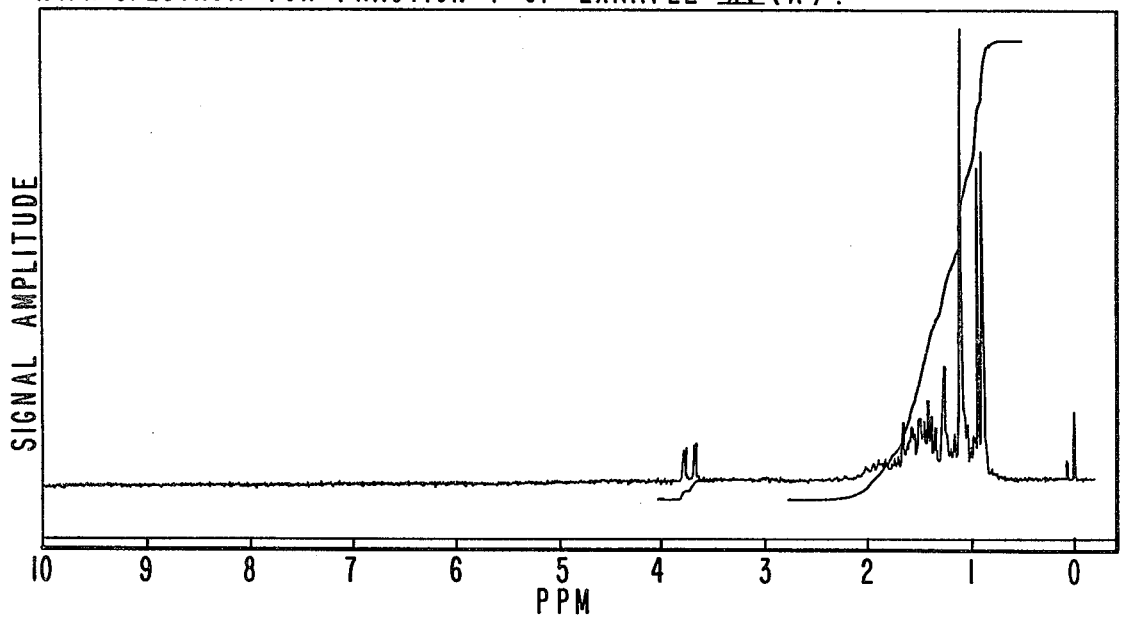

FIG. 51 is the mass spectrum for the reaction product of Example XV(A) containing the compound having the structure:

FIG. 52 is the NMR spectrum for Fraction 1 of the distillation product of the reaction product of Example XV(A) containing the compound having the structure:

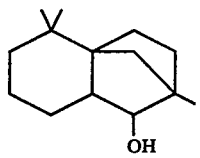

Figure 53:
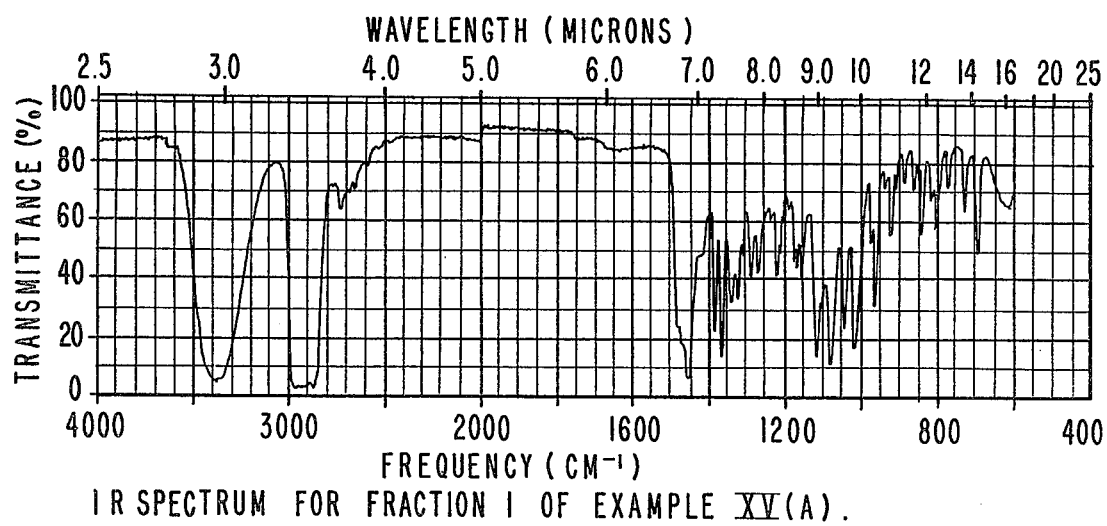

FIG. 53 is the infra-red spectrum for Fraction 1 of the distillation product of the reaction product of Example XV(A) containing the compound having the structure:

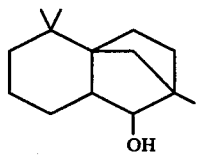

Figure 54:
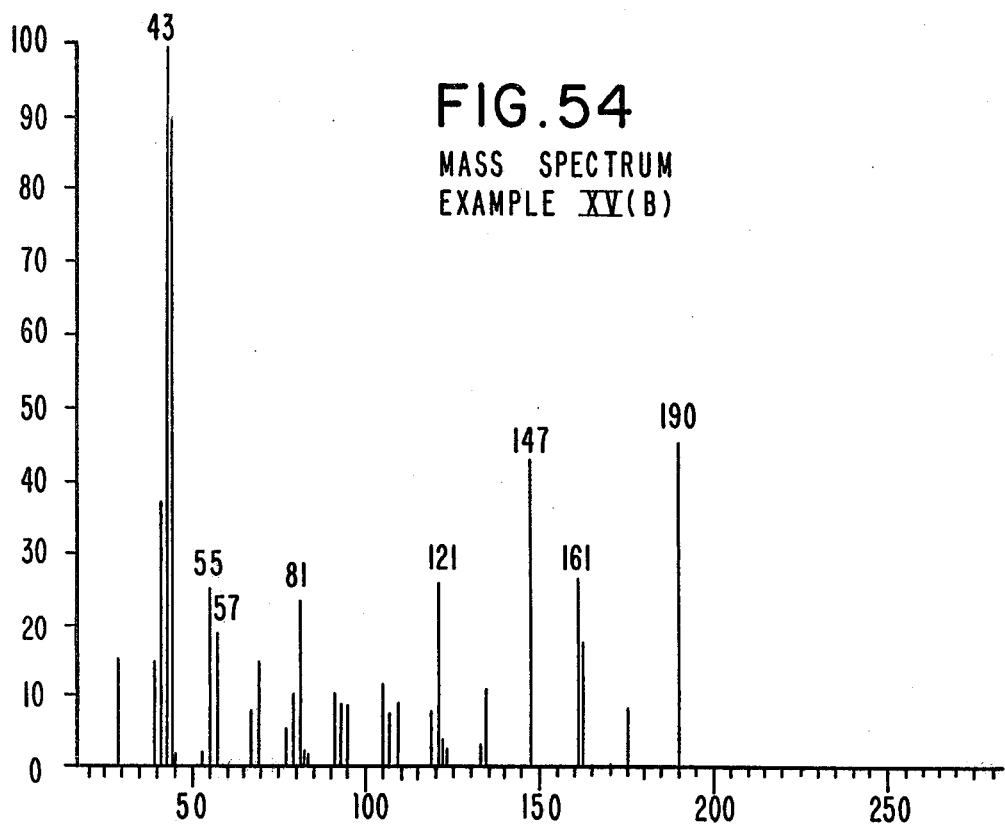

FIG. 54 is the mass spectrum for the reaction product of Example XV(B) containing the compound having the structure:

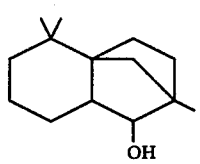

Figure 55:
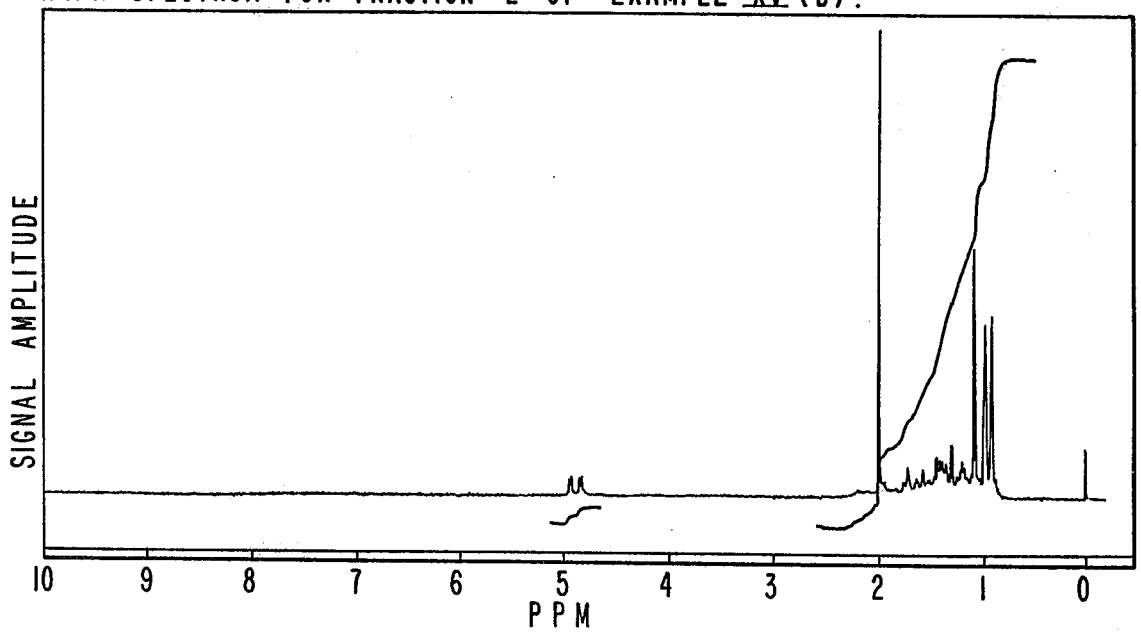

FIG. 55 is the NMR spectrum for Fraction 2 of the distillation product of the reaction product of Example XV(B) containing the compound having the structure:

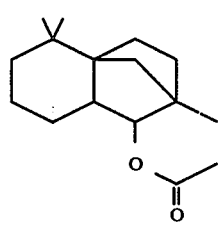

Figure 56:
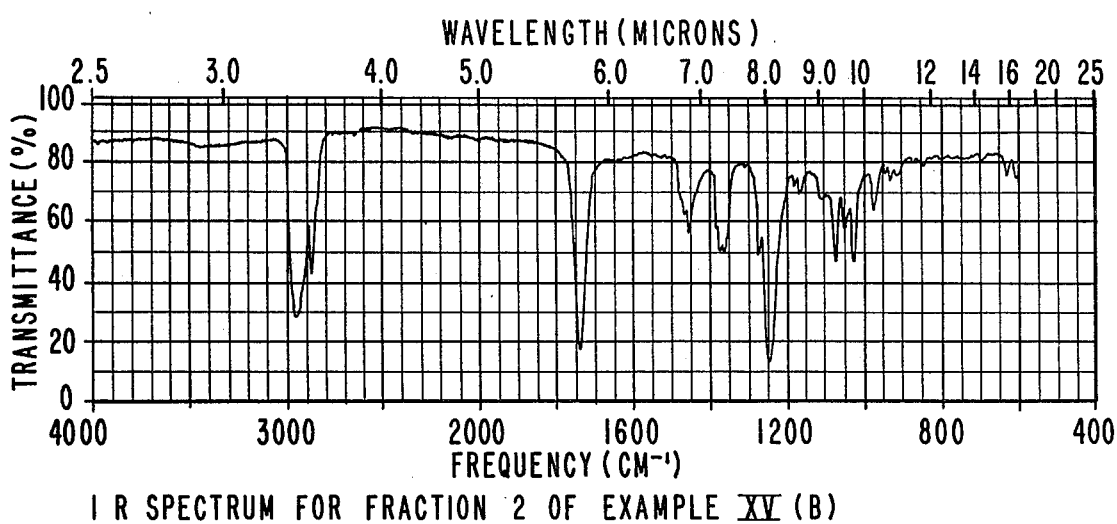

FIG. 56 is the infra-red spectrum of Fraction 2 of the distillation product of the reaction product of Example XV(B) containing the compound having the structure:

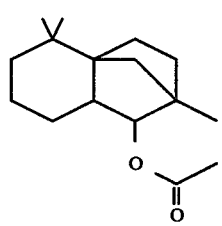

Figure 57:
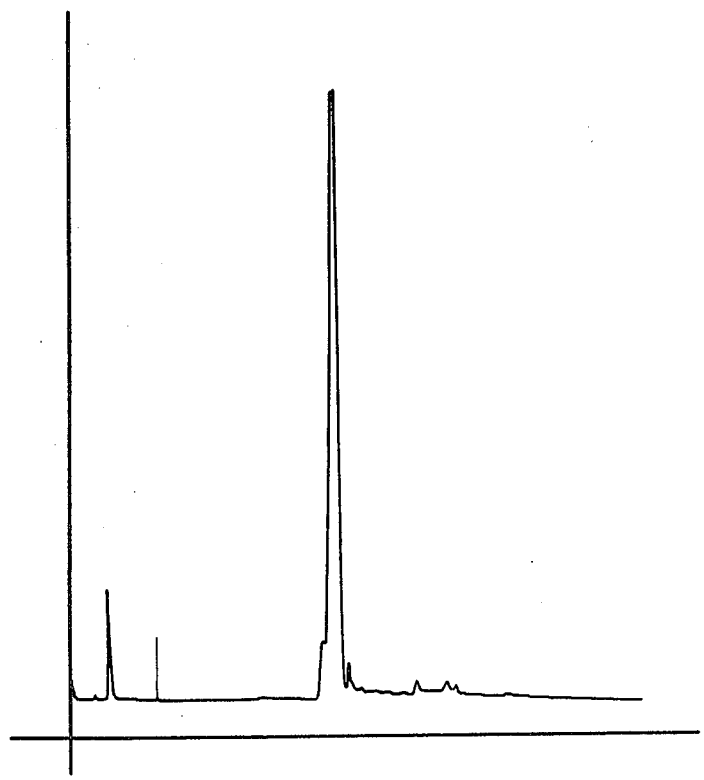

FIG. 57 is the GLC profile for the reaction product of Example XV(C) containing the compound having the structure:

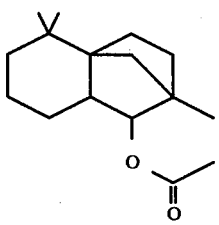

Figure 58:
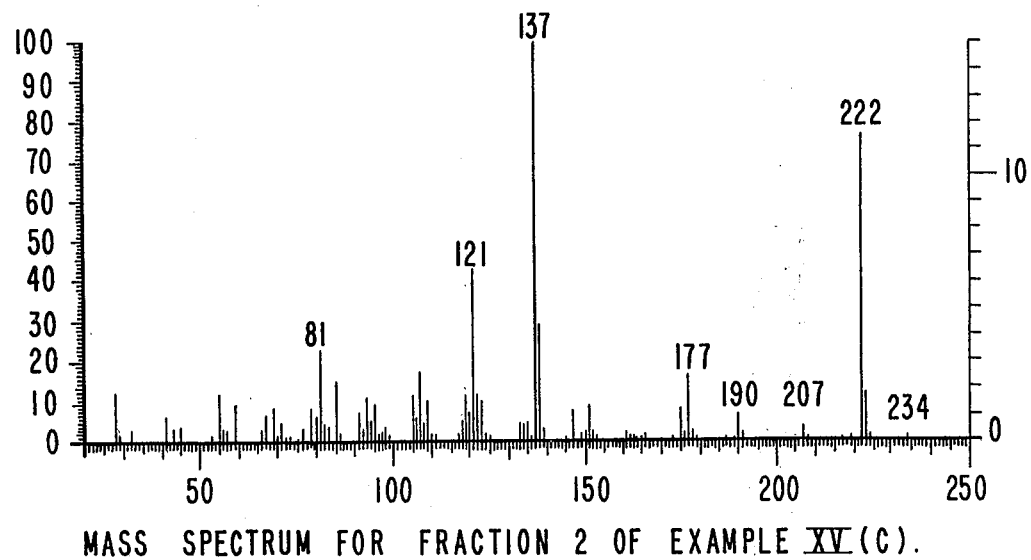

FIG. 58 is the mass spectrum for Fraction 2 of the distillation product of the reaction product of Example XV(C) containing the compound having the structure:

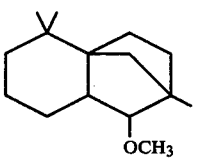

Figure 59:
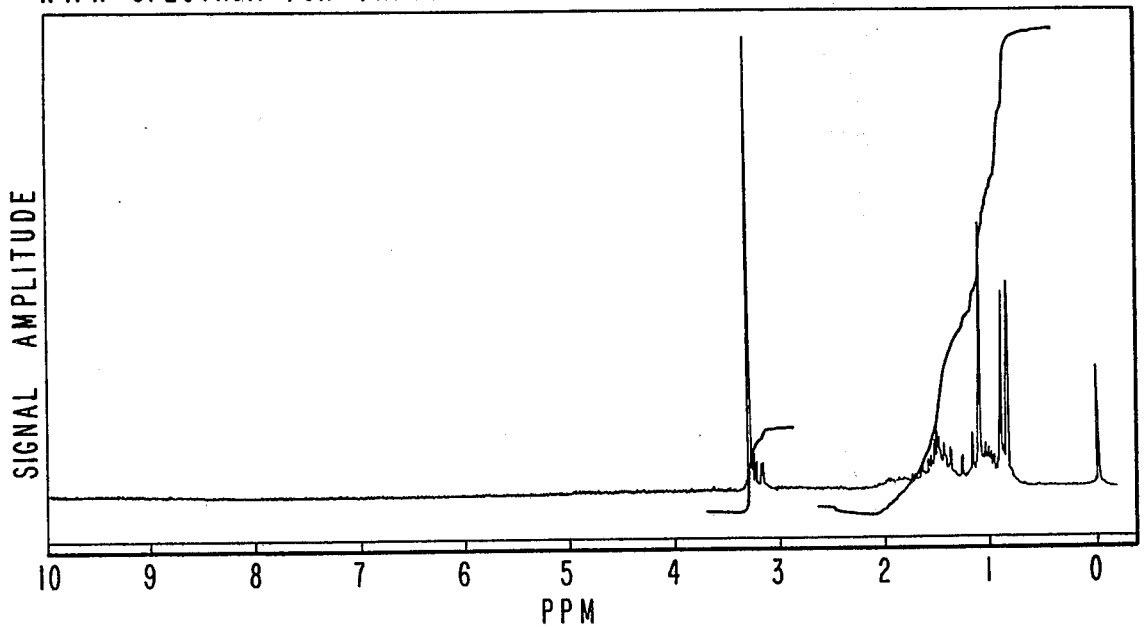

FIG. 59 is the NMR spectrum for Fraction 2 of the distillation product of the reaction product of Example XV(C) containing the compound having the structure:

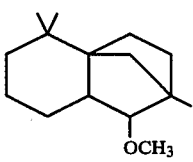

Figure 60:
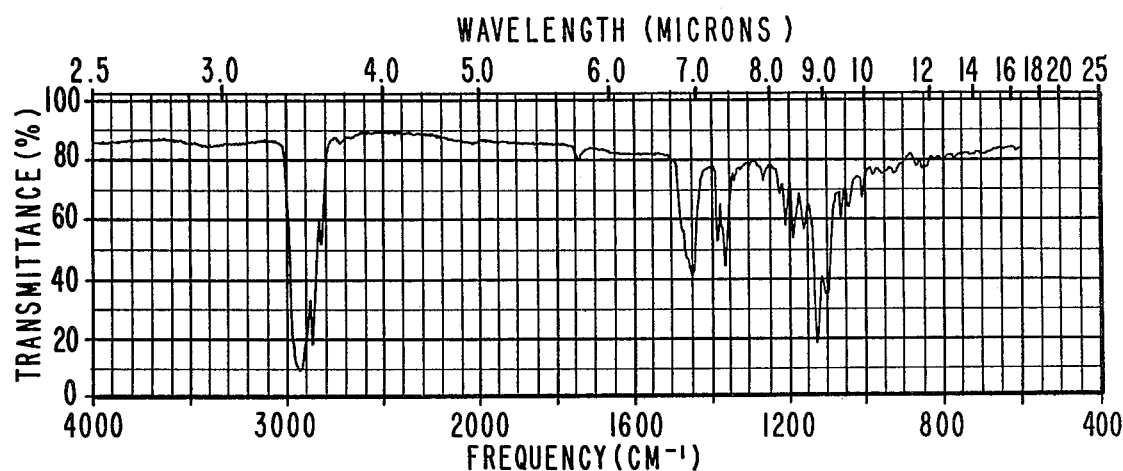

FIG. 60 is the infra-red spectrum for Fraction 2 of the distillation product of the reaction product of Example XV(C) containing the compound having the structure:

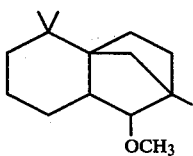

Figure 61:
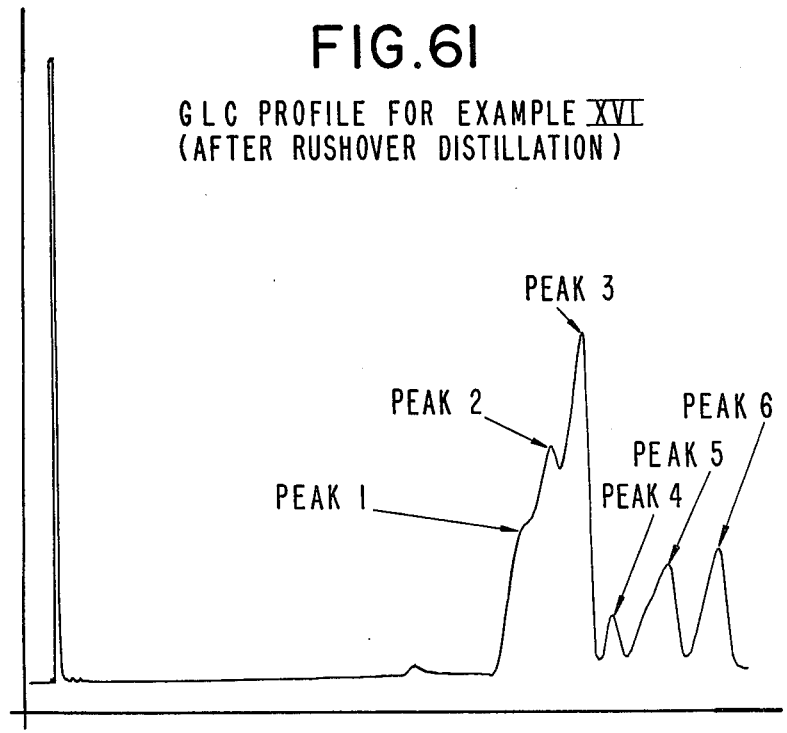

FIG. 61 is the GLC profile for the reaction product for Example XVI containing the compound having the structure:

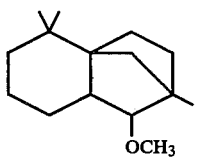

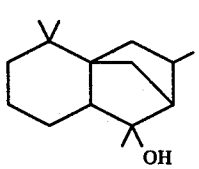

the GLC profile containing six peaks numbered as Peak 1, Peak 2, Peak 3, Peak 4, Peak 5 and Peak 6.

FIG. 62 is the mass spectrum for Peak 1 of the GLC profile of FIG. 61.

FIG. 63 is the NMR spectrum for Peak 1 of the GLC profile of FIG. 61.

Figure 64:
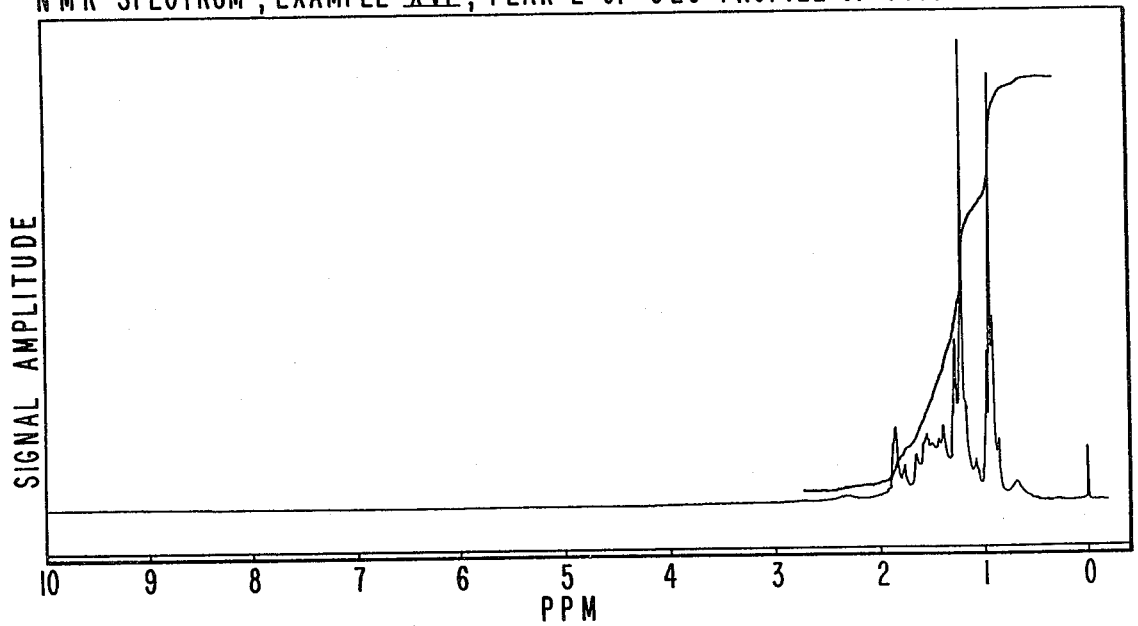

FIG. 64 is the NMR spectrum for Peak 2 of the GLC profile of FIG. 61.

Figure 65:
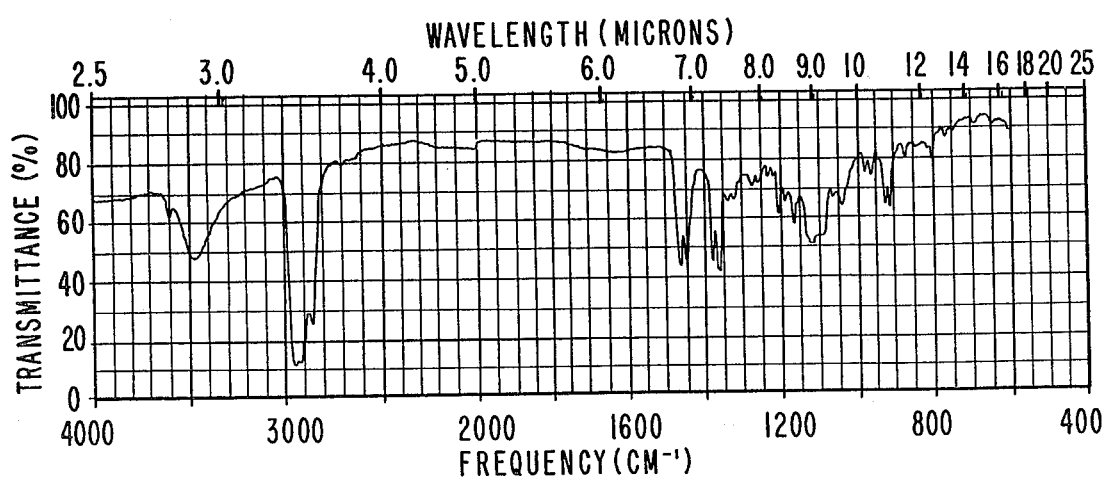

FIG. 65 is the infra-red spectrum for Peak 2 of the GLC profile of FIG. 61.

Figure 66:
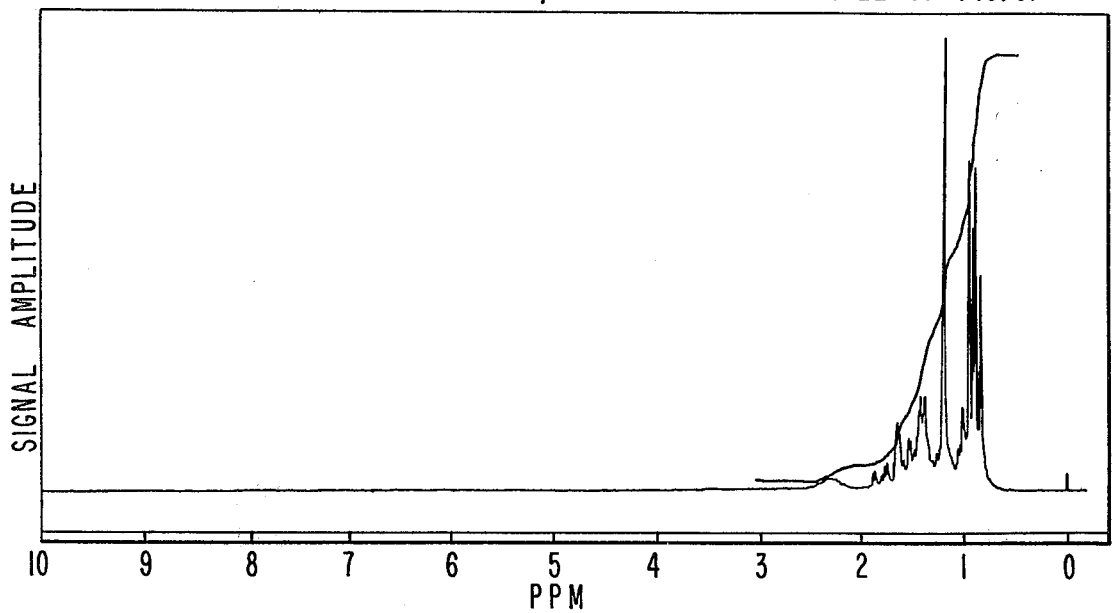

FIG. 66 is the NMR spectrum for Peak 3 of the GLC profile of FIG. 61.

Figure 67:
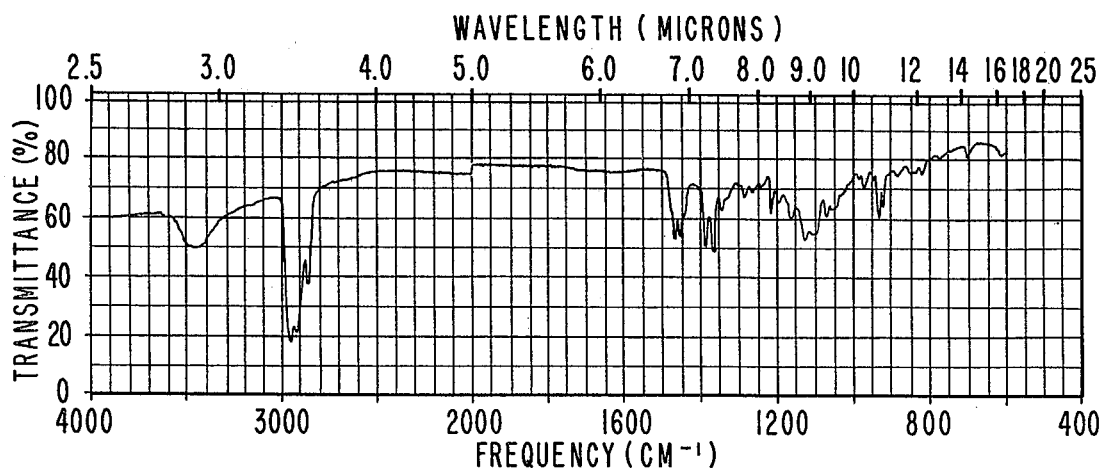

FIG. 67 is the infra-red spectrum for Peak 3 of the GLC profile of FIG. 61.

Figure 68:
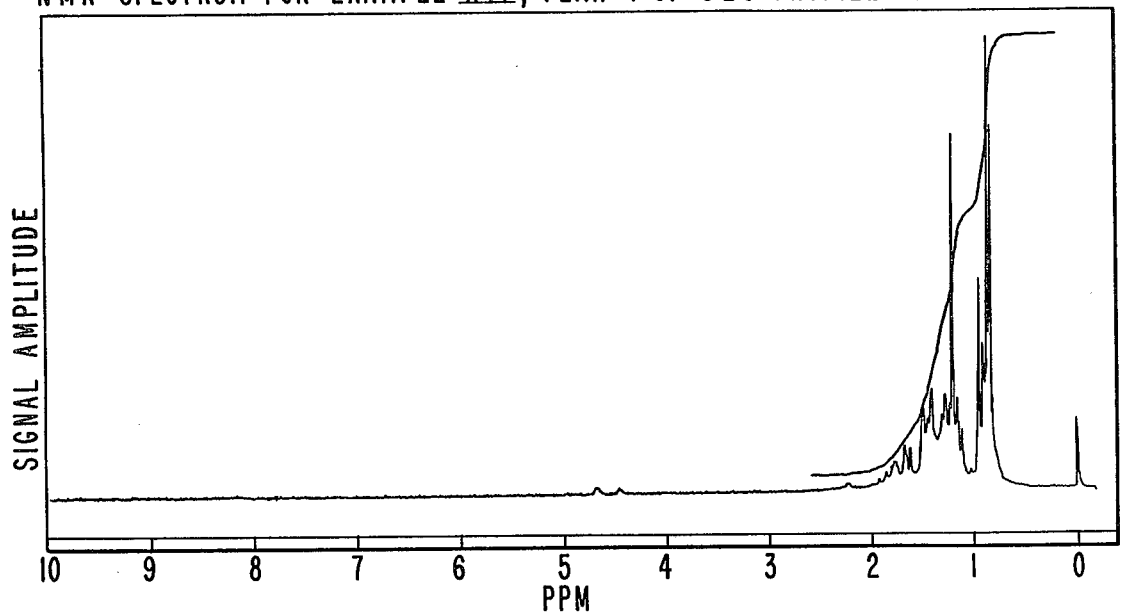

FIG. 68 is the NMR spectrum for Peak 4 of the GLC profile of FIG. 61.

Figure 69:
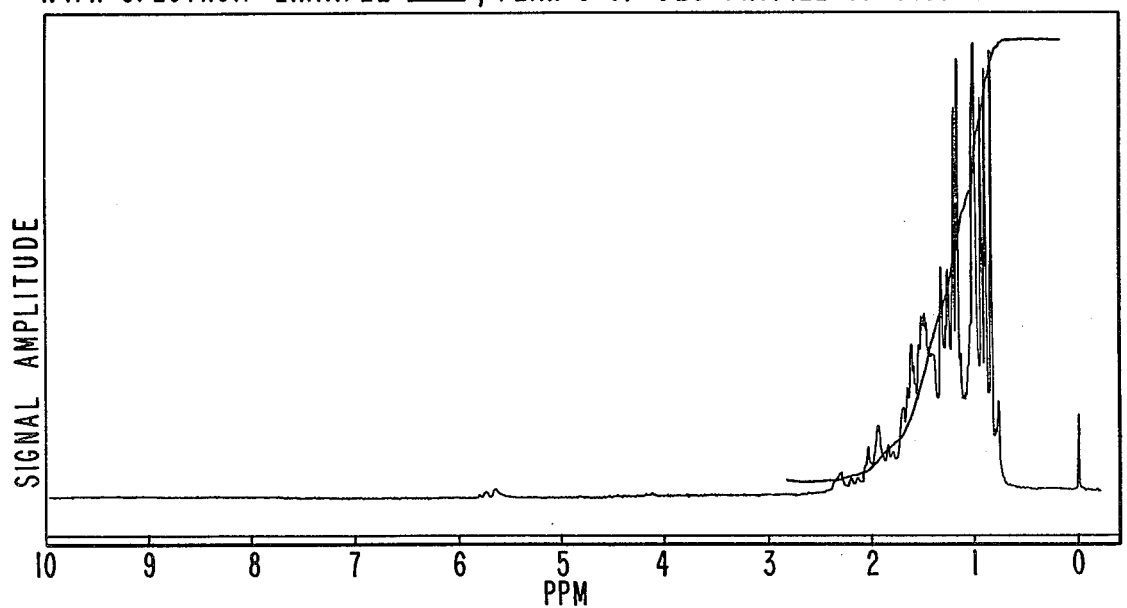

FIG. 69 is the NMR spectrum for Peak 5 of the GLC profile of FIG. 61.

FIG. 70 is the NMR spectrum for Peak 6 of the GLC profile of FIG. 61.

THE INVENTION

It has now been discovered that novel foodstuff, tobacco, smoking tobacco and chewing tobacco flavoring compositions having oriental-like, herbaceous, minty, earthy, woody, natural tobacco-like and cedarwood-like aroma and taste nuances as well as novel perfume compositions, colognes, and perfumed articles (e.g., solid liquid anionic, cationic, nonionic and zwitterionic detergent compositions as well as fabric softener compositions, dryer-added fabric softener articles and cosmetic powders) having intense, long-lasting and pleasant dry woody (cedary, vetiver), thymol-like, camphoraceous, amber, sandalwood-like, fresh, sweaty, fruity, castoreum-like, cedrus atlantica, patchouli-like, labdanum-like, green, fruity, amber, cigar box-like, oriental, cedarwood-like, minty, spicy, floral (rose), vetiver-like, grapefruit oil-like and sweet aromas which become warm and rich on dry-out may be provided by the utilization of one or more tricyclic alcohols, ethers or ester derivatives having the generic structure:

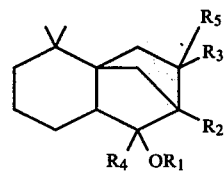

wherein $R_1$ represents hydrogen, methyl or acetyl and wherein $R_2$, $R_3$, $R_4$ and $R_5$ represent the same or different hydrogen, methyl or ethyl.

The novel tricyclic alcohols, ethers and esters of our invention useful as indicated supra, may be produced preferably using the following processes:

(1) First forming a tricyclic ketone having the generic structure:

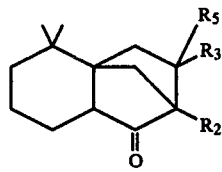

wherein $R_2$, $R_3$ and $R_5$ are the same or different and each represents hydrogen, methyl or ethyl, according to the processes set forth in Application for U.S. Letters Patent Ser. No. 095,149, filed on Nov. 16, 1979 now U.S. Pat. No. 4,250,338 issued on Feb. 10, 1981 then either (2) reducing the tricyclic ketone having the structure:

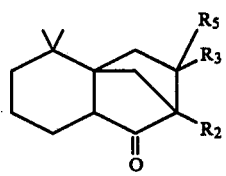

with a suitable reducing agent such as lithium aluminum hydride to form an alcohol defined according to the structure:

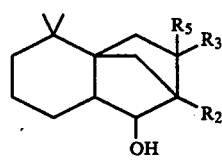

or (3) reacting the ketone having the structure:

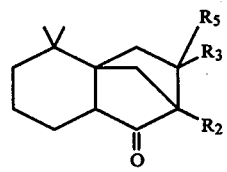

with methyl lithium to form the lithium salt having the structure:

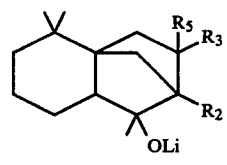

which is then hydrolized to form the alcohol having the structure:

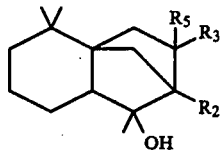

When procedure (2) is carried out wherein the alcohol having the structure:

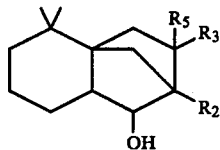

is formed, this alcohol can be used "as is" or it can be reacted with acetic anhydride to form the acetate having the structure:

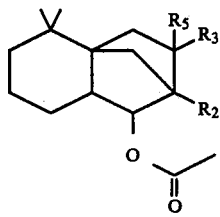

or it can be reacted with sodium hydride to form the sodium alkoxide having the structure:

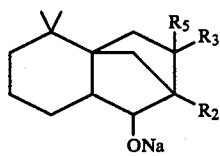

which, in turn, is reacted with a methyl halide such as methyl iodide to form the ether having the structure:

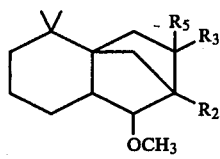

When procedure (3) is used, the ketone having the structure:

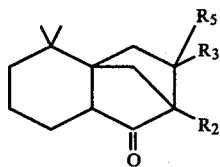

is first reacted with methyl lithium to form the lithium salt or lithium alkoxide having the structure:

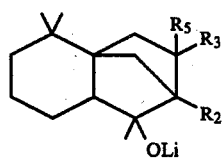

which is then hydrolized in the presence of acid to form the tertiary alcohol having the structure:

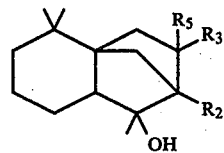

This tertiary alcohol may be reacted with acetic anhydride to form an ester or it may be used "as is" for its organoleptic properties. In addition, the lithium salt having the structure:

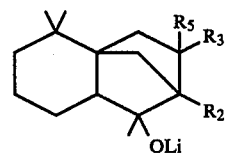

may be reacted with a methyl halide such as methyl iodide or methyl bromide or methyl chloride to form the corresponding methyl ether, the methyl ether of a tertiary alcohol.

In general, the aforementioned reaction sequence wherein the ketone having the structure:

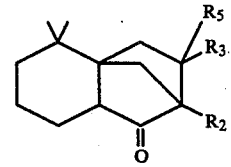

is first reduced and then subsequently the resulting alcohol is either etherified or acylated, the reaction sequence is as follows:

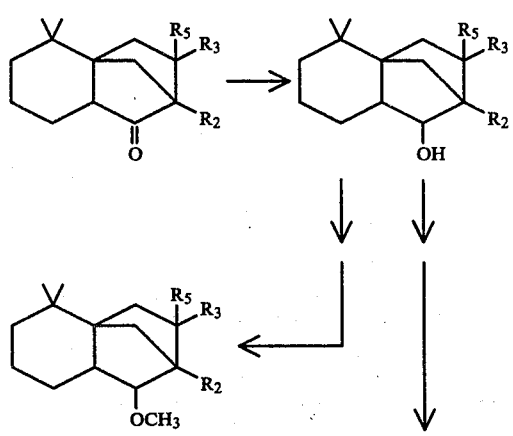

-continued

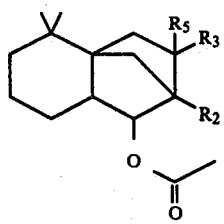

On the other hand, when the tricyclic ketone having the structure:

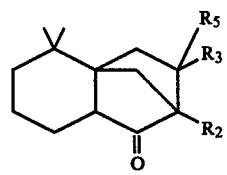

is reacted with the methyl lithium thus forming a lithium alkoxide which is then hyrolized to form an alcohol, the reaction sequence is as follows:

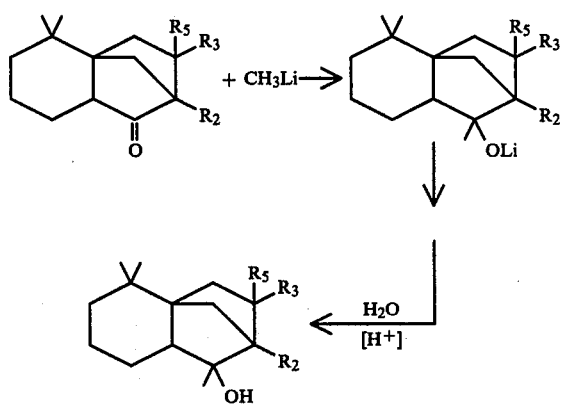

However, where the reaction of a ketone is with an alkyl metal such as alkyl lithium or alkyl sodium or alkyl potassium to form an alkali metal alkoxide, and where this alkali metal alkoxide is either first hydrolized or reacted with a metal halide such as metal iodide, the reaction sequence is as follows:

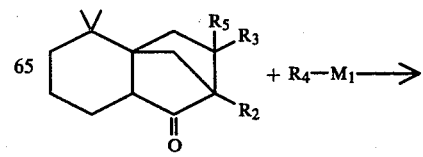

-continued

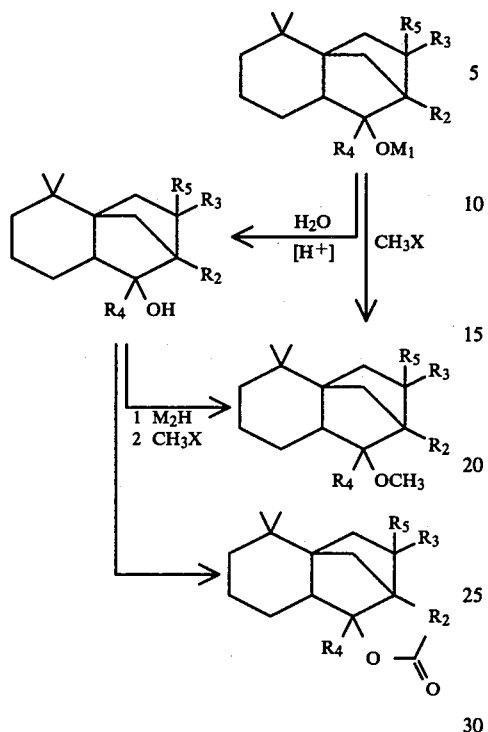

wherein M is an alkali metal which is either lithium, sodium or potassium and X represents chloro, bromo or iodo.

In carrying out the reduction of the tricyclic ketone having the structure:

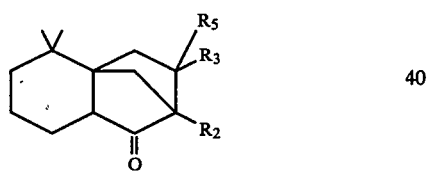

in the presence of a reducing agent such as lithium aluminum hydride to form a tricyclic alcohol having the structure:

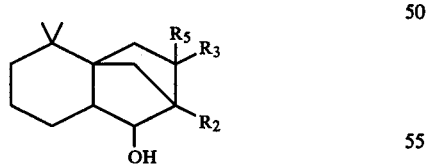

the reaction is preferably carried out in an inert solvent such as tetrahydrofuran or diethylether at reflux temperatures e.g., the boiling point of the solvent at atmospheric pressure. At the end of the reaction, the reaction mass is "worked up" whereby the reaction product is either extracted of impurities (in the event that it is a solid) or the reaction mass is washed and distilled (in the event that the resulting product is a liquid at ambient conditions).

The product having the structure:

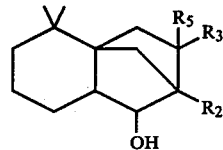

may then either be used "as is" for its organoleptic properties or it may be further reacted whereby an ether is formed having the formula:

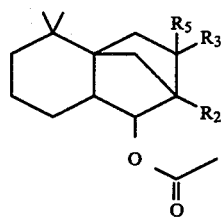

or an ester is formed having the structure:

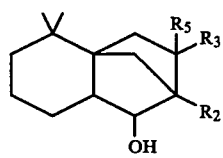

Where an ether is formed, the tricyclic alcohol having the structure:

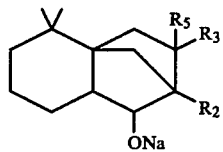

is first reacted with an alkali metal hydride such as sodium hydride or potassium hydride to form the resulting metal salt for example, the sodium metal salt having the generic structure:

This reaction is preferably carried out in an inert solvent such as diethyl ether or tetrahydrofuran at reflux temperatures, e.g., the boiling point of the solvent at atmospheric pressure. At the end of the reaction to form the alkali metal salt of the tricyclic alcohol, the alkali metal salt of the tricyclic alcohol is then reacted with a metal halide, CH₃X where an X is chloro, bromo or iodo. The reaction of the metal halide with the tricyclic alcohol alkali metal salt is exothermic and can be carried out in situ in the presence of the solvent that was originally used for the reaction of the metal hydride with the tricyclic alcohol having the structure:

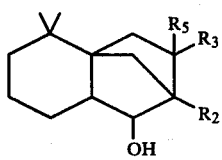

The reaction of the methyl halide with the metal salt of the tricyclic alcohol being exothermic merely need be monitored until the spectra indicate the formation of the ether.

Immediately upon the cessation of the reaction and after the solvent is stripped, the reaction mass may be washed in order to purify it by means of ordinary "work-up" techniques and then the reaction mass is distilled to yield the odor and/or flavor acceptable fraction for use for their respective organoleptic properties.

In carrying out the reaction of the tricyclic alcohol having the structure:

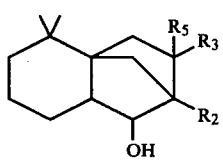

in order to form the acetate having the structure:

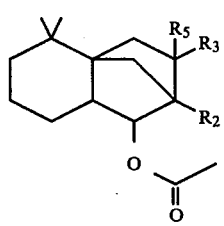

ordinary esterification techniques may be used. Thus, the reaction may be carried out using acetyl chloride or acetic anhydride as the acetylating agent. Preferably, the reaction is carried out in the presence of sodium acetate. The reaction is carried out under reflux conditions using an excess of acylating agent and a catalytic quantity (preferably) of sodium acetate. The reaction is monitored using GLC techniques which are standard in the art and when completed, the reaction mass is worked up in a standard fashion. After the reaction mass is worked up, the solvent is stripped and the reaction mass is distilled. The distillation product fractions are then bulked in a manner appropriate for commercial use of the resulting material in whichever field it is desired. Thus, the bulking of the distillation fractions for tobacco use may be different from the bulking of the fractional distillation fractions if the material is desired for fragrance use.

In each of the foregoing reactions with the exception of the acetylation reaction, the mole ratios of reactants are approximately 1:1. In the acetylation reaction, the mole ratio is preferably in the range of from about 2:1 acetylation agent:tricyclic alcohol up to about 6:1 acetylation agent:tricyclic alcohol. The foregoing reactions encompass the reaction sequence:

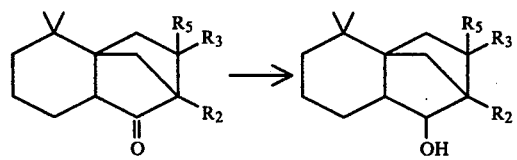

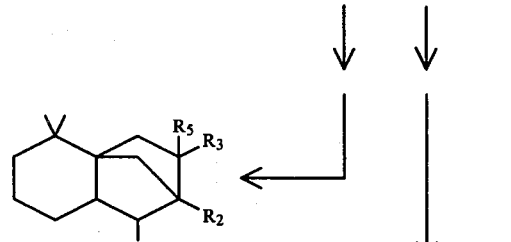

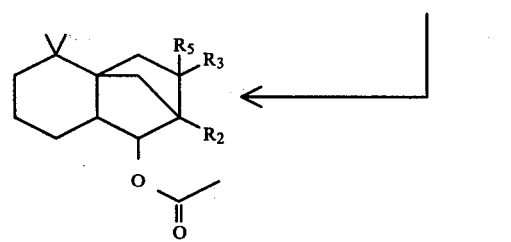

Insofar as the reaction sequence:

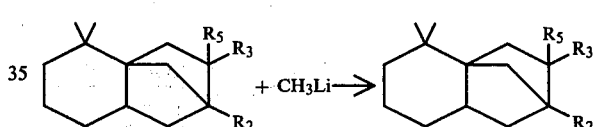

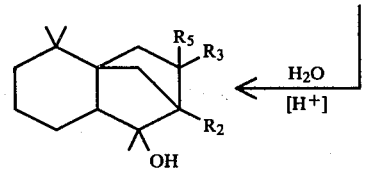

is concerned, the reaction is to take place at reflux conditions in an inert solvent such as diethyl ether or tetrahydrofuran. The mole ratio of methyl lithium:tricyclic ketone having the structure:

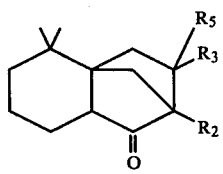

is approximately 1:1 up to 1.5:1 with a slight excess of methyl lithium being preferred.

At the end of the reaction, the excess methyl lithium is neutralized and the reaction mass is hydrolized whereby the lithium salt having the structure:

is converted into the tertiary alcohol having the structure:

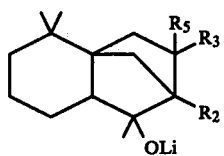

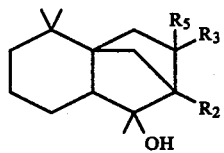

The hydrolysis of the lithium salt of the tricyclic alcohol having the structure:

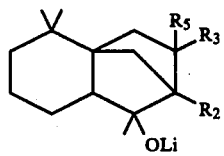

may take place at a pH range of from about 4 up to about 10. Indeed, the hydrolysis may take place in neutral media. At the end of the reaction, the reaction mass is worked up in a routine fashion and the reaction product is distilled yielding a desired group of fractions from a fractional distillation. The various fractions are bulked as desired for their specific organoleptic properties; that is, for use in augmenting or enhancing fragrances, the aroma of perfumed articles, the aromas of colognes, the aroma or taste of smoking tobaccos, chewing tobaccos and foodstuffs.

Examples of the tricyclic alcohols, ethers and esters having the generic structure:

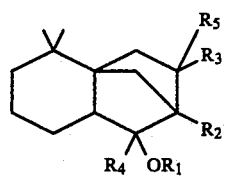

wherein $R_1$ represents hydrogen, ethyl or acetyl and wherein $R_2$, $R_3$, $R_4$ and $R_5$ represent the same or different hydrogen, methyl or ethyl produced according to the processes of our invention and their organoleptic properties are set forth in the following table:

TABLE I

| STRUCTURE | PERFUMERY EVALUATION | FOOD FLAVOR AND CHEWING TOBACCO FLAVOR EVALUATION | SMOKING TOBACCO FLAVOR EVALUATION |
|---|---|---|---|
| Prepared according to Example XI(A). | A dry woody, thymol-like and camphoraceous-like fragrance with long lasting patchouli undertones. | Patchouli-like flavor and aroma. | Patchouli-like flavor and aroma both prior to and on smoking. |
| Prepared according to Example XI(B). | A dry woody (cedary, vetiver), amber-like and sandalwood-like aroma. | An oriental/incense aroma and taste. | An oriental/incense aroma and taste prior to and on smoking causing the Virginia tobacco to have "Turkish tobacco" nuances on smoking. |
| Prepared according to Example XI(C). | A fresh camphoraceous, woody, sweaty and fruity aroma. | An oriental-like aroma and taste. | An oriental aroma and taste prior to and on smoking in the main stream and the side stream causing the Virginia-like tobaccos to be more "Turkish-like". |

TABLE I-continued

| STRUCTURE | PERFUMERY EVALUATION | FOOD FLAVOR AND CHEWING TOBACCO FLAVOR EVALUATION | SMOKING TOBACCO FLAVOR EVALUATION |
|---|---|---|---|
| (structure with OH) Prepared according to Example XII(A). | A dry woody, amber-like, castoreum-like, cedrus atlantica, and patchouli aroma. | | |
| (structure with OCH₃) Prepared according to Example XII(B). | A sweet, woody, patchouli-like labdanum and green aroma. | Oriental aroma and taste. | Oriental aroma and taste both prior to and on smoking in the main stream and the side stream causing Virginia-like tobacco to be more "Turkish-like". |
| (structure with OH) Prepared according to Example XIII(A). | A woody, amber, cedar aroma with green and friuty undertones. | | |
| (structure with OCH₃) Prepared according to Example XIII(B). | A woody, amber, cigar-box-like, sandalwood-like, oriental aroma. | An oriental aroma and taste. | An oriental aroma and taste both prior to and on smoking in the main stream and the side stream causing Virginia-like tobaccos to be more "Turkish-like". |
| (structure with OH) Prepared according to Example XIV(A). | A woody, cedarwood-like and minty aroma profile. | | |
| (structure with OCH₃) Prepared according to Example XIV(B). | A woody, patchouli aroma profile. | An oriental aroma and taste. | An oriental aroma and taste both prior to and on smoking in the main stream and in the side stream causing the Virginia-like tobaccos to be more "Turkish-like". |

TABLE I-continued

| STRUCTURE | PERFUMERY EVALUATION | FOOD FLAVOR AND CHEWING TOBACCO FLAVOR EVALUATION | SMOKING TOBACCO FLAVOR EVALUATION |
| --- | --- | --- | --- |
| (structure with OH) Prepared according to Example XV(A). | A dry woody, spicy, minty, floral (rose) aroma becoming warm and rich on dryout. | An oriental, herbaceous, minty and earthy aroma and taste profile. | An oriental aroma and taste with interesting menthol-like and cooling undertones in both the main stream and the side stream on smoking. The combination of oriental and minty aroma nuances causes smoking tobacco to be "Turkish-like" and at the same time have pleasant cooling nuances. |
| (structure with O-C(=O)-) Prepared according to Example XV(B). | A dry woody, camphoraceous, sweaty, vetiver-like and grapefruit oil-like aroma. | A woody and oriental aroma and taste profile. | A woody, oriental aroma and taste both prior to and on smoking in the main stream and in the side stream. |
| (structure with $OCH_3$) Prepared according to Example XV(C). | An amber, woody, camphoraceous, fruity and sweet aroma profile. | A tobacco-like, woody, oriental and cedarwood-like aroma and taste at 1 ppm. | A natural tobacco-like oriental, cedarwood-like and woody aroma and taste both prior to and on smoking in the main stream and in the side stream. |
| (structure with OH) Prepared according to Example XVI. | A woody, oily, slightly amber aroma profile. | | |

When the tricyclic alcohols, ethers and/or esters of our invention are used separately or taken in combination as food flavor adjuvants, the nature of the co-ingredients included with said tricyclic alcohols, ethers and/or esters in formulating the product composition will also serve to alter the organoleptic characteristics of the ultimate foodstuffs treated therewith. As used herein in regard to flavors, the term "alter" in its various forms means "supplying or imparting flavor character or note to otherwise bland, relatively tasteless substance or augmenting the existing flavor characteristic where a natural flavor is deficient in some regard or supplementing the existing flavor impression to modify its quality, character or taste". As used herein, the term "foodstuff" includes both solid and liquid ingestible materials which usually do but need not have nutritional value. Thus, foodstuffs include meats, gravies, soups, convenience foods, beverages, soy mil, yoghurts and other dairy products, candies, vegetables, cereals, soft drinks, snacks and the like.

The term "enhance" is used herein to mean the intensification of a flavor or aroma characteristic or note without the modification of the quality thereof. Thus, "enhancement" of a flavor or aroma means that the enhancement agent does not add any additional flavor note.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditions, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiarybutyl-4-methyl phenol), propyl gallate and the like, and sequestrants, e.g., citric acid.

Thickener compounds include carriers, binders, protective colloids, suspending agents, emulsifiers, and the like, e.g., agaragar; carrageenan; cellulose and cellulose derivatives such as carboxymethyl cellulose and methyl cellulose; natural and synthetic gums such as gum arabic, gum tragacanth; gelatin, proteinaceous materials, lipids, carbohydrates; starches, pectins, and emulsifiers, e.g., mono-and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starth modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcumin and the like; firming agents such as aluminum sodium sulfate, calcium chloride and calcium gluconate; texturizers; anticaking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acid, e.g., fatty saturated acids, unsaturated acids and amino acids; alcohols, e.g., primary and secondary alcohols; esters; carbonyl compounds, e.g., aldehydes and ketones as well as lactones; cyclic organic materials including benzene derivatives; isocyclics, heterocyclics such as furans particularly 2,5-dimethyl-3-acetyl furan and 2-methyl-2,3-dihydro furan-3-one, pyridines, pyrazines (particularly monoalkyl, dialkyl, trialkyl and tetraalkyl substituted pyrazines) and the like, sulfur-containing materials including thiazoles, disulfides, thiols, sulfides, aldehydes, (for example, 3-phenyl-4-pentenal, 3-phenyl-3-pentenal, 3-phenyl-2-pentenal, 2-phenyl-2-pentenal and 2-phenyl-3-methyl-2-butenal); disulifides and the like; other flavor potentiators such as monosodium glutamate, guanylates, inosinates, natural and synthetic flavorants such as vanillin, ethyl vanillin, diacetyl, phenethyl-2-furoate, maltol, natural gums and the like; spices, herbs, essential oils and extractives including "bitterness principles" such as theobromin, caffein, naringin and other suitable materials creating a bitter effect.

The specific flavoring adjuvant selected for use may be either solid or liquid depending upon the desired physical form of the ultimate product, i.e., foodstuff, whether simulated or natural, and should, in any event, be capable of providing an environment in which the tricyclic alcohols, ethers and/or esters of our invention can be dispersed or admixed to provide a homogeneous medium. In addition, selection of one or more flavoring adjuvants as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of tricyclic alcohols, ethers and/or esters of our invention employed in a particular instance can vary over a relatively wide range whereby to its desired organoleptic effects having reference to the nature of the product are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se or flavoring composition. Thus, the use of insufficient quantities of tricyclic alcohols, ethers and/or esters of our invention will, of course, substantially vitiate any possibility of obtaining the desired results while exess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus and with respect to ultimate food compositions, it has been found that quantities of tricyclic alcohols, ethers and/or esters of our invention ranging from a small but effective amount, e.g., 0.02 parts per million up to about 50 parts per million by weight based on total composition are suitable. Concentrations in excess of the maximum quantity stated are not normally recommended since they fail to provide commensurate enhancement of organoleptic properties. In those cases wherein the tricyclic alcohols, ethers and/or esters of our invention are added to the foodstuff as an integral component of the flavoring composition, it is, of course, essential that the total quantity of flavoring composition employed be sufficient to yield an effective tricyclic alcohols, ethers and/or esters of our invention concentration in the foodstuff product.

Food flavoring compositions prepared in accordance with the present invention preferably contain tricyclic alcohols, ethers and/or esters of our invention in concentrations ranging from about 0.02% up to about 10% by weight based on a total weight of said flavoring composition.

The compositions described herein can be prepared according to conventional techniques well known as typified by cake batters and vegetable juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing tricyclic alcohols, ethers and/or esters of our invention with for example, gum arabic, gum tragacanth, carrageenan and the like and thereafter spraydrying the resultant mixture whereby to obtain the particular solid product. Pre-prepared flavor mixes in powder form, e.g., a red currant mix or a fruit flavored powder obtained by mixing dried solid components, e.g., starch, sugar and the like and tricyclic alcohols, ethers and/or esters of our invention in a dry blender until the requisite degree of uniformity is achieved.

It is presently preferred to combine the tricyclic alcohols, ethers and/or esters of our invention with the following adjuvants:
Ethyl-2-methyl butyrate;
Vanillin;
Butyl valerate;
2,3-Diethyl pyrazine;
Methyl cyclopentenolone;
Benzaldehyde;
Valerian Oil Indian;
Propylene Glycol
8,8-dimethyloctahydro-1,5-methano-1H-inden-1-ol having the structure:

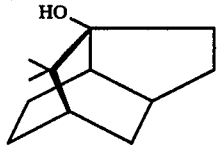

One or more of the tricyclic alcohols, ethers and/or esters of our invention and one or more auxiliary perfume ingredients including, e.g., alcohols, aldehydes, ketones other than the tricyclic alcohols, ethers and/or esters of our invention, terpenic hydrocarbons, nitriles, esters, lactones, natural essential oils and synthetic essential oils, may be admixed so that the combined odors of the individual components produce a pleasant and desired fragrance, particularly in the woody, ambery, leathery, cedarwood-like, sandalwood-like, patchouli-like and vetiver fragrances. Such perfume compositions usually contain (a) the main note or the "bouquet" or foundation stone of the composition; (b) modifiers which round off and accompany the main note; (c) fixatives which include odorous substances which lead a particular note to the perfume throughout all stages of evaporation and substances which retard evaporation; and (d) topnotes which are usually low-boiling fresh-smelling materials.

In perfume compositions, it is the individual components which contribute to their particular olfactory characteristics, however the over-all sensory effect of the perfume composition will be at least the sum total of the effects of each of the ingredients. Thus, one or more tricyclic alcohols, ethers and/or esters of our invention can be used to alter, modify or enhance the aroma characteristics of a perfume composition, for example, by utilizing or moderating the olfactory reaction contributed by another ingredient in the composition.

The amount of tricyclic alcohols, ethers and/or esters of our invention which will be effective in perfume compositions as well as in perfumed articles and colognes depends on many factors, including the other ingredients, their amounts and the effects which are desired. It has been found that perfume compositions containing as little as 0.01% of the tricyclic alcohols, ethers and/or esters or even less (e.g., 0.005%) can be used to augment or enhance or impart dry woody, thymol-like, camphoraceous, cedarwood-like, vetiver-like, amber, sandalwood-like, fresh camphoraceous, sweaty, fruity, castoreum, cedrus atlantica, patchouli-like, labdanum, green, fruity, woody amber, cigar box-like, sandalwood-like, oriental, cedarwood-like, minty, spicy, floral (rose), vetiver-like, and grapefruit oil-like aromas which become warm and rich on dryout to soaps, cosmetics, solid or liquid anionic, cationic, nonionic or zwitterionic detergents, powders, fabric softeners, dryer-added fabric softener articles, hair conditioners and colognes. The amount employed can range up to 70% of the fragrance components and will depend on considerations of cost, nature of the end product, the effect desired on the finished product and the particular fragrance sought.

The tricyclic alcohols, ethers and/or esters of our invention are useful (taken alone or together with other ingredients in perfume compositions) as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of tricyclic alcohols, ethers and/or esters of our invention will suffice to impart intense dry woody, thymol-like, camphoraceous, cedarwood-like, vetiver-like, amber, sandalwood-like, fresh camphoraceous, sweaty, fruity, castoreum, cedrus atlantica, patchouli-like, labdanum, green, fruity, woody-amber, cigar box-like, sandalwood-like, oriental, cedarwood-like, minty, spicy, floral (rose), vetiver-like, and grapefruit oil-like aromas to various formulations such as vetiver formulations. Although, generally, no more than 60% of the tricyclic alcohols, ethers and/or esters of our invention, based on the ultimate end product, is required in the perfume composition, amounts of tricyclic alcohols, ethers and/or esters of our invention of up to 95% may be used in such perfume composition.

When used in perfumed articles such as anionic, cationic, and nonionic detergents, or dryer-added fabric softener articles, cosmetic powders or deodorant compositions, from 0.1% up to 5.0% by weight of the tricyclic alcohols, ethers and/or esters of our invention based on the over-all perfumed article weight may be used in the perfumed articles to impart intense dry woody, thymol-like, camphoraceous, cedarwood-like, vetiver-like, amber, sandalwood-like, fresh camphoraceous, sweaty, fruity, castoreum, cedrus atlantica, patchouli-like, labdanum, green, fruity, woody amber, cigar box-like, sandalwood-like, oriental, cedarwood-like, minty, spicy, floral (rose), vetiver-like, and grapefruit oil-like aromas.

An additional aspect of our invention provides an organoleptically improved smoking tobacco product and additives therefor, as well as methods of making the same which overcome problems heretofore encountered in which specific oriental/incense-like and minty flavor characteristics of natural smoking tobacco (prior to and on smoking in both the main stream and the side stream) as well as cooling effects, are created, enhanced, modified or augmented and may be readily controlled and maintained at the desired uniform level regardless of variations in the tobacco components of the blend.

In carrying out this aspect of our invention, we add to smoking tobacco compositions or a suitable substitute therefor (e.g., dried lettuce leaves), or we add to the wrapper used in producing smoking tobacco articles which surround a cylindrical formed body of smoking tobacco, or we add to the filter which is in intimate contact with both the wrapper and the cylindrical shaped body of tobacco, an aroma and flavor additive containing as an active ingredient one or more of the tricyclic alcohols, ethers and/or esters of our invention.

In addition to the tricyclic alcohols, ethers and/or esters of our invention, other flavoring and aroma additives may be added to the smoking tobacco material or substitute therefor either separately or in mixture with the alcohols, ethers and/or esters as follows:

I. Synthetic Materials:
Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b)-furan
4-Hydroxyhexanoic acid, gamma lactone; and
Polyisoprenoid hydrocarbons defined in Example V of U.S. Pat. No. 3,589,372 issued on June 29, 1971.

II. Natural Oils:
Celery seed oil;
Coffee extract;
Bergamot Oil;
Cocoa extract;
Nutmeg Oil; and
Origanum Oil.

An aroma and flavoring concentrate containing one or more tricyclic alcohols, ethers and/or esters of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. the proportions of flavoring additives may be varied in accordance with taste but insofar as enhancement or the imparting of oriental and/or cooling notes, we have found that satisfactory results are obtained if the proportion by weight of the sum total of the tricyclic alcohol, ether and/or ester derivative(s) to smoking tobacco material is between 50 ppm and 1,500 ppm (0.15%–0.15%). We have further found that satisfactory results are obtained if the proportion by weight of the sum total of tricyclic alcohol, ether and/or ester derivative(s) used to flavoring material is between 1,500 and 15,000 ppm (0.15%–1.5%).

Any convenient method for incorporating the tricyclic alcohol, ether and/or ester derivative(s) into the tobacco product may be employed. Thus, the tricyclic alcohol, ether and/or ester derivative(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the tricyclic alcohol, ether and/or ester derivative(s) taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the tricyclic alcohol, ether and/or ester derivative(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of the compound having the structure:

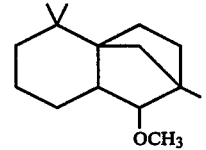

in an amount to provide a tobacco composition containing 800 ppm by weight of the compound having the structure:

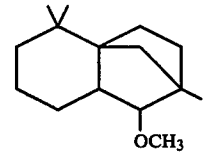

on a dry basis. Thereafter, the alcohol is removed by evaporation and the tobacco is manufactured into cigarettes by the usual techniques. The cigarette, when treated as indicated, has a desired and pleasant aroma which is detectable in the main stream and in the side stream when the cigarette is smoked. The aroma is described as being oriental, natural Turkish tobacco-like with pleasant and long-lasting, cooling nuances.

While our invention is particularly useful in the manufacture of smoking tobacco, such as cigarette tobacco, cigar tobacco and pipe tobacco, other tobacco products, formed from sheeted tobacco dust or fines may also be used. Likewise, the tricyclic alcohols, ethers and/or esters of our invention can be incorporated with materials such as filter tip materials (e.g., cellulose acetate filters wherein sweet, woody, piney and/or cooling effects are desired), seam paste, packaging materials and the like which are used along with tobacco to form a product adapted for smoking. Furthermore, the tricyclic alcohols, ethers and/or esters of our invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

It will thus be apparent that the tricyclic alcohols, ethers and/or esters of our invention can be utilized to alter, modify or enhance sensory properties, particularly organoleptic properties, such as flavor(s) and/or fragrance(s) of a wide variety of consumable materials, such as smoking tobacco, perfumed articles and perfumed compositions in colognes.

The following examples serve to illustrate processes for specifically producing the tricyclic alcohols, ethers and/or esters of our invention and processes for utilizing said tricyclic alcohols, ethers and/or esters of our invention for their organoleptic properties.

All parts and percentages given herein are by weight unless otherwise specified.

EXAMPLES I-X

The following examples set forth specific embodiments of the reaction scheme:

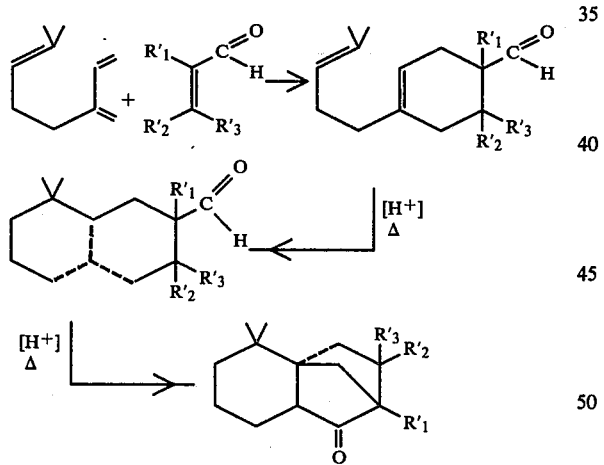

wherein $R_1'$, $R_2'$ and $R_3'$ are each the same or different and each represents hydrogen or lower alkyl, and one of the dashed lines represents a carbon-carbon double bond and each of the other dashed lines represent carbon-carbon single bonds.

The reactions can also be carried out according to the following reaction scheme:

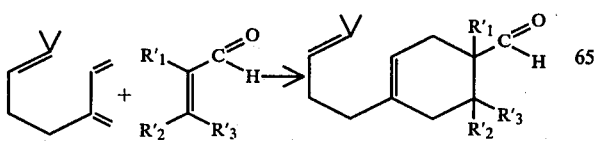

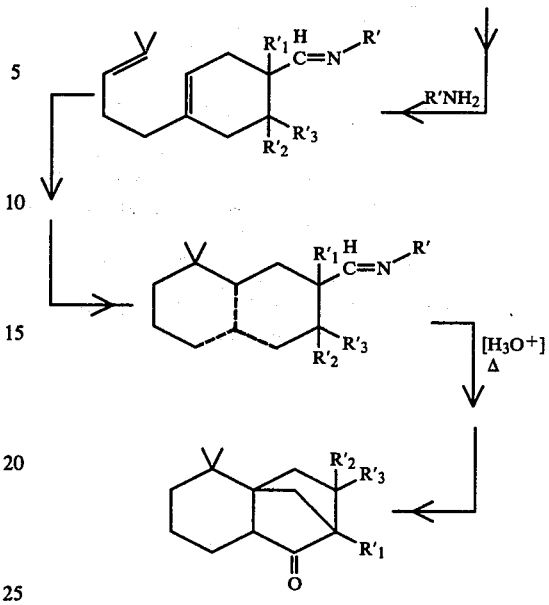

EXAMPLE I

PREPARATION OF A MIXTURE OF 1,2,3,4-TETRAHYDRO-8,8-DIMETHYL-2-TETRALINCARBOXALDEHYDE and HEXAHYDRO-5,5-DIMETHYL-2H-2,4-a-METHANONAPHTHALENE-1(5H)-ONE Reaction:

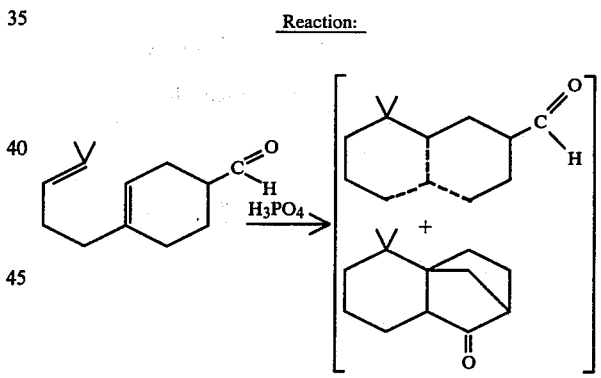

1200 grams of Myrac Aldehyde ® (trademark of the Givaudan Company of Delawanna, N.J.) (4-(4-methyl-3-pentenyl)-3-cyclohexenecarboxaldehyde) and is added dropwise with stirring at 45° C. over a 4 hour period to a mixture of 600 grams of toluene and 1200 grams of 85% phosphoric acid. At the end of the addition the reaction mass is stirred for an additional 30 minutes and then poured into 5 liters of water. The mass is stirred and the organic layer is separated and further washed twice with 2 liters of saturated salt solution. The pH during the second wash is adjusted to pH8 with sodium carbonate. The organic layer is distilled through a short column to afford 1009 grams of crude product. Fractional redistillation through a 1½"×12" Coodloe packed column affords 911 grams of purified product (b.p. 94° C., 3 mm). GLC analysis (200° C., isothermal, 10% SE-30 packed column) indicates a composition of 95% 8,8-dimethyl-2-tetral incarboxaldehyde and 5% hexahydro-5,5-dimethyl-2H-2,4-a-methanonaphthalene-1(5H)-one.

Figure 1:
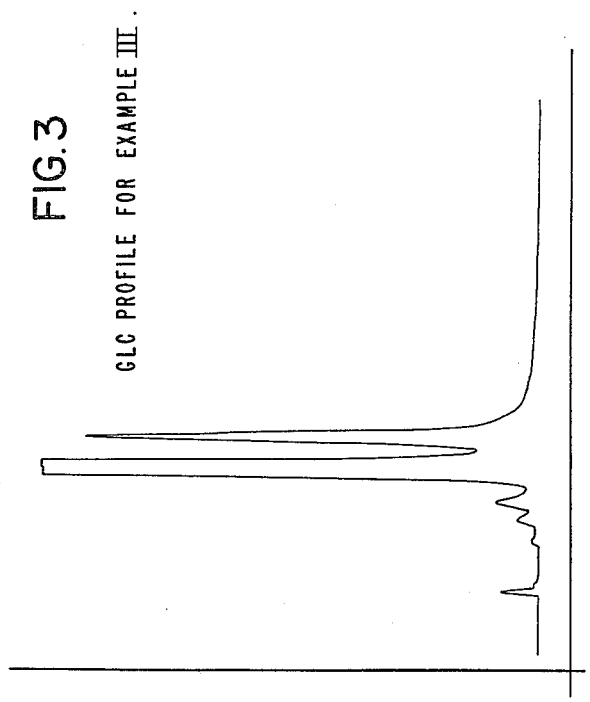
FIG. 1 represents the NMR spectrum for the tricyclic ketone compound having the structure.

FIG. 1 shows the nmr spectrum of hexahydro-5,5-dimethyl-2H-2,4-a-methanonaphthalene-1(5H)-one.

FIG. 2 shows the IR spectrum of hexahydro-5,5-dimethyl-2H-2,4-a-methanonaphthalene-1(5H)-one.

EXAMPLE II

PREPARATION OF A MIXTURE OF 1,2,3,4-TETRAHYDRO-8,8-DIMETHYL-2-TETRALINCARBOXALDEHYDE and HEXAHYDRO-5,5-DIMETHYL-2H-2,4-a-METHANONAPHTHALENE-1(5H)-ONE Reaction:

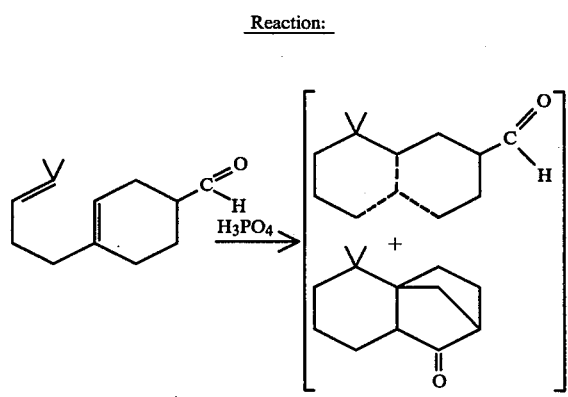

A mixture of 31.2 Kg of 85% phosphoric acid and 15.6 Kg of toluene are charged to a glass lined 50 gallon reactor and heated to 40° C. Myrac Aldehyde ® (31.4 Kg) is added with stirring over a four hour period at 40° C. After stirring the mass at 40° C. for 15 minutes, it is poured with stirring into a 100 gallon glass-lined reactor containing 292 Kg of 15% salt solution. The layers are separated with heat and the organic phase is washed with salt water, 5% caustic solution, and salt water, respectively. The toluene is distilled from the organic mass at reduced pressure 50–100 mm Hg. 150 grams of triethylamine, 75 grams of IONOL ® (a registered trademark of the Shell Chemical Company; butylated hydroxy toluene), and 75 grams of PRIMOL ® (a registered trademark identifying a hydrocarbon mineral oil produced by Exxon Incorporation of Linden, N.J.) are added to the mass. Quick distillation through a short column affords 22.2 Kg of crude product. Fractional redistillation through a 3"×24" Goodloe packed column affords 20.6 Kg of product (b.p. 94° C., 3 mm.) GLC analysis (100°–200°, 8°/min., ¼"×8' 10% Carbowax packed column) indicates 96% 1,2,3,4-tetrahydro-8,8-dimethyl-2-tetralincarboxaldehydes and 4% hexahydro-5,5-dimethyl-2H-2,4-a-methanonaphthalene-1(5H)-one.

EXAMPLE III

PREPARATION OF HEXAHYDRO-5,5-DIMETHYL-2H-2,4-a-METHANONAPHTHALENE-1(5H)-ONE AND A MIXTURE CONSISTING OF 1,2,3,4-TETRAHYDRO-8,8-DIMETHYL-2-TETRALINCARBOXALDEHYDE and HEXAHYDRO-5,5-DIMETHYL-2H-2,4-a-METHANONAPHTHALENE-1(5H)-ONE Reaction:

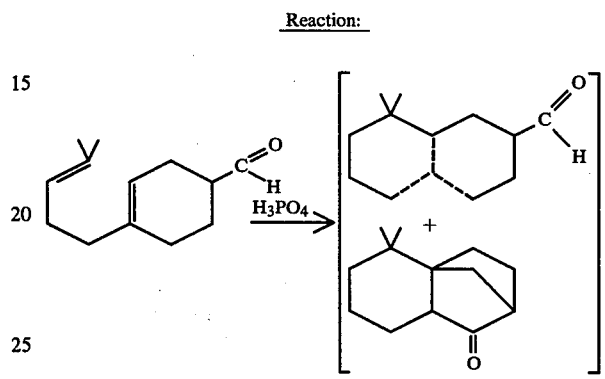

A mixture of 30.9 Kg of 85% phosphoric acid and 15.5 Kg of toluene is charged to a glass lined 50 gallon reactor and heated to 60° C. Myrac Aldehyde ® (30.9 Kg) is added with stirring over a 4 hour period. The reaction mass is processed as in Example II. Distillation through a 3"×24" Goodloe packed column affords 25 Kg of product consisting overall of 75% 1,2,3,4-tetrahydro-8,8-dimethyltetralin and 25% of hexahydro-5,5-dimethyl-2H-2,4-a-methanonaphthalene-1(5H)-one. Refractionation using a reflux to take off ratio of 9:1 affords decahydro-hexahydro-5,5-dimethyl-2H-2,4-a-methanonaphthalene-1(5H)-one.

FIG. 3 represents the GLC trace of the crude reaction mixture, after removal of toluene and before distillation (220° C. isothermal, ¼"×8' 10% Carbowax packed column).

EXAMPLE IV

PREPARATION OF 1,6-DIMETHYL-4-(4-METHYL-3-PENTENYL)-3-CYCLOHEXENE-1-CARBOXALDEHYDE

Reaction:

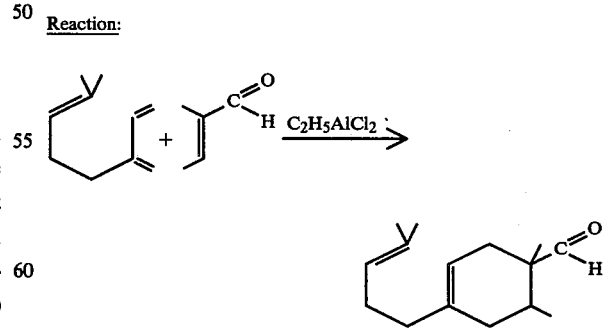

A 3-neck reaction vessel is charged with 100 ml benzene and 50 grams of 25% ethyl aluminum dichloride in benzene. A solution containing 320 grams myrcene (85% pure), 170 grams 2-methyl-2-butenal, and 200 ml benzene is fed in at 40°–50° C. over a 1 hour period. The temperature is then raised to 60° C. and held there for ½ hour. An additional 10 grams ethyl aluminum dichloride solution mixed with 20 ml benzene is added and heating is continued for an additional ½ hour. The mixture is then cooled, water is added and the layers are separated. The organic layer is washed with water and distilled without fractionation to free the material of residue. Redistillation through an 18" Goodloe packed column provides 199 grams of 1,6-dimethyl-4-(4-methyl-3-pentenyl)-3-cyclohexene-1-carboxaldehyde (b.p. 105° C., 0.9 mm).

FIG. 4 represents the nmr spectrum of 1,6-dimethyl-4-(4-methyl-3-pentenyl)-3-cyclohexene-1-carboxaldehyde.

FIG. 5 represents the IR spectrum of 1,6-dimethyl-4-(4-methyl-3-pentenyl)-3-cyclohexene-1-carboxaldehyde.

EXAMPLE V

PREPARATION OF 1,2,3,4-TETRAHYDRO-2,3,8,8-TETRAMETHYL-2-TETRALINCARBOXALDEHYDE

Reaction:

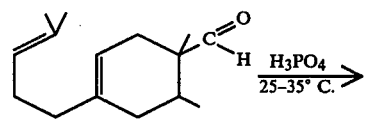

A 1-liter flask equipped with thermometer, mechanical stirrer and addition funnel is charged with 197 grams of 85% phosphoric acid (Mallinkrodt) and 49 grams toluene. The mixture is stirred at 25°-35° C. as 197 grams of the aldehyde as prepared in Example IV is added over 35 minutes. The mixture is then stirred for 5 hours at that temperature range at which time complete reaction is indicated by GLC (Carbowax column). Cooling is applied and 250 ml water is added. The resulting mixture is extracted twice with 500 ml portions of ether. The extracts are washed with 10% sodium hydroxide solution and then with water. The organic solution is dried over sodium sulfate and distilled to free the product from residue. The resulting oil is then fractionally distilled through a 5 ft. Vigreux column to give 92 grams of 1,2,3,4-tetrahydro-2,3,8,8-tetramethyl-2-tetralincarboxaldehyde (b.p. 113°-115° C., 2 mm).

FIG. 6 represents the nmr spectrum of 1,2,3,4-tetrahydro-2,3,8,8-tetramethyl-2-tetralincarboxaldehyde.

FIG. 7 represents the IR spectrum of 1,2,3,4-tetrahydro-2,3,8,8-tetramethyl-2-tetralincarboxaldehyde.

FIG. 8 represents the GLC trace of the tetrahydro-2,3,8,8-tetramethyl-2-tetralincarboxaldehyde isomers (100°-220° C., 8°/min., ¼"×10' 10% Carbowax packed column).

EXAMPLE VI

PREPARATION OF HEXAHYDRO-1,2,5,5-TETRAMETHYL-2H-2,4,-a-METHANONAPHTHALENE-1(5H)-ONE

Reaction:

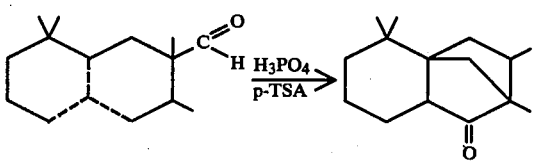

A 500 ml reaction flask is charged with 107 grams toluene, 107 grams 85% phosphoric acid, and 107 grams of 1,2,3,4-tetrahydro-2,3,8,8-tetramethyl-2-tetralincarboxaldehyde. The mixture is heated at reflux for 1.5 hours at which time 1.0 grams p-toluenesulfonic acid is added and reflux is continued for an additional 8.5 hours. The mixture is cooled, diluted with water, and 200 ml ether is added. The layers are separated and the organic layer is washed with water, 10% sodium bicarbonate, and again with water. After drying over magnesium sulfate the solvent is evaporated and the remaining material is distilled without fractionation. The obtained distillate is then fractionally distilled through a 5 foot Vigreux column to give 88 grams of product, b.p. 104°-109° C. (1.0-1.9 mm) consisting of 5% starting material and 95% hexahydro-1,2,5,5-tetramethyl-2H-2,4-a-methanonaphthalene-1(5H)-one.

FIG. 9 represents the nmr spectrum of hexahydro-1,2,5,5-tetramethyl-2H-2,4-a-methanonaphthalene-1(5H)-one.

FIG. 10 represents the I spectrum of hexahydro-1,2,5,5-tetramethyl-2H-2,4-a-methanonaphthalene-1(5H)-one.

EXAMPLE VII

PREPARATION OF HEXAHYDRO-1,5,5-TRIMETHYL-2H-2,4-a-METHANONAPHTHALENE-1(5H)-ONE

Reaction:

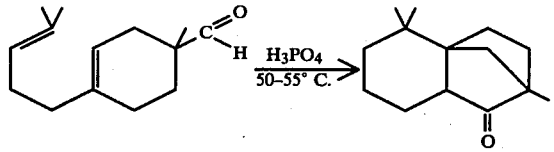

1-Methyl-4-(4-methyl-3-penten-1-yl)-3-cyclohexen-1-carboxaldehyde containing approximately 30% 1-methyl-3-(4-methyl-3-penten-1-yl)-3-cyclohexen-1-carboxaldehyde (206 grams) is added in 35 minutes with good agitation to a mixture of toluene (200 ml) and 85% phosphoric acid (150 grams) at 50°-55° C. The mixture is stirred for 27 hours at 75°-85° C. The reaction mass is then washed with 1250 grams of 5% salt solution, and the aqueous layer is extracted with 100 mls of toluene. The combined organic phases are washed successively with 10% sodium carbonate solution and saturated salt solution. Distillation affords 37 grams of hexahydro-1,5,5-trimethyl-2H-2,4-a-methanonaphthalene-1(5H)-one.

FIG. 11 represents the nmr spectrum of hexahydro-1,5,5-trimethyl-2H-2,4-a-methanonaphthalene-1(5H)-one.

FIG. 12 represents the $^{13}C$ nmr spectrum of hexahydro-1,5,5-trimethyl-2H-2,4-a-methanonaphthalene-1(5H)-one.

EXAMPLE VIII

PREPARATION OF HEXAHYDRO-2,5,5-TRIMETHYL-2H-2,4-a-METHANONAPHTHALENE-1(5H)-ONE

Reaction:

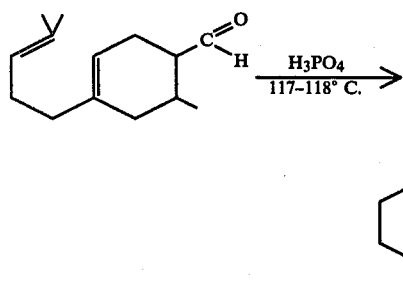

A mixture of 300 ml of toluene and 150 grams of 85% phosphoric acid is stirred at reflux while 618 grams of 6-methyl-4-(4-methyl-3-penten-1-yl)-3-cyclohexen-1-carboxaldehyde are added over a period of 30 minutes. The mixture is stirred for 11 hours and 117°–118° C. and then some of the toluene is distilled off to raise the reaction temperature to 135°–137° C. and the mixture is stirred for an additional 2 hours. The mixture is then washed well and fractionally distilled through a 1½"×12" Goodloe packed column to give 160 grams of material which is shown by GLC analysis (220° C., isothermal, ¼"×10′ 10% Carbowax packed column) to be greater than 92% hexahydro-2,5,5-trimethyl-2H-2,4-a-methanonaphthalene-1(5H)-one.

FIG. 13 represents the nmr spectrum of hexahydro-2,5,5-trimethyl-2H-2,4-a-methanonaphthalene-1(5H)-ONE.

FIG. 14 represents the IR spectrum of hexahydro-2,5,5-trimethyl-2H-2,4-a-methanonaphthalene-1(5H)-one.

EXAMPLE IX

PREPARATION OF HEXAHYDRO-1,5,5-TRIMETHYL-2H-2,4-a-METHANONAPHTHALENE-1(5H)-ONE

Reaction:

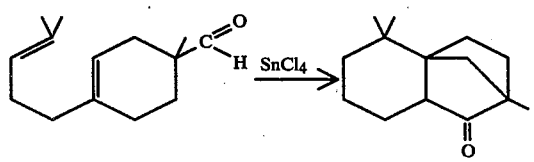

To a solution of 1-methyl-4-(4-methyl-3-penten-1-yl)-3-cyclohexene-1-carboxaldehyde (500 grams, 2.4 mol) and toluene (500 ml) is added stannic chloride (63 grams, 0.24 mol) dropwise at room temperature over a 10 minute period. The mass is heated to gentle reflux for 30 minutes, cooled to room temperature and stirred for an additional two hours. When the reaction is complete, the mass is poured into 1000 ml of 5% HCl solution and washed consecutively with 1000 ml of 5% aqueous sodium carbonate and 1000 ml of water. The organic layer is isolated and solvent removed under reduced pressure. The remaining mass is distilled through a 12"×2" Goodloe packed column to afford a total of 209 grams of material, of which 73 grams is the desired product (b.p. 93°–94° C., 1.8 mm).

EXAMPLE X

PREPARATION OF HEXAHYDRO-1,5,5-TRIMETHYL-2-ETHYL-2H-2,4-2-METHANONAPHTHALENE-1(5H)-ONE

EXAMPLE X(A)

Reaction:

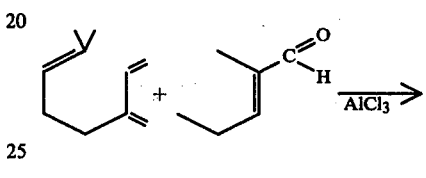

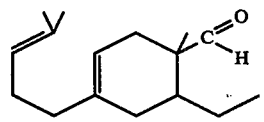

Into a 3 liter reaction flask equipped with stirrer, condenser, thermometer and dropping funnel is placed 500 cc of toluene and 294.0 grams (3.0 moles) of 2-methyl-2-pentenal. Slowly, 40.0 grams (0.3 moles) of aluminum chloride is added to the reaction mass. Dropwise over a period of 30 minutes while maintaining the reaction temperature at 20°–30° C. is added 3.0 moles (582.8 grams) of myrcene (70% pure). The reaction mass is stirred at 25°–30° C. for a period of 3.5 hours. At the end of the 3.5 hours, 500 cc of water is added to the reaction mass followed by 200 cc of 20% aqueous hydrochloric acid (purpose to break the emulsion). The resulting organic and inorganic layers are separated and the organic layer is stripped of solvent and distilled, yielding the following fractions (12 inch stone column):

| Fraction Number | Vapor Temp. °C. | Liquid Temp. °C. | Head Vac. mm. Hg | Weight of Fraction |
|---|---|---|---|---|
| 1 | 80/100 | 140/150 | 1.7/1.2 | 30.0 |
| 2 | 125 | 155 | 1.2 | 14.0 |
| 3 | 140 | 160 | 1.6 | 40.0 |
| 4 | 145 | 165 | 1.6 | 79.0 |
| 5 | 145 | 195 | 2.0 | 160.0 |
| 6 | 155 | 240 | 2.5 | 125.0 |

FIG. 15 represents the GLC profile for the reaction product of Example X(A) containing the compound having the structure:

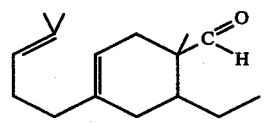

FIG. 16 is the mass spectrum for the compound having the structure:

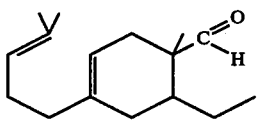

produced according to Example X(A).

FIG. 17 is the NMR spectrum for the compound having the structure:

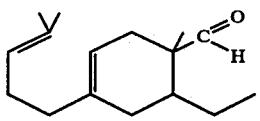

produced according to Example X(A), Fraction 5 of the distillation product.

FIG. 18 is the infra-red spectrum for Fraction 5 of the distillation product of the reaction product of Example X(A) having the structure:

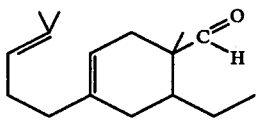

EXAMPLE X(B)

Reaction:

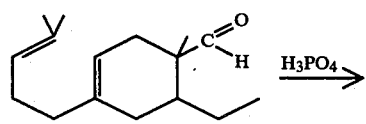

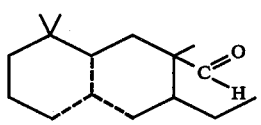

Into a 2 liter reaction vessel equipped with stirrer, condenser, thermometer and dropping funnel is placed 160.0 grams (1.74 moles) of toluene. The aldehyde produced in Example X(a) (400 grams/1.74 moles) is then added to the toluene. Dropwise over a period of 30 minutes 200 grams (1.74 moles) of phosphoric acid is added. The reaction mass is stirred for 8 hours. At the end of the 8 hour period 400 cc of water is added to the reaction mass and the organic and inorganic layers are separated. The organic layer is stripped of solvent and distilled on a 12 inch stone column yielding the following fractions:

| Fraction Number | Vapor Temp. °C. | Liquid Temp. °C. | Head Vac. mm. Hg | Weight of Fraction |
|---|---|---|---|---|
| 1 | 70/110 | 130/135 | 0.9/0.9 | 17.0 |
| 2 | 125 | 145 | 0.9 | 119.0 |
| 3 | 130 | 150 | 0.9 | 112.0 |

| Fraction Number | Vapor Temp. °C. | Liquid Temp. °C. | Head Vac. mm. Hg | Weight of Fraction |
|---|---|---|---|---|
| 4 | 130 | 210 | 0.9 | 100.0 |

FIG. 19 is the NMR spectrum for the product having the structure:

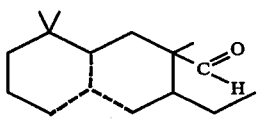

produced according to Example X(B).

EXAMPLE X(C)

Reaction:

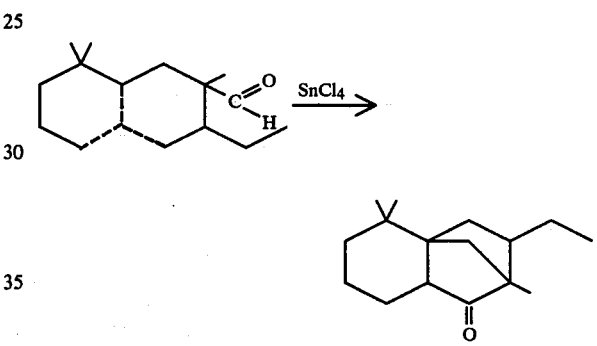

Into a 1000 cc reaction flask equipped with stirrer, condenser, thermometer and dropping funnel is placed 200 cc of toluene and 331.0 grams (1.396 moles) of the aldehyde prepared according to Example X(B). Dropwise over a period of 30 minutes, 36.29 grams (0.1396 moles) of concentrated stannic chloride solution is added while maintaining the reaction temperature at 30° C. The reaction mass is then heated for a period of 3 hours at 50° C. The reaction mass is then added to 250 cc of water and the resulting organic and inorganic layers are separated. The organic layer is washed with two 200 cc volumes of water and the organic organic layer is then stripped of solvent and distilled on a 12 inch stone column yielding the following fractions:

| Fraction Number | Vapor Temp. °C. | Liquid Temp. °C. | Head Vac. mm. Hg | Weight of Fraction |
|---|---|---|---|---|
| 1 | 120/125 | 140/155 | 1.0/1.0 | 41.0 |
| 2 | 135 | 160 | 1.0 | 110.0 |
| 3 | 155 | 220 | 1.0 | 85.0 |

FIG. 20 is the mass spectrum for Fraction 2 of the distillation product of the reaction product of Example X(C) having the structure:

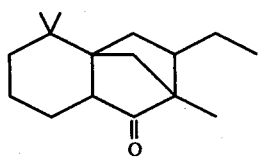

FIG. 21 is the NMR spectrum for Fraction 2 of the distillation product of the reaction product of Example X(C) having the structure:

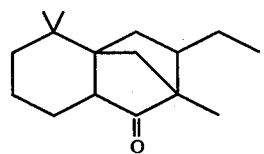

FIG. 22 is the infra-red spectrum for Fraction 2 of the distillation product of the reaction product of Example X(C) having the structure:

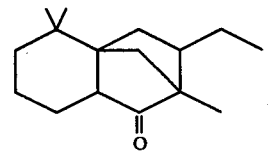

EXAMPLES XI–XVI

The following examples set forth specific embodiments of the reaction schemes:

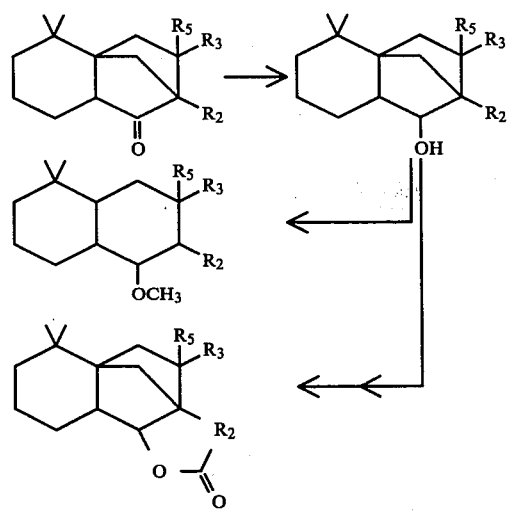

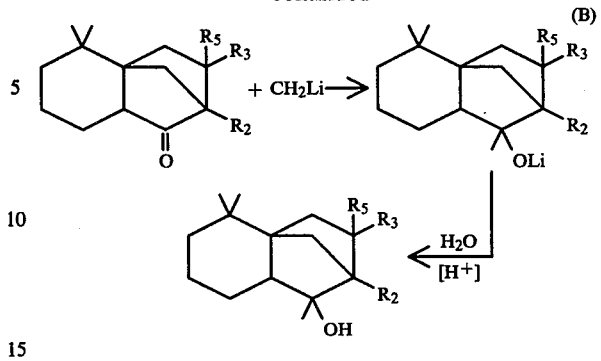

wherein $R_2$, $R_3$ and $R_5$ represent the same or different hydrogen, methyl or ethyl.

EXAMPLE XI

PREPARATION OF HEXAHYDRO-5,5-DIMETHYL-2H-2,4A-METHANONAPHTHALENE-1-OL,METHYLETHER AND ACETATE

EXAMPLE XI(A)

Reaction:

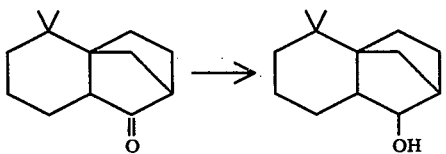

Into a 500 ml reaction flask equipped with reflux condenser, addition funnel and thermometer is placed 250 ml anhydrous tetrahydrofuran. 9.5 grams (0.25 moles) of lithium aluminum hydride is then added to the tetrahydrofuran. Over a period of 23 minutes while maintaining the reaction temperature of 35° C., 96 grams (0.5 moles) of the ketone produced in Examples I, II or III is added to the reaction mass. The reaction mass is then heated to a temperature of 67° C. and maintained at 67°–68° C. for a period of 2 hours. At the end of the 2 hour reaction, the reaction mass is cooled to room temperature and 9.5 ml water followed by 9.5 grams of 15% aqueous NaOH followed by 28 ml water are added. The resulting mixture is filtered and the aqueous layer is separated from the organic layer. The aqueous layer is extracted with ether and the ether extract is combined with the organic layer. A solid precipitates therefrom and is filtered. The resulting solid is dried and analyzed by means of NMR, IR and mass spectral analysis to be the compound having the structure:

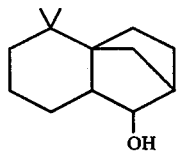

FIG. 23 is the GLC profile for the reaction product of Example XI(A) containing the compound having the structure:

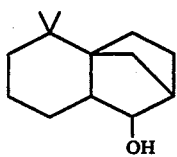

FIG. 24 is the mass spectrum of the reaction product of Example XI(A) containing the compound having the structure:

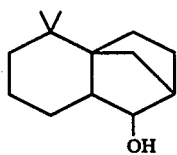

FIG. 25 is the NMR spectrum for the reaction product of Example XI(A) containing the compound having the structure:

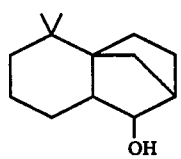

EXAMPLE XI(B)

Reaction:

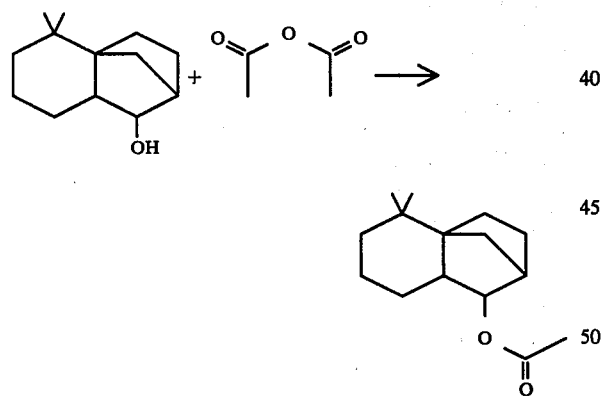

Into a 250 ml reaction flask equipped with reflux condenser, thermometer and nitrogen blanket apparatus is placed 22 grams (0.11 moles) of the tricyclic alcohol prepared according to Example XI(A), 50 ml of acetic anhydride (0.5 moles) and 0.5 grams of sodium acetate. The reaction mass is heated to reflux, 130° C. and maintained at reflux for a period of 2 hours. At the end of the 2 hour period, 25 ml of water is added over a period of 30 minutes dropwise. The reaction mass is continued to be maintained at a temperature of 100° C. during the addition of the water. The resulting product is then poured into a separatory funnel and extracted with methylene chloride. The organic layer is then washed with a saturated sodium bicarbonate solution. The resulting organic solution is stripped of solvent and now weighs 47.7 grams. The resulting material is then distilled at a vapor temperature of 90° C. and a pressure of 0.75 mm Hg yielding 22.3 grams of product having the structure:

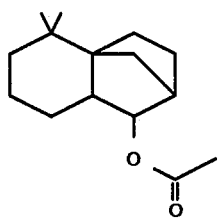

as confirmed by NMR, IR and mass spectral analysis.

FIG. 26 is the GLC profile fo the reaction product of Example XI(B) containing the compound having the structure:

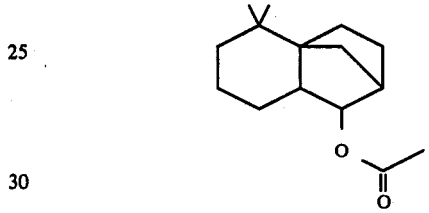

FIG. 27 is the mass spectrum for the reaction product of Example XI(B) containing the compound having the structure:

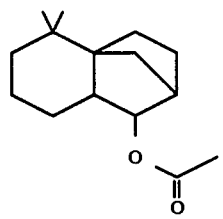

(bulked Fractions 1 and 2).

FIG. 28 is the NMR spectrum for bulked Fractions 1 and 2 of the distillation product of the reaction product of Example XI(B) containing the compound having the structure:

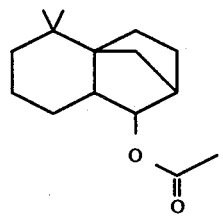

FIG. 29 is the infra-red spectrum for bulked Fractions 1 and 2 of the distillation product of the reaction product of Example XI(B) containing the compound having the structure:

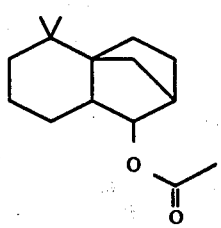

EXAMPLE XI(C)

Reaction:

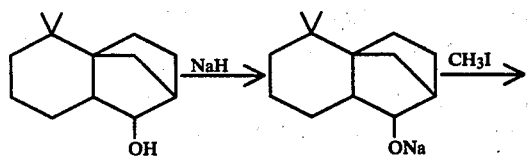

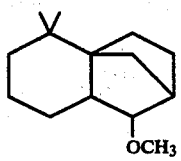

Into a 500 cc reaction flask equipped with stirrer, condenser, thermometer, dropping funnel and nitrogen blanket apparatus is placed 50 cc of anhydrous tetrahydrofuran. Into the tetrahydrofuran is added 8.16 grams (0.17 moles) of 50% sodium hydride. The tricyclic alcohol (33.0 grams; 0.171 moles) produced according to Example XI(A) is dissolved in 200 cc of tetrahydrofuran. The resulting tetrahydrofurantricyclic alcohol is then added dropwise over a 10 minute period to the reaction mass. After addition, the reaction mass is stirred at room temperature for a period of 2 hours. Infra-red analysis indicates that no starting material remains.

At this point, over a 10 minute period with cooling, 24.0 grams (0.17 moles) of iodomethane is added to the reaction mass.

The cooling apparatus is removed and the reaction mass is stirred at room temperature for an additional 1.5 hours. GLC sampling indicates reaction completion at this point. 50 cc of water is then added dropwise and the resulting reaction mass is extracted with two 100 ml portions of diethylether. The reaction mass is stripped of solvent and distilled yielding the following fractions:

| Fraction Number | Vapor Temp. °C. | Liquid Temp. °C. | Head Vac. mm. Hg | Weight of Fraction |
|---|---|---|---|---|
| 1 | 99/100 | 120/125 | 1.0/1.0 | 1.5 |
| 2 | 100 | 125 | 1.0 | 7.0 |
| 3 | 100 | 128 | 1.0 | 3.0 |
| 4 | 102 | 160 | 1.6 | 13.0 |
| 5 | 102 | 220 | 1.9 | 3.0 |
| 6 | 150 | 245 | 2.5 | 5.0 |

FIG. 30 is the mass spectrum for Fraction 3 of the distillation product of the reaction product of Example XI(C) containing the compound having the structure:

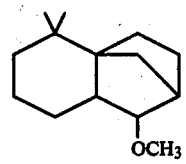

FIG. 31 is the NMR spectrum for Fraction 3 of the distillation product of the reaction product of Example XI(C) containing the compound having the structure:

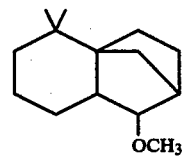

FIG. 32 is the infra-red spectrum for Fraction 3 of the distillation product of the reaction product of Example XI(C) containing the compound having the structure:

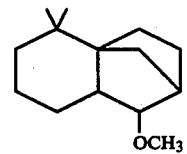

EXAMPLE XII

PREPARATION OF OCTAHYDRO-3,5,5-TRIMETHYL-2H-2,4A-METHANONAPHTHALENE-1-OL

EXAMPLE XII(A)

Reaction:

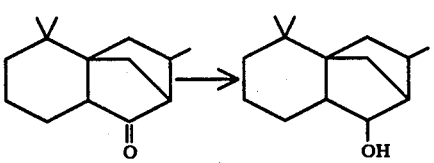

Into a 500 cc reaction flask equipped with stirrer, condenser, thermometer, dropping funnel and nitrogen blanket apparatus is placed 150 cc anhydrous tetrahydrofuran. 15.8 grams (0.42 moles) of 95% lithium aluminum hydride is then added to the tetrahydrofuran. Dropwise over a period of 2 hours while maintaining the reaction mass at 25°-30° C., the tricyclic ketone prepared according to Example VIII is added to the reaction mass. At the end of the 2 hour period, infra-red analysis indicates that the reaction is complete. The reaction mass is hydrolized with 200 cc of water added dropwise with cooling. The resulting organic phase is separated from the aqueous phase and the organic phase is distilled yielding the following fractions:

| Fraction Number | Vapor Temp. °C. | Liquid Temp. °C. | Head Vac. mm. Hg | Weight of Fraction |
|---|---|---|---|---|
| 1 | 105/115 | 120/125 | 1.6/1.6 | 7.0 |
| 2 | 120 | 128 | 1.5 | 30.0 |
| 3 | 120 | 140 | 1.5 | 17.0 |
| 4 | 115 | 207 | 1.5 | 20.0 |

FIG. 33 is the mass spectrum for the reaction product of Example XII(A) containing the compound having the structure:

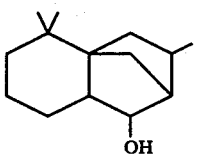

FIG. 34 is the NMR spectrum for Fraction 3 of the distillation product of the reaction product of Example XII(A) containing the compound having the structure:

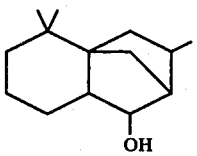

FIG. 35 is the infra-red spectrum for Fraction 4 of the distillation product of the reaction product of Example XII(A) containing the compound having the structure:

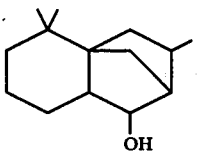

EXAMPLE XII(B)

Reaction:

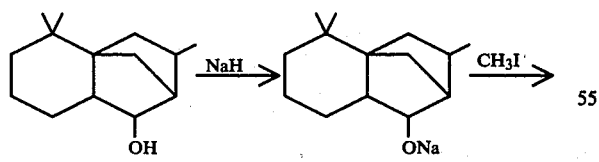

Into a 1 liter reaction flask equipped with stirrer, condenser, thermometer and dropping funnel is placed 70 cc of anhydrous tetrahydrofuran. Slowly, 16.46 grams (0.341 moles) of 50% sodium hydride is added to the tetrahydrofuran. The 70.0 grams (0.341 moles) of the tricyclic alcohol prepared according to Example XII(A) is then added in the form of a tetrahydrofuran solution dropwise to the reaction mass. The reaction mass is refluxed over a period of 4 hours and monitored using infra-red analysis to completion. When all of the starting material disappears, the reaction mass is cooled to room temperature and 48.4 grams (0.341 moles) of methyl iodide is added dropwise to the reaction mass. The reaction mass exotherms to 40° C. Refluxing continues for a period of 8 hours whereupon infra-red analysis indicates that the reaction to form the ether is completed. The reaction mass is cooled and hydrolized with 200 cc of water. The organic phase is separated from the aqueous phase and the organic phase is washed with two 100 cc portions of water, dried and stripped of solvent and distilled yielding the following fractions (distillation on a 12 inch stone packed column):

| Fraction Number | Vapor Temp. °C. | Liquid Temp. °C. | Head Vac. mm. Hg | Weight of Fraction |
|---|---|---|---|---|
| 1 | 100/105 | 121/128 | 0.9/0.9 | 13.0 |
| 2 | 110 | 140 | 0.9 | 27.0 |
| 3 | 110 | 198 | 0.9 | 13.0 |

FIG. 36 is the mass spectrum of the reaction product of Example XII(B) containing the compound having the structure:

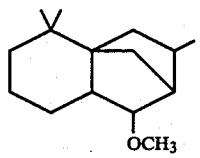

FIG. 37 is the NMR spectrum for Fraction 2 of the distillation product of the reaction product of Example XII(B) containing the compound having the structure:

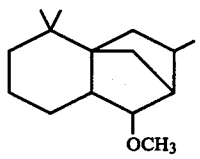

FIG. 38 is the infra-red spectrum for Fraction 2 of the distillation product of the reaction product of Example XII(B) containing the compound having the structure:

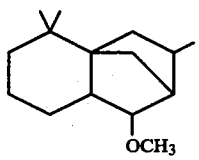

EXAMPLE XIII

PREPARATION OF OCTAHYDRO-2,3,5,5-TETRAMETHYL-2H-2,4A-METHANONAPHTHALENE-1-OL

EXAMPLE XIII(A)

Reaction:

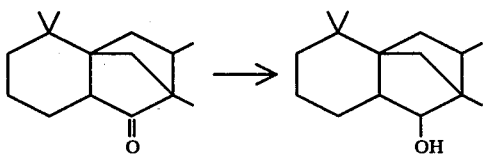

Into a 500 cc reaction flask equipped with stirrer, thermometer, reflux condenser and nitrogen blanket apparatus is added 200 cc of anhydrous tetrahydrofuran. To the anhydrous tetrahydrofuran 24.0 grams (0.6 moles) of 95% lithium aluminum hydride is added. 132.0 grams (0.6 moles) of the tricyclic ketone prepared according to Example VI is then added dropwise to the reaction mass while maintaining the reaction mass at room temperature. The reaction mass is then stirred at room temperature for a period of 2 hours. The reaction mass is then hydrolized with 200 cc of water added dropwise with cooling. The resulting organic phase is separated from the aqueous phase and the organic phase is distilled on a 12 inch stone packed column yielding the compound having the structure:

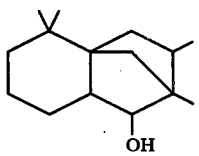

as confirmed by NMR, IR and mass spectral analyses.

FIG. 39 is the mass spectrum for the reaction product of Example XIII(A) containing the compound having the structure:

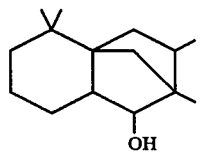

FIG. 40 is the NMR spectrum for Fraction 3 of the distillation product of the reaction product of Example XIII(A) containing the compound having the structure:

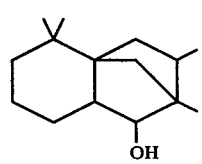

FIG. 41 is the infra-red spectrum for the distillation product of the reaction product of Example XIII(A) containing the compound having the structure:

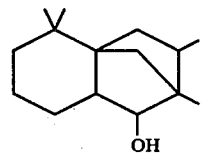

EXAMPLE XIII(B)

Reaction:

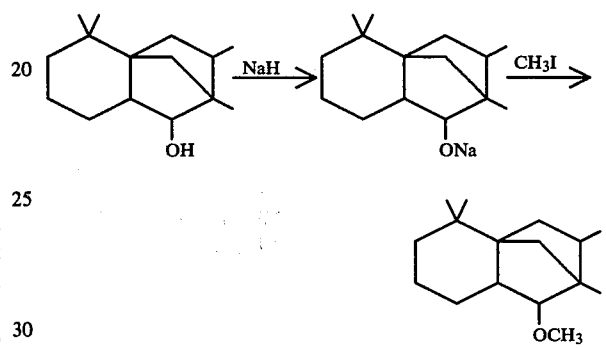

Into a 2 liter reaction vessel equipped with stirrer, condenser, thermometer and dropping funnel is placed 100 cc of tetrahydrofuran and 21.5 grams (0.440 moles) of 50% sodium hydride solution. Dropwise over a period of 30 minutes, the tricyclic alcohol produced according to Example XIII(A) (97.0 grams; 0.440 moles) is added. At the end of the addition, the reaction mass temperature is 25° C. The reaction mass is then refluxed and monitored by infra-red analysis to completion. When infra-red analysis indicates that no further starting material remains, the reaction mass is cooled to room temperature and over a period of 30 minutes, 62.04 grams (0.440 moles) of iodomethane is added dropwise. The reaction mass exotherms to 40° C. At the end of the addition, the reaction mass is refluxed for 10 hours. Infra-red analysis then indicates that the ether is fully formed. The reaction mass is cooled and hydrolyzed with 100 cc of water. The organic phase is separated from the aqueous phase and the organic layer is washed with two 200 cc portions of water, dried, stripped of solvent and distilled on a microdistillation column yielding the following fractions:

| Fraction Number | Vapor Temp. °C. | Liquid Temp. °C. | Head Vac. mm. Hg | Weight of Fraction |
|---|---|---|---|---|
| 1 | 105/120 | 120/130 | 1.0/1.0 | 6.0 |
| 2 | 120 | 134 | 1.0 | 18.0 |
| 3 | 120 | 140 | 1.0 | 19.0 |
| 4 | 120 | 210 | 1.0 | 19.0 |

FIG. 42 is the NMR spectrum for Fraction 3 of the distillation product of the reaction product of Example XIII(B) containing the compound having the structure:

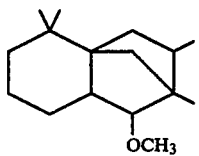

FIG. 43 is the infra-red spectrum for Fraction 3 of the distillation product of the reaction product of Example XIII(B) containing the compound having the structure:

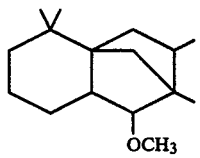

EXAMPLE XIV

PREPARATION OF 3-ETHYL-OCTAHYDRO-2,5,5-TRIMETHYL-2H-2,4A-METHANONAPHTHALENE-1-OL

EXAMPLE XIV(A)

Reaction:

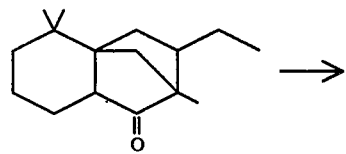

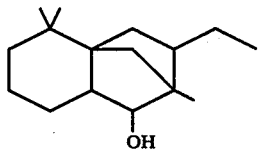

Into a 2000 cc reaction vessel fitted with stirrer, condenser, thermometer and dropping funnel is placed 200 cc of anhydrous tetrahydrofuran. 40 grams (1.0 moles) of 95% lithium aluminum anhydride is then added to the tetrahydrofuran. The resulting mixture is stirred and the tricyclic ketone produced according to Example X(C) is added dropwise over a period of 30 minutes while maintaining the reaction mass at 25°–30° C. The reaction mass is then stirred at room temperature for 2 hours. Infra-red analysis indicates that the reaction is complete and the organic layer is extracted, stripped of solvent and distilled yielding the following fractions:

| Fraction Number | Vapor Temp. °C. | Liquid Temp. °C. | Head Vac. mm. Hg | Weight of Fraction |
|---|---|---|---|---|
| 1 | 95/120 | 140/140 | 2.0/2.0 | 10.0 |
| 2 | 130 | 140 | 2.0 | 44.0 |
| 3 | 133 | 166 | 2.0 | 35.0 |
| 4 | 134 | 168 | 2.0 | 79.0 |
| 5 | 125 | 220 | 2.0 | 8.0 |

The distillation is carried out on a 12 inch stone packed column.

FIG. 44 is the mass spectrum for the reaction product of Example XIV(A) containing the compound having the structure:

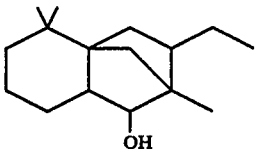

FIG. 45 is the NMR spectrum for Fraction 4 of the distillation product of the reaction product of Example XIV(A) containing the compound having the structure:

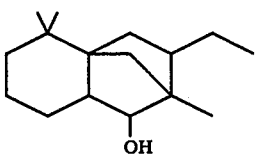

FIG. 46 is the infra-red spectrum for Fraction 4 of the distillation product of the reaction product of Example XIV(A) containing the compound having the structure:

EXAMPLE XIV(B)

Reaction:

Into a 2000 cc reaction vessel equipped with stirrer, condenser, thermometer and dropping funnel is placed 200 cc of tetrahydrofuran and 36.0 grams (0.752 moles)

of 50% sodium hydride. 176.0 grams (0.752 moles) of tricyclic alcohol prepared according to Example XIV(A) is dissolved in tetrahydrofuran and the resulting solution is added dropwise over a 20 minute period to the reaction mass with stirring. No exotherm occurs. The reaction mass is then refluxed and monitored using infra-red analysis to completion. The time of refluxing is 4 hours. The reaction mass at the end of the 4 hour period is then cooled to room temperature and over a period of 30 minutes 106.0 grams (0.752 moles) of methyl iodide is added dropwise. The reaction mass exotherms to 40° C. The reaction mass is then refluxed for a period of 8 hours whereupon infra-red analysis indicates that the reaction to form the ether is complete. The reaction mass is cooled and hydrolized with 200 cc of water and the organic phase is separated from the aqueous phase. The organic phase is washed with two 200 cc portions of water, dried, stripped of solvent and distilled on a 12 inch stone packed column yielding the following fractions:

| Fraction Number | Vapor Temp. °C. | Liquid Temp. °C. | Head Vac. mm. Hg | Weight of Fraction |
|---|---|---|---|---|
| 1 | 125/130 | 135/140 | 0.9/0.9 | 14.0 |
| 2 | 125 | 140 | 0.6 | 36.0 |
| 3 | 125 | 140 | 0.6 | 40.0 |
| 4 | 125 | 150 | 0.6 | 40.0 |
| 5 | 125 | 200 | 0.6 | 18.0 |
| 6 | 140 | 220 | 1.2 | 10.0 |

FIG. 47 is the mass spectrum for the reaction product of Example XIV(B) containing the compound having the structure:

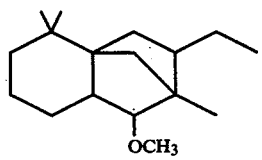

FIG. 48 is the NMR spectrum for Fraction 4 of the distillation product of the reaction product of Example XIV(B) containing the compound having the structure:

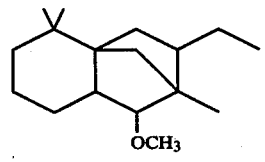

FIG. 49 is the infra-red spectrum for Fraction 4 of the distillation product of the reaction product of Example XIV(B) containing the compound having the structure:

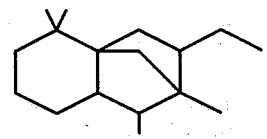

EXAMPLE XV

PREPARATION OF OCTAHYDRO-2,5,5-TRIMETHYL-2H-2,4A-METHANONAPHTHALENE-1-OL

EXAMPLE XV(A)

Reaction:

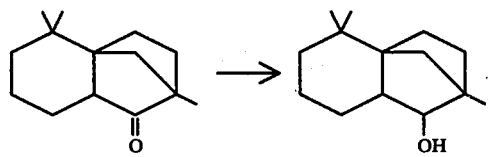

Into a 500 cc reaction flask equipped with stirrer, condenser, thermometer and dropping funnel is placed 50 cc of anhydrous tetrahydrofuran. 12.7 grams (0.336 moles) of lithium aluminum hydride is then added to the tetrahydrofuran. The resulting mixture is stirred for 5 minutes and the tricyclic ketone produced according to Example VIII is then added to the reaction mass dropwise at 20°-25° C. The tricyclic ketone is previously dissolved in tetrahydrofuran. The resulting reaction mixture is stirred at room temperature for a period of 2 hours whereupon infra-red analysis indicates that the reaction is complete. 50 cc of water is then added dropwise and the reaction mass is extracted with two 100 cc volumes of diethylether. The solvent is stripped off and the solid residue is dried in a vacuum oven.

FIG. 50 is the GLC profile for the reaction product of Example XV(A) containing the compound having the structure:

FIG. 51 is the mass spectrum for the reaction product of Example XV(A) containing the compound having the structure:

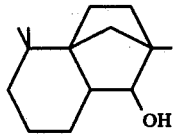

FIG. 52 is the NMR spectrum for Fraction 1 of the distillation product of the reaction product of Example XV(A) containing the compound having the structure:

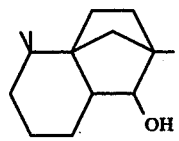

FIG. 53 is the infra-red spectrum for Fraction 1 of the distillation product of the reaction product of Example XV(A) containing the compound having the structure:

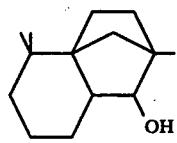

EXAMPLE XV(B)

Reaction:

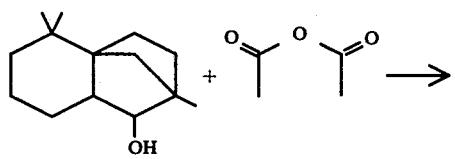

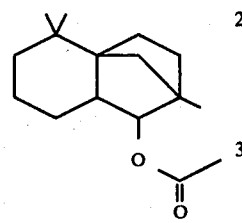

Into a 200 cc reaction vessel equipped with stirrer, condenser, thermometer and dropping funnel is placed 44.0 grams (0.435 moles) of acetic anhydride. To the acetic anhydride is placed 1.0 grams (0.012 moles) of sodium acetate. 30.0 grams (0.145 moles) of the tricyclic alcohol prepared according to Example XV(A) is dissolved in 25 cc of tetrahydrofuran. The resulting solution is added dropwise to the acetic anhydridesodium acetate mixture. The resulting mixture does not exotherm. The reaction mass is then refluxed for a period of 2 hours and infra-red analysis and GLC analysis indicate that no starting material remains. 100 cc of water is then added and the reaction mass is extracted with two 100 cc volumes of diethylether. The ether extracts are washed with three 100 cc volumes of water, two 100 cc volumes of saturated sodium bicarbonate solution and then dried and stripped of solvent and distilled on a microdistillation column yielding the following 2 fractions:

| Fraction Number | Vapor Temp. °C. | Liquid Temp. °C. | Head Vac. mm. Hg | Weight of Fraction |
|---|---|---|---|---|
| 1 | 125/125 | 130/135 | 0.7/0.7 | 8.0 |
| 2 | 130 | 175 | 0.7 | 18.0 |

FIG. 54 is the mass spectrum for the reaction product of Example XV(B) containing the compound having the structure:

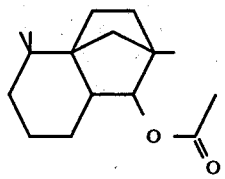

FIG. 55 is the NMR spectrum for Fraction 2 of the distillation product of the reaction product of Example XV(B) containing the compound having the structure:

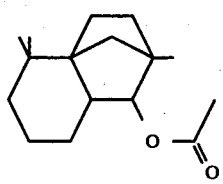

FIG. 56 is the infra-red spectrum of Fraction 2 of the distillation product of the reaction product of Example XV(B) containing the compound having the structure:

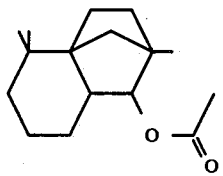

EXAMPLE XV(C)

Reaction:

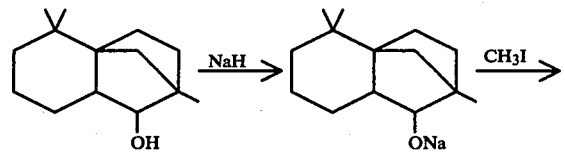

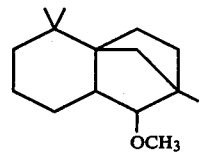

Into a 500 cc reaction vessel equipped with stirrer, condenser, thermometer, dropping funnel and nitrogen blanket apparatus is added 60 cc of tetrahydrofuran followed by 3.5 grams (0.145 moles) of sodium hydride. 30.0 grams (0.145 moles) of the tricyclic alcohol prepared according to Example XV(A) is then dissolved in 25 cc of tetrahydrofuran. The resulting tricyclic alcohol-tetrahydrofuran solution is added dropwise to the reaction mass. The reaction mass is stirred at room temperature for a period of 2 hours. GLC analysis (carbowax column: 100°–220° C. at 8° C. per minute) and infra-red analysis indicates that no starting material is left. Then, 20.59 grams (0.145 moles) of methyl iodide is added to the reaction mass dropwise while cooling the reaction mass, over a period of 10 minutes. The reaction mass is then stirred for 1.5 hours at room temperature. GLC analysis indicates completion of the reaction. The reaction mass is then hydrolyzed with 50 cc of water, extracted with two 100 cc portions of diethylether, dried, stripped of solvent and distilled on a microdistillation column yielding the following fractions:

| Fraction Number | Vapor Temp. °C. | Liquid Temp. °C. | Head Vac. mm. Hg | Weight of Fraction |
|---|---|---|---|---|
| 1 | 97/105 | 115/118 | 1.7/1.0 | 3.0 |
| 2 | 105 | 120 | 1.0 | 10.0 |
| 3 | 105 | 140 | 0.8 | 14.0 |

FIG. 57 is the GLC profile for the reaction product of Example XV(C) containing the compound having the structure:

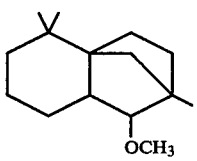

FIG. 58 is the mass spectrum for Fraction 2 of the distillation product of the reaction product of Example XV(C) containing the compound having the structure:

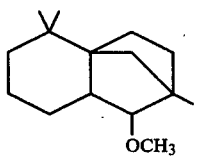

FIG. 59 is the NMR spectrum for Fraction 2 of the distillation product of the reaction product of Example XV(C) containing the compound having the structure:

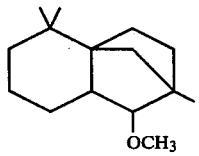

FIG. 60 is the infra-red spectrum for Fraction 2 of the distillation product of the reaction product of Example XV(C) containing the compound having the structure:

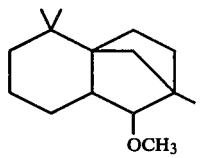

EXAMPLE XVI

PREPARATION OF OCTAHYDRO-3,8,8,9-TETRAMETHYL-2H-2,4A-METHANONAPHTHALENE-9-OL

Reaction:

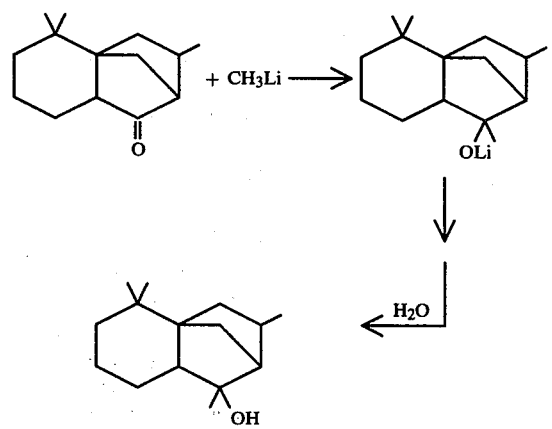

Into a 100 ml reaction flask equipped with magnetic stirrer, reflux condenser, addition funnel and nitrogen blanket apparatus is placed 30 ml of methyl lithium (2.1 moles) and 25 ml anhydrous ether. 5 grams (0.024 moles) of the tricyclic ketone prepared according to Example XIII is then added dropwise to the reaction mass. The addition of the tricyclic ketone takes 30 minutes. The reaction mass is maintained during the addition of the tricyclic ketone at a temperature of between 20°-25° C. The reaction mass is then stirred for a period of 6 hours while maintaining same at 20°-25° C. The reaction mass was then added to water and the reaction mass was washed with water until the pH was neutral. The reaction mass is then stripped of solvent, dried and fractionally distilled yielding a product analyzed by GLC, IR, NMR and mass spectrum analysis to have the structure:

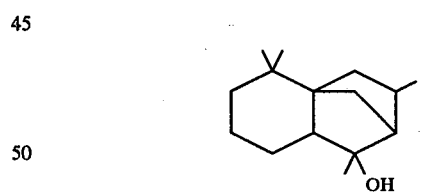

FIG. 61 is the GLC profile for the reaction product for Example XVI containing the compound having the structure:

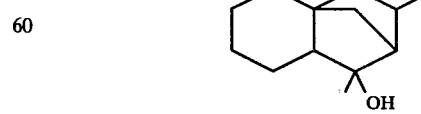

the GLC profile containing six peaks numbered as Peak 1, Peak 2, Peak 3, Peak 4, Peak 5 and Peak 6.

FIG. 62 is the mass spectrum for Peak 1 of the GLC profile of FIG. 61.

FIG. 63 is the NMR spectrum for Peak 1 of the GLC profile of FIG. 61.

FIG. 64 is the NMR spectrum for Peak 2 of the GLC profile of FIG. 61.

FIG. 65 is the infra-red spectrum for Peak 2 of the GLC profile of FIG. 61.

FIG. 66 is the NMR spectrum for Peak 3 of the GLC profile of FIG. 61.

FIG. 67 is the infra-red spectrum for Peak 3 of the GLC profile of FIG. 61.

FIG. 68 is the NMR spectrum for Peak 4 of the GLC profile of FIG. 61.

FIG. 69 is the NMR spectrum for Peak 5 of the GLC profile of FIG. 61.

FIG. 70 is the NMR spectrum for Peak 6 of the GLC profile of FIG. 61.

EXAMPLE XVII

PREPARATION OF A COSMETIC POWDER PREPARATION

A cosmetic powder is prepared by mixing in a ball mill, 100 grams of talcum powder with 0.25 grams of one of the substances set forth in Table II below. The resulting cosmetic powder has a pleasant aroma as set forth in Table II below.

TABLE II

| Structure of Reaction Product | Fragrance Properties |
|---|---|
| 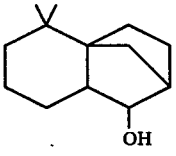 Prepared according to Example XI(A). | A dry woody, thymol-like and camphoraceous-like fragrance with long lasting patchouli undertones. |
| 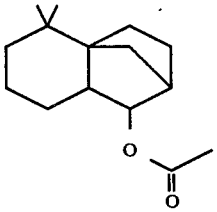 Prepared according to Example XI(B). | A dry woody (cedary, vetiver), amber-like and sandalwood-like aroma. |
| 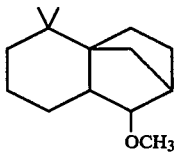 Prepared according to Example XI(C). | A fresh camphoraceous, woody, sweaty and fruity aroma. |
| 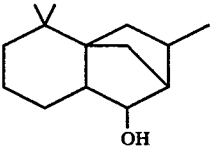 Prepared according to | A dry woody, amber-like, castoreum-like, cedrus atlantica, and patchouli aroma. |

TABLE II-continued

| Structure of Reaction Product | Fragrance Properties |
|---|---|
| Example XII(A). 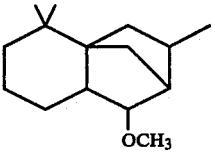 Prepared according to Example XII(B). | A sweet, woody, patchouli-like labdanum and green aroma. |
| 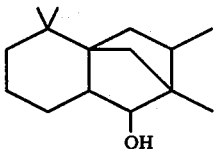 Prepared according to Example XIII(A). | A woody, amber, cedar aroma with green and fruity undertones. |
| 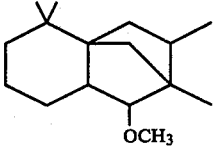 Prepared according to Example XIII(B). | A woody, amber, cigar-box-like, sandalwood-like, oriental aroma. |
| 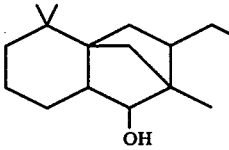 Prepared according to Example XIV(A). | A woody, cedarwood-like and minty aroma profile. |
| 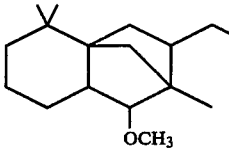 Prepared according to Example XIV(B). | A woody, patchouli aroma profile. |
| 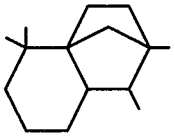 Prepared according to Example XV(A). | A dry woody, spicy, minty, floral (rose) aroma. |

TABLE II-continued

| Structure of Reaction Product | Fragrance Properties |
|---|---|
| Prepared according to Example XV(B). | A dry woody, camphoraceous, sweaty, vetiver-like and grapefruit oil-like aroma. |
| Prepared according to Example XV(C). | An amber, woody, camphoraceous, friuty and sweet aroma profile. |
| Prepared according to Example XVI. | A woody, oily, slightly amber aroma profile. |

EXAMPLE XVIII

PERFUMED LIQUID DETERGENT

Concentrated liquid detergents (Lysine salt of n-dodecylbenzene sulfonic acid as more specifically described in U.S. Pat. No. 3,948,818, issued on Apr. 6, 1976) with fragrance profiles as defined in Table III below are prepared containing 0.10%, 0.15%, 0.20%, 0.25%, 0.30% and 0.35% of the substance as set forth in Table III below. They are prepared by adding and homogeneously mixing the appropriate quantity of substance as set forth in Table III below in the liquid detergent. The detergents all possess excellent intense aromas as defined according to the profiles of Table III below, the intensity increasing with greater concentrations of said substance as set forth below in Table III:

TABLE III

| Structure of Reaction Product | Fragrance Properties |
|---|---|
| Prepared according to Example XI(A). | A dry woody, thymol-like and camphoraceous-like fragrance with long lasting patchouli undertones. |

TABLE III-continued

| Structure of Reaction Product | Fragrance Properties |
|---|---|
| Prepared according to Example XI(B). | A dry woody (cedary, vetiver), amber-like and sandalwood-like aroma. |
| Prepared according to Example XI(C). | A fresh camphoraceous, woody, sweaty and fruity aroma. |
| Prepared according to Example XII(A). | A dry woody, amber-like, castoreum-like, cedrus atlantica, and patchouli aroma. |
| Prepared according to Example XII(B). | A sweet, woody, patchouli-like labdanum and green aroma. |
| Prepared according to Example XIII(A). | A woody, amber, cedar aroma with green and fruity undertones. |
| Prepared according to Example XIII(B). | A woody, amber, cigar-box-like, sandalwood-like, oriental aroma. |

TABLE III-continued

| Structure of Reaction Product | Fragrance Properties |
|---|---|
| Prepared according to Example XIV(A). | A woody, cedarwood-like and minty aroma profile. |
| Prepared according to Example XIV(B). | A woody, patchouli aroma profile. |
| Prepared according to Example XV(A). | A dry woody, spicy, minty, floral (rose) aroma. |
| Prepared according to Example XV(B). | A dry woody, camphoraceous, sweaty, vetiver-like and grapefruit oil-like aroma. |
| Prepared according to Example XV(C). | An amber, woody, camphoraceous, friuty and sweet aroma profile. |
| Prepared according to Example XVI. | A woody, oily, slightly amber aroma profile. |

EXAMPLE XIX

PREPARATION OF A COLOGNE AND HANDKERCHIEF PERFUME

Substances set forth in Table IV below are each individually incorporated into colognes at concentrations of 2.0%, 2.5%, 3.0%, 3.5%, 4.0%, 4.5% and 5.0% in (75%, 80%, 85% and 90%, aqueous food grade ethanol); and into handkerchief perfumes at concentrations of 15%, 20%, 25% and 30% (in 95% aqueous food grade ethanol). Distinctive and definitive long-lasting warm aromas as defined according to Table IV below are all imparted to the cologne and to the handkerchief perfumes at all levels as indicated above:

TABLE IV

| Structure of Reaction Product | Fragrance Properties |
|---|---|
| Prepared according to Example XI(A). | A dry woody, thymol-like and camphoraceous-like fragrance with long lasting patchouli undertones. |
| Prepared according to Example XI(B). | A dry woody (cedary, vetiver), amber-like and sandalwood-like aroma. |
| Prepared according to Example XI(C). | A fresh camphoraceous, woody, sweaty and fruity aroma. |
| Prepared according to Example XII(A). | A dry woody, amber-like, castoreum-like, cedrus atlantica, and patchouli aroma. |
| Prepared according to Example XII(B). | A sweet, woody, patchouli-like labdanum and green aroma. |

TABLE IV-continued

| Structure of Reaction Product | Fragrance Properties |
|---|---|
| (structure with OH) Prepared according to Example XIII(A). | A woody, amber, cedar aroma with green and fruity undertones. |
| (structure with OCH₃) Prepared according to Example XIII(B). | A woody, amber, cigar-box-like, sandalwood-like, oriental aroma. |
| (structure with OH and ethyl) Prepared according to Example XIV(A). | A woody, cedarwood-like and minty aroma profile. |
| (structure with OCH₃ and ethyl) Prepared according to Example XIV(B). | A woody, patchouli aroma profile. |
| (structure with OH) Prepared according to Example XV(A). | A dry woody, spicy, minty, floral (rose) aroma becoming warm and rich on dryout. |
| (structure with OC(=O)CH₃) Prepared according to Example XV(B). | A dry woody, camphoraceous, sweaty, vetiver-like and grapefruit oil-like aroma. |
| (structure with OCH₃) Prepared according to Example XV(C). | An amber, woody, camphoraceous, friuty and sweet aroma profile. |
| (structure with OH) Prepared according to Example XVI. | A woody, oily, slightly amber aroma profile. |

EXAMPLE XX

PREPARATION OF SOAP COMPOSITION

One hundred grams of soap chips (IVORY ®, produced by the Procter & Gamble Company, Cincinnati, Ohio) are admixed with one gram of the substance as set forth in Table V below until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest excellent, long-lasting, warm aromas as set forth in the Table V below:

TABLE V

| Structure of Reaction Product | Fragrance Properties |
|---|---|
| (structure with OH) Prepared according to Example XI(A). | A dry woody, thymol-like and camphoraceous-like fragrance with long lasting patchouli undertones. |
| (structure with OC(=O)CH₃) Prepared according to Example XI(B). | A dry woody (cedary, vetiver), amber-like and sandalwood-like aroma. |
| (structure with OCH₃) Prepared according to Example XI(C). | A fresh camphoraceous, woody, sweaty and fruity aroma. |

TABLE V-continued

| Structure of Reaction Product | Fragrance Properties |
|---|---|
| Prepared according to Example XII(A). (OH) | A dry woody, amber-like, castoreum-like, cedrus atlantica, and patchouli aroma. |
| Prepared according to Example XII(B). (OCH₃) | A sweet, woody, patchouli-like labdanum and green aroma. |
| Prepared according to Example XIII(A). (OH) | A woody, amber, cedar aroma with green and fruity undertones. |
| Prepared according to Example XIII(B). (OCH₃) | A woody, amber, cigar-box-like, sandalwood-like, oriental aroma. |
| Prepared according to Example XIV(A). (OH) | A woody, cedarwood-like and minty aroma profile. |
| Prepared according to Example XIV(B). (OCH₃) | A woody, patchouli aroma profile. |
| Prepared according to Example XV(A). (OH) | A dry woody, spicy, minty, floral (rose) aroma. |
| Prepared according to Example XV(B). (O-C(=O)-CH₃) | A dry woody, camphoraceous, sweaty, vetiver-like, and grapefruit oil-like aroma. |
| Prepared according to Example XV(C). (OCH₃) | An amber, woody, camphoraceous, fruity and sweet aroma profile. |
| Prepared according to Example XVI. (OH) | A woody, oily, slightly amber aroma profile. |

EXAMPLE XXI

PREPARATION OF SOLID DETERGENT COMPOSITIONS

Detergents are prepared from the following ingredients according to Example I of Canadian Pat. No. 1,007,948:

| Ingredient | Percent by Weight |
|---|---|
| Neodol ® 45-11 (a C₁₄–C₁₅ Alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of the substance as set forth in Table VI below. Each of the detergent samples have excellent, warm aromas as indicated in Table VI below:

TABLE VI

| Structure of Reaction Product | Fragrance Properties |
|---|---|
| Prepared according to Example XI(A). (OH) | A dry woody, thymol-like and camphoraceous-like fragrance with long lasting patchouli undertones. |

Fabric softening compositions containing substances as set forth in Table VII below essentially consist of a substrate having a weight of about 3 grams per 100 square inches of substrate coating, of about 1.85 grams per 100 square inches of substrate, and an outer coating of about 1.4 grams per 100 square inches of substrate, thereby providing a total aromatized substrate and outer coating weight ration of about 1:1 by weight of the substrate. The aromas as set forth in Table VII below, are imparted in a pleasant manner, to the head space in the dryer on operation thereof, using the said dryer-added fabric softening non-woven fabric:

TABLE VII

| Structure of Reaction Product | Fragrance Properties |
|---|---|
| Prepared according to Example XI(A). (structure with OH) | A dry woody, thymol-like and camphoraceous-like fragrance with long lasting patchouli undertones. |
| Prepared according to Example XI(B). (structure with O-acetate) | A dry woody (cedary, vetiver), amber-like and sandalwood-like aroma. |
| Prepared according to Example XI(C). (structure with OCH₃) | A fresh camphoraceous, woody, sweaty and fruity aroma. |
| Prepared according to Example XII(A). (structure with OH) | A dry woody, amber-like, castoreum-like, cedrus atlantica, and patchouli aroma. |
| Prepared according to Example XII(B). (structure with OCH₃) | A sweet, woody, patchouli-like labdanum and green aroma. |
| Prepared according to Example XIII(A). (structure with OH) | A woody, amber, cedar aroma with green and fruity undertones. |

TABLE VII-continued

| Structure of Reaction Product | Fragrance Properties |
|---|---|
| Prepared according to Example XIII(B). (structure with OCH₃) | A woody, amber, cigar-box-like, sandalwood-like, oriental aroma. |
| Prepared according to Example XIV(A). (structure with OH) | A woody, cedarwood-like and minty aroma profile. |
| Prepared according to Example XIV(B). (structure with OCH₃) | A woody, patchouli aroma profile. |
| Prepared according to Example XV(A). (structure with OH) | A dry woody, spicy, minty, floral (rose) aroma. |
| Prepared according to Example XV(B). (structure with O-acetate) | A dry woody, camphoraceous, sweaty, vetiver-like, and grapefruit oil-like aroma. |
| Prepared according to Example XV(C). (structure with OCH₃) | An amber, woody, camphoraceous, fruity and sweet aroma profile. |
| Prepared according to (structure with OH) | A woody, oily, slightly amber aroma profile. |

TABLE VI-continued

| Structure of Reaction Product | Fragrance Properties |
|---|---|
| Prepared according to Example XI(B). | A dry woody (cedary, vetiver), amber-like and sandalwood-like aroma. |
| Prepared according to Example XI(C). (OCH₃) | A fresh camphoraceous, woody, sweaty and fruity aroma. |
| Prepared according to Example XII(A). (OH) | A dry woody, amber-like, castoreum-like, cedrus atlantica, and patchouli aroma. |
| Prepared according to Example XII(B). (OCH₃) | A sweet, woody, patchouli-like labdanum and green aroma. |
| Prepared according to Example XIII(A). (OH) | A woody, amber, cedar aroma with green and fruity undertones. |
| Prepared according to Example XIII(B). (OCH₃) | A woody, amber, cigar-box-like, sandalwood-like, oriental aroma. |
| Prepared according to Example XIV(A). (OH) | A woody, cedarwood-like and minty aroma profile. |
| Prepared according to Example XIV(B). (OCH₃) | A woody, patchouli aroma profile. |
| Prepared according to Example XV(A). (OH) | A dry woody, spicy, minty, floral (rose) aroma. |
| Prepared according to Example XV(B). | A dry woody, camphoraceous, sweaty, vetiver-like, and grapefruit oil-like aroma. |
| Prepared according to Example XV(C). (OCH₃) | An amber, woody, camphoraceous, fruity and sweet aroma profile. |
| Prepared according to Example XVI. (OH) | A woody, oily, slightly amber aroma profile. |

EXAMPLE XXII

Utilizing the procedure of Example I of column 15 of U.S. Pat. No. 3,632,396. a non-woven cloth substrate useful as a dryer-added fabric softening article of manufacture prepared wherein the substrate, the substrate coating and the outer coating and the perfuming material are as follows:
1. a water "dissolvable" paper ("Dissolvo Paper")
2. Adogen 448 (m.p. about 140° F.) as the substrate coating; and
3. An outer coating having the following formulation (m.p. about 150° F.):
    57 percent $C_{20-22}$ HAPS
    22 percent isopropyl alcohol
    20 percent antistatic agent
    1 percent of one of the substances as set forth in Table VII below.

TABLE VII-continued

| Structure of Reaction Product | Fragrance Properties |
|---|---|
| Example XVI. | |

In the following examples, Aromox®DMC-W and Aromox®DMMC-W are 30% aqueous solutions of dimethyl cocoamine oxide; and Aromox®NCMDW is a 40% aqueous solution of N-cocomorpholine oxide produced by Armac division of AKZO of Chicago, Ill.

EXAMPLE XXIII

Four drops of one of the substances set forth in Table VIII below is added to two grams of Aromox®DMC-W to produce a clear premix. The clear premix is added to 200 grams of CLOROX® with stirring resulting in a clear stable, single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table VIII below. Furthermore, no such characteristic "hypochlorite" aroma is retained on the hands of the individual handling such laundry in both the wet and the dry states:

TABLE VIII

| Structure of Reaction Product | Fragrance Properties |
|---|---|
| 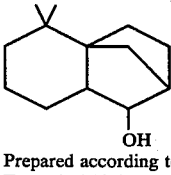<br>OH<br>Prepared according to Example XI(A). | A dry woody, thymol-like and camphoraceous-like fragrance with long lasting patchouli undertones. |
| 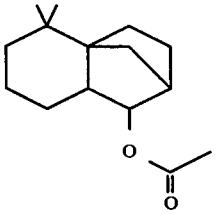<br>Prepared according to Example XI(B). | A dry woody (cedary, vetiver), amber-like and sandalwood-like aroma. |
| 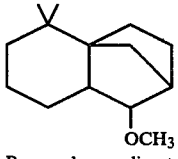<br>OCH₃<br>Prepared according to Example XI(C). | A fresh camphoraceous, woody, sweaty and fruity aroma. |
| 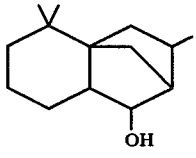<br>OH<br>Prepared according to Example XII(A). | A dry woody, amber-like, castoreum-like, cedrus atlantica, and patchouli aroma. |

TABLE VIII-continued

| Structure of Reaction Product | Fragrance Properties |
|---|---|
| 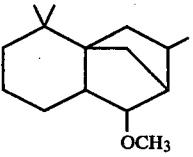<br>OCH₃<br>Prepared according to Example XII(B). | A sweet, woody, patchouli-like labdanum and green aroma. |
| 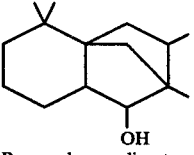<br>OH<br>Prepared according to Example XIII(A). | A woody, amber, cedar aroma with green and fruity undertones. |
| 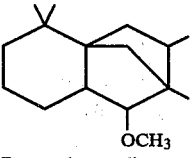<br>OCH₃<br>Prepared according to Example XIII(B). | A woody, amber, cigar-box-like, sandalwood-like, oriental aroma. |
| 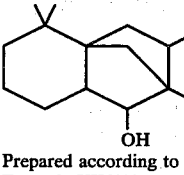<br>OH<br>Prepared according to Example XIV(A). | A woody, cedarwood-like and minty aroma profile. |
| 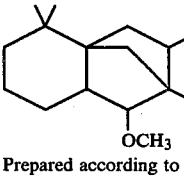<br>OCH₃<br>Prepared according to Example XIV(B). | A woody, patchouli aroma profile. |
| 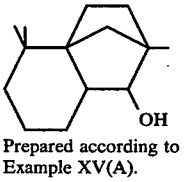<br>OH<br>Prepared according to Example XV(A). | A dry woody, spicy, minty, floral (rose) aroma. |
| 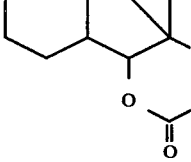<br>Prepared according to Example XV(B). | A dry woody, camphoraceous, sweaty, vetiver-like, and grapefruit oil-like aroma. |

TABLE VIII-continued

| Structure of Reaction Product | Fragrance Properties |
|---|---|
| [Structure with OCH₃ group] Prepared according to Example XV(C). | An amber, woody, camphoraceous, fruity and sweet aroma profile. |
| [Structure with OH group] Prepared according to Example XVI. | A woody, oily, slightly amber aroma profile. |

EXAMPLE XXIV

Aromox®DMMC-W in various quantities is mixed with 0.1 grams of one of the substances set forth in Table IX below. The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table IX below. Furthermore, no such characteristic "hypochlorite" aroma is retained on the hands of the individual handling such laundry in both the wet and the dry states:

TABLE IX

| Structure of Reaction Product | Fragrance Properties |
|---|---|
| [Structure with OH group] Prepared according to Example XI(A). | A dry woody, thymol-like and camphoraceous-like fragrance with long lasting patchouli undertones. |
| [Structure with O-C(=O)- group] Prepared according to Example XI(B). | A dry woody (cedary, vetiver), amber-like and sandalwood-like aroma. |
| [Structure with OCH₃ group] Prepared according to Example XI(C). | A fresh camphoraceous, woody, sweaty and fruity aroma. |
| [Structure with OH group] Prepared according to Example XII(A). | A dry woody, amber-like, castoreum-like, cedrus atlantica, and patchouli aroma. |
| [Structure with OCH₃ group] Prepared according to Example XII(B). | A sweet, woody, patchouli-like labdanum and green aroma. |
| [Structure with OH group] Prepared according to Example XIII(A). | A woody, amber, cedar aroma with green and fruity undertones. |
| [Structure with OCH₃ group] Prepared according to Example XIII(B). | A woody, amber, cigar-box-like, sandalwood-like, oriental aroma. |
| [Structure with OH group and ethyl] Prepared according to Example XIV(A). | A woody, cedarwood-like and minty aroma profile. |

TABLE IX-continued

| Structure of Reaction Product | Fragrance Properties |
|---|---|
| (structure with OCH₃) Prepared according to Example XIV(B). | A woody, patchouli aroma profile. |
| (structure with OH) Prepared according to Example XV(A). | A dry woody, spicy, minty, floral (rose) aroma. |
| (structure with O-C(=O)-) Prepared according to Example XV(B). | A dry woody, camphoraceous, sweaty, vetiver-like, and grapefruit oil-like aroma. |
| (structure with OCH₃) Prepared according to Example XV(C). | An amber, woody, camphoraceous, fruity and sweet aroma profile. |
| (structure with OH) Prepared according to Example XVI. | A woody, oily, slightly amber aroma profile. |

EXAMPLE XXV

Two grams of Aromox ®DMMC-W is admixed with eight drops of one of the substances set forth in Table X below. The premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of 1 week. The resulting solution remains clear in a single phase. When used as a laundry bleach, the resulting bleached laundry, on dry-out in an atmosphere of 50% relative humidity retains a "clean" warm aroma as set forth in Table X below; whereas without the use of the substance set forth in Table X below, the bleached laundry has a faint characteristic disagreeable "hypochlorite" aroma.

TABLE X

| Structure of Reaction Product | Fragrance Properties |
|---|---|
| (structure with OH) Prepared according to Example XI(A). | A dry woody, thymol-like and camphoraceous-like fragrance with long lasting patchouli undertones. |
| (structure with O-C(=O)-) Prepared according to Example XI(B). | A dry woody (cedary, vetiver), amber-like and sandalwood-like aroma. |
| (structure with OCH₃) Prepared according to Example XI(C). | A fresh camphoraceous, woody, sweaty and fruity aroma. |
| (structure with OH) Prepared according to Example XII(A). | A dry woody, amber-like, castoreum-like, cedrus atlantica, and patchouli aroma. |
| (structure with OCH₃) Prepared according to Example XII(B). | A sweet, woody, patchouli-like labdanum and green aroma. |
| (structure with OH) Prepared according to Example XIII(A). | A woody, amber, cedar aroma with green and fruity undertones. |

TABLE X-continued

| Structure of Reaction Product | Fragrance Properties |
|---|---|
| (structure with OCH₃) Prepared according to Example XIII(B). | A woody, amber, cigar-box-like, sandalwood-like, oriental aroma. |
| (structure with OH) Prepared according to Example XIV(A). | A woody, cedarwood-like and minty aroma profile. |
| (structure with OCH₃) Prepared according to Example XIV(B). | A woody, patchouli aroma profile. |
| (structure with OH) Prepared according to Example XV(A). | A dry woody, spicy, minty, floral (rose) aroma. |
| (structure with O-C(=O)-) Prepared according to Example XV(B). | A dry woody, camphoraceous, sweaty, vetiver-like, and grapefruit oil-like aroma. |
| (structure with OCH₃) Prepared according to Example XV(C). | An amber, woody, camphoraceous, fruity and sweet aroma profile. |
| (structure with OH) Prepared according to Example XVI. | A woody, oily, slightly amber aroma profile. |

EXAMPLE XXVI

Two grams of Aromox ®DMMC-W is admixed with eight drops of one of the substance of Table XI below. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table XI below; whereas without the use of the substance set forth in Table XI below, the bleached laundry has a faint characteristic disagreeable "hypochlorite" aroma:

TABLE XI

| Structure of Reaction Product | Fragrance Properties |
|---|---|
| (structure with OH) Prepared according to Example XI(A). | A dry woody, thymol-like and camphoraceous-like fragrance with long lasting patchouli undertones. |
| (structure with O-C(=O)-) Prepared according to Example XI(B). | A dry woody (cedary, vetiver), amber-like and sandalwood-like aroma. |
| (structure with OCH₃) Prepared according to Example XI(C). | A fresh camphoraceous, woody, sweaty and fruity aroma. |

TABLE XI-continued

| Structure of Reaction Product | Fragrance Properties |
|---|---|
| [structure with OH] Prepared according to Example XII(A). | A dry woody, amber-like, castoreum-like, cedrus atlantica, and patchouli aroma. |
| [structure with OCH3] Prepared according to Example XII(B). | A sweet, woody, patchouli-like labdanum and green aroma. |
| [structure with OH] Prepared according to Example XIII(A). | A woody, amber, cedar aroma with green and fruity undertones. |
| [structure with OCH3] Prepared according to Example XIII(B). | A woody, amber, cigar-box-like, sandalwood-like, oriental aroma. |
| [structure with OH] Prepared according to Example XIV(A). | A woody, cedarwood-like and minty aroma profile. |
| [structure with OCH3] Prepared according to Example XIV(B). | A woody, patchouli aroma profile. |
| [structure with OH] | A dry woody, spicy, minty, floral (rose) aroma. |

TABLE XI-continued

| Structure of Reaction Product | Fragrance Properties |
|---|---|
| [structure with O–C(=O)–] Prepared according to Example XV(A). | A dry woody, camphoraceous, sweaty, vetiver-like, and grapefruit oil-like aroma. |
| Prepared according to Example XV(B). | |
| [structure with OCH3] Prepared according to Example XV(C). | An amber, woody, camphoraceous, fruity and sweet aroma profile. |
| [structure with OH] Prepared according to Example XVI. | A woody, oily, slightly amber aroma profile. |

EXAMPLE XXVII

Two grams of Aromox ®DMMC-W is admixed with eight drops of one of the substances set forth in Table XII below. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. the resulting solution remains clear as a single phase when used as a laundry bleach. The resulting bleached laundry, on dry-out in an atmosphere of 50% relative humidity, retains an aroma as set forth in Table XII below, whereas without the use of the substance set forth in Table XII below, the bleached laundry has a faint characteristic disagreeable "hypochlorite" aroma.

TABLE XII

| Structure of Reaction Product | Fragrance Properties |
|---|---|
| [structure with OH] Prepared according to Example XI(A). | A dry woody, thymol-like and camphoraceous-like fragrance with long lasting patchouli undertones. |

TABLE XII-continued

| Structure of Reaction Product | Fragrance Properties |
|---|---|
| [structure with OC(=O)CH3 group] Prepared according to Example XI(B). | A dry woody (cedary, vetiver), amber-like and sandalwood-like aroma. |
| [structure with OCH3] Prepared according to Example XI(C). | A fresh camphoraceous, woody, sweaty and fruity aroma. |
| [structure with OH] Prepared according to Example XII(A). | A dry woody, amber-like, castoreum-like, cedrus atlantica, and patchouli aroma. |
| [structure with OCH3] Prepared according to Example XII(B). | A sweet, woody, patchouli-like labdanum and green aroma. |
| [structure with OH] Prepared according to Example XIII(A). | A woody, amber, cedar aroma with green and fruity undertones. |
| [structure with OCH3] Prepared according to Example XIII(B). | A woody, amber, cigar-box-like, sandalwood-like, oriental aroma. |
| [structure with ethyl and OH] Prepared according to Example XIV(A). | A woody, cedarwood-like and minty aroma profile. |
| [structure with ethyl and OCH3] Prepared according to Example XIV(B). | A woody, patchouli aroma profile. |
| [structure with OH] Prepared according to Example XV(A). | A dry woody, spicy, minty, floral (rose) aroma. |
| [structure with OC(=O)CH3] Prepared according to Example XV(B). | A dry woody, camphoraceous, sweaty, vetiver-like, and grapefruit oil-like aroma. |
| [structure with OCH3] Prepared according to Example XV(C). | An amber, woody, camphoraceous, fruity and sweet aroma profile. |
| [structure with OH] Prepared according to Example XVI. | A woody, oily, slightly amber aroma profile. |

EXAMPLE XXVIII

Four drops of one of the substances set forth in Table XIII below is added to 1.5 grams of Aromox®NCMDW to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table XIII below. Furthermore, no such characteristic "hypochlorite" aroma is retained on the hands of the individual handling such laundry in both the wet and the dry states.

TABLE XIII

| Structure of Reaction Product | Fragrance Properties |
|---|---|
| [structure with OH] Prepared according to Example XI(A). | A dry woody, thymol-like and camphoraceous-like fragrance with long lasting patchouli undertones. |
| [structure with O-C(=O)-] Prepared according to Example XI(B). | A dry woody (cedary, vetiver), amber-like and sandalwood-like aroma. |
| [structure with OCH₃] Prepared according to Example XI(C). | A fresh camphoraceous, woody, sweaty and fruity aroma. |
| [structure with OH] Prepared according to Example XII(A). | A dry woody, amber-like, castoreum-like, cedrus atlantica, and patchouli aroma. |
| [structure with OCH₃] Prepared according to Example XII(B). | A sweet, woody, patchouli-like labdanum and green aroma. |

TABLE XIII-continued

| Structure of Reaction Product | Fragrance Properties |
|---|---|
| [structure with OH] Prepared according to Example XIII(A). | A woody, amber, cedar aroma with green and fruity undertones. |
| [structure with OCH₃] Prepared according to Example XIII(B). | A woody, amber, cigar-box-like, sandalwood-like, oriental aroma. |
| [structure with OH] Prepared according to Example XIV(A). | A woody, cedarwood-like and minty aroma profile. |
| [structure with OCH₃] Prepared according to Example XIV(B). | A woody, patchouli aroma profile. |
| [structure with OH] Prepared according to Example XV(A). | A dry woody, spicy, minty, floral (rose) aroma. |
| [structure with O-C(=O)-] Prepared according to Example XV(B). | A dry woody, camphoraceous, sweaty, vetiver-like, and grapefruit oil-like aroma. |

TABLE XIII-continued

| Structure of Reaction Product | Fragrance Properties |
|---|---|
| [structure with OCH₃] Prepared according to Example XV(C). | An amber, woody, camphoraceous, fruity and sweet aroma profile. |
| [structure with OH] Prepared according to Example XVI. | A woody, oily, slightly amber aroma profile. |

EXAMPLE XXIX

Four drops of one of the substances set forth in Table XIV below is added to 1 gram n-undecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table XIV below. Furthermore, no such characteristic "hypochlorite" aroma is retained on the hands of the individual handling such laundry in both the wet and the dry states.

TABLE XIV

| Structure of Reaction Product | Fragrance Properties |
|---|---|
| [structure with OH] Prepared according to Example XI(A). | A dry woody, thymol-like and camphoraceous-like fragrance with long lasting patchouli undertones. |
| [structure with O-C(=O)-] Prepared according to Example XI(B). | A dry woody (cedary, vetiver), amber-like and sandalwood-like aroma. |

TABLE XIV-continued

| Structure of Reaction Product | Fragrance Properties |
|---|---|
| [structure with OCH₃] Prepared according to Example XI(C). | A fresh camphoraceous, woody, sweaty and fruity aroma. |
| [structure with OH] Prepared according to Example XII(A). | A dry woody, amber-like, castoreum-like, cedrus atlantica, and patchouli aroma. |
| [structure with OCH₃] Prepared according to Example XII(B). | A sweet, woody, patchouli-like labdanum and green aroma. |
| [structure with OH] Prepared according to Example XIII(A). | A woody, amber, cedar aroma with green and fruity undertones. |
| [structure with OCH₃] Prepared according to Example XIII(B). | A woody, amber, cigar-box-like, sandalwood-like, oriental aroma. |
| [structure with OH] Prepared according to Example XIV(A). | A woody, cedarwood-like and minty aroma profile. |
| [structure with OCH₃] Prepared according to Example XIV(B). | A woody, patchouli aroma profile. |

TABLE XIV-continued

| Structure of Reaction Product | Fragrance Properties |
|---|---|
| 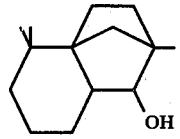<br>Prepared according to Example XV(A). | A dry woody, spicy, minty, floral (rose) aroma. |
| 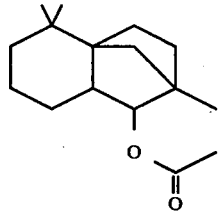<br>Prepared according to Example XV(B). | A dry woody, camphoraceous, sweaty, vetiver-like, and grapefruit oil-like aroma. |
| 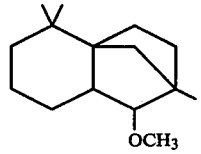<br>Prepared according to Example XV(C). | An amber, woody, camphoraceous, fruity and sweet aroma profile. |
| 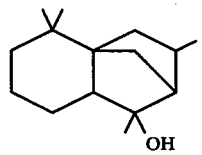<br>Prepared according to Example XVI. | A woody, oily, slightly amber aroma profile. |

EXAMPLE XXX

Four drops of one of the substances as set forth in Table XV below are added to 1 gram of n-dodecyl dimethyl amine oxide to produce a clear premix. The clear premix is added to 200 grams of CLOROX ® with stirring resulting in a clear, stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table XV below. Furthermore, no such characteristic "hypochlorite" aroma is retained on the hands of the individual handling such laundry in both the wet and the dry states.

TABLE XV

| Structure of Reaction Product | Fragrance Properties |
|---|---|
| 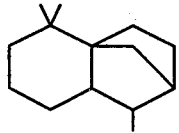<br>Prepared according to Example XI(A). | A dry woody, thymol-like and camphoraceous-like fragrance with long lasting patchouli undertones. |
| 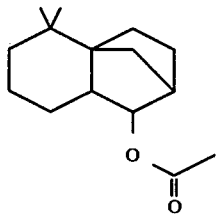<br>Prepared according to Example XI(B). | A dry woody (cedary, vetiver), amber-like and sandalwood-like aroma. |
| 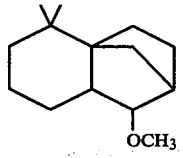<br>Prepared according to Example XI(C). | A fresh camphoraceous, woody, sweaty and fruity aroma. |
| 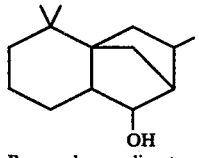<br>Prepared according to Example XII(A). | A dry woody, amber-like, castoreum-like, cedrus atlantica, and patchouli aroma. |
| 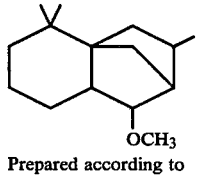<br>Prepared according to Example XII(B). | A sweet, woody, patchouli-like labdanum and green aroma. |
| 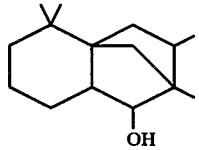<br>Prepared according to Example XIII(A). | A woody, amber, cedar aroma with green and fruity undertones. |
| 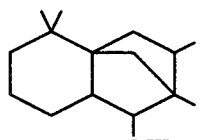<br>Prepared according to Example XIII(B). | A woody, amber, cigar-box-like, sandalwood-like, oriental aroma. |

TABLE XV-continued

| Structure of Reaction Product | Fragrance Properties |
|---|---|
| *(structure with OH)* Prepared according to Example XIV(A). | A woody, cedarwood-like and minty aroma profile. |
| *(structure with OCH₃)* Prepared according to Example XIV(B). | A woody, patchouli aroma profile. |
| *(structure with OH)* Prepared according to Example XV(A). | A dry woody, spicy, minty, floral (rose) aroma. |
| *(structure with O-C(=O)-)* Prepared according to Example XV(B). | A dry woody, camphoraceous, sweaty, vetiver-like, and grapefruit oil-like aroma. |
| *(structure with OCH₃)* Prepared according to Example XV(C). | An amber, woody, camphoraceous, fruity and sweet aroma profile. |
| *(structure with OH)* Prepared according to Example XVI. | A woody, oily, slightly amber aroma profile. |

EXAMPLE XXXI

One gram of n-tridecyl dimethyl amine oxide is admixed with eight drops of one of the substances as set forth in Table XVI below. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table XVI below; whereas without the use of one of the substances of Table XVI below, the bleached laundry has a faint characteristic disagreeable "hypochlorite" aroma.

TABLE XVI

| Structure of Reaction Product | Fragrance Properties |
|---|---|
| *(structure with OH)* Prepared according to Example XI(A). | A dry woody, thymol-like and camphoraceous-like fragrance with long lasting patchouli undertones. |
| *(structure with O-C(=O)-)* Prepared according to Example XI(B). | A dry woody (cedary, vetiver), amber-like and sandalwood-like aroma. |
| *(structure with OCH₃)* Prepared according to Example XI(C). | A fresh camphoraceous, woody, sweaty and fruity aroma. |
| *(structure with OH)* Prepared according to Example XII(A). | A dry woody, amber-like, castoreum-like, cedrus atlantica, and patchouli aroma. |
| *(structure with OCH₃)* Prepared according to Example XII(B). | A sweet, woody, patchouli-like labdanum and green aroma. |
| *(structure with OH)* Prepared according to Example XIII(A). | A woody, amber, cedar aroma with green and fruity undertones. |

TABLE XVI-continued

| Structure of Reaction Product | Fragrance Properties |
|---|---|
| [structure with OCH₃] Prepared according to Example XIII(B). | A woody, amber, cigar-box-like, sandalwood-like, oriental aroma. |
| [structure with OH] Prepared according to Example XIV(A). | A woody, cedarwood-like and minty aroma profile. |
| [structure with OCH₃] Prepared according to Example XIV(B). | A woody, patchouli aroma profile. |
| [structure with OH] Prepared according to Example XV(A). | A dry woody, spicy, minty, floral (rose) aroma. |
| [structure with OC(=O)] Prepared according to Example XV(B). | A dry woody, camphoraceous, sweaty, vetiver-like, and grapefruit oil-like aroma. |
| [structure with OCH₃] Prepared according to Example XV(C). | An amber, woody, camphoraceous, fruity and sweet aroma profile. |
| [structure with OH] Prepared according to Example XVI. | A woody, oily, slightly amber aroma profile. |

EXAMPLE XXXII

A "soft-feel, good-hold" hair spray is produced containing the following ingredients:

| Ingredients | Parts by Weight |
|---|---|
| Polyvinylpyrrilidones/Vinyl acetate "E-735 Copolymer manufactured by the GAF corporation of New York, N.Y. | 4.0 |
| Anhydrous Ethanol | 70.90 |
| Dioctyl Sebecate | 0.05 |
| Benzyl Alcohol | 0.05 |
| "Propellant A46" manufactured by the GAF corporation of New York, N.Y. | 24.95 |
| Fragrance ingredient as set forth in Table XVII below | 0.05 |

The PVP/VA copolymers are first dissolved in alcohol and all other ingredients are added until uniform. The propellant is then pressurized and used as an aerosol. The resulting hair-spray has a pleasant aroma as set forth in Table XVII below:

TABLE XVII

| Structure of Reaction Product | Fragrance Properties |
|---|---|
| [structure with OH] Prepared according to Example XI(A). | A dry woody, thymol-like and camphoraceous-like fragrance with long lasting patchouli undertones. |
| [structure with OC(=O)] Prepared according to Example XI(B). | A dry woody (cedary, vetiver), amber-like and sandalwood-like aroma. |
| [structure with OCH₃] Prepared according to Example XI(C). | A fresh camphoraceous, woody, sweaty and fruity aroma. |
| [structure with OH] Prepared according to Example XII(A). | A dry woody, amber-like, castoreum-like, cedrus atlantica, and patchouli aroma. |

TABLE XVII-continued

| Structure of Reaction Product | Fragrance Properties |
|---|---|
| [structure with OCH3] Prepared according to Example XII(B). | A sweet, woody, patchouli-like labdanum and green aroma. |
| [structure with OH] Prepared according to Example XIII(A). | A woody, amber, cedar aroma with green and fruity undertones. |
| [structure with OCH3] Prepared according to Example XIII(B). | A woody, amber, cigar-box-like, sandalwood-like, oriental aroma. |
| [structure with OH] Prepared according to Example XIV(A). | A woody, cedarwood-like and minty aroma profile. |
| [structure with OCH3] Prepared according to Example XIV(B). | A woody, patchouli aroma profile. |
| [structure with OH] Prepared according to Example XV(A). | A dry woody, spicy, minty, floral (rose) aroma. |
| [structure with OC(O)—] Prepared according to Example XV(B). | A dry woody, camphoraceous, sweaty, vetiver-like, and grapefruit oil-like aroma. |
| [structure with OCH3] Prepared according to Example XV(C). | An amber, woody, camphoraceous, fruity and sweet aroma profile. |
| [structure with OH] Prepared according to Example XVI. | A woody, oily, slightly amber aroma profile. |

EXAMPLE XXXIII

SCOURING CLEANSER COMPOSITION

A scouring cleanser composition is prepared in accordance with Example I, at columns 11 and 12 of U.S. Pat. No. 4,193,888, issued on Mar. 18, 1980. To this composition, a substance as set forth in Table XVIII below is added at the level of 0.250% as set forth in the Table in said Example I of U.S. Pat. No. 4,193,888 yielding an aroma on using said cleanser in ordinary circumstances which is quite pleasant and described in said Table XVIII as set forth below:

TABLE XVIII

| Structure of Reaction Product | Fragrance Properties |
|---|---|
| [structure with OH] Prepared according to Example XI(A). | A dry woody, thymol-like and camphoraceous-like fragrance with long lasting patchouli undertones. |
| [structure with OC(O)—] Prepared according to Example XI(B). | A dry woody (cedary, vetiver), amber-like and sandalwood-like aroma. |
| [structure with OCH3] Prepared according to Example XI(C). | A fresh camphoraceous, woody, sweaty and fruity aroma. |

TABLE XVIII-continued

| Structure of Reaction Product | Fragrance Properties |
|---|---|
| [structure with OH] Prepared according to Example XII(A). | A dry woody, amber-like, castoreum-like, cedrus atlantica, and patchouli aroma. |
| [structure with OCH₃] Prepared according to Example XII(B). | A sweet, woody, patchouli-like labdanum and green aroma. |
| [structure with OH] Prepared according to Example XIII(B). | A woody, amber, cedar aroma with green and fruity undertones. |
| [structure with OCH₃] Prepared according to Example XIII(B). | A woody, amber, cigar-box-like, sandalwood-like, oriental aroma. |
| [structure with OH] Prepared according to Example XIV(A). | A woody, cedarwood-like and minty aroma profile. |
| [structure with OCH₃] Prepared according to Example XIV(B). | A woody, patchouli aroma profile. |
| [structure with OH] Prepared according to Example XV(A). | A dry woody, spicy, minty, floral (rose) aroma. |
| [structure with O-acetate] Prepared according to Example XV(B). | A dry woody, camphoraceous, sweaty, vetiver-like, and grapefruit oil-like aroma. |
| [structure with OCH₃] Prepared according to Example XV(C). | An amber, woody, camphoraceous, fruity and sweet aroma profile. |
| [structure with OH] Prepared according to Example XVI. | A woody, oily, slightly amber aroma profile. |

EXAMPLE XXXIV

A fabric softening article prepared substantially as set forth in Example VIII of Canadian Pat. No. 1,069,260 is prepared, containing 0.21 percent by weight of a perfuming substance as set forth in Table XIX below and yielding on use in a dryer, a faint aroma as set forth in Table XIX below:

TABLE XIX

| Structure of Reaction Product | Fragrance Properties |
|---|---|
| [structure with OH] Prepared according to Example XI(A). | A dry woody, thymol-like and camphoraceous-like fragrance with long lasting patchouli undertones. |
| [structure with O-acetate] Prepared according to | A dry woody (cedary, vetiver), amber-like and sandalwood-like aroma. |

TABLE XIX-continued

| Structure of Reaction Product | Fragrance Properties |
|---|---|
| Example XI(B). [structure with OCH₃] Prepared according to Example XI(C). | A fresh camphoraceous, woody, sweaty and fruity aroma. |
| [structure with OH] Prepared according to Example XII(A). | A dry woody, amber-like, castoreum-like, cedrus atlantica, and patchouli aroma. |
| [structure with OCH₃] Prepared according to Example XII(B). | A sweet, woody, patchouli-like labdanum and green aroma. |
| [structure with OH] | A woody, amber, cedar aroma with green and fruity undertones. |
| [structure with OCH₃] Prepared according to Example XIII(B). | A woody, amber, cigar-box-like, sandalwood-like, oriental aroma. |
| [structure with OH] Prepared according to Example XIV(A). | A woody, cedarwood-like and minty aroma profile. |
| [structure with OCH₃] | A woody, patchouli aroma profile. |
| Prepared according to Example XIV(B). [structure with OH] | A dry woody, spicy, minty, floral (rose) aroma. |
| Prepared according to Example XV(A). [structure with O-C(=O)- acetate] | A dry woody, camphoraceous, sweaty, vetiver-like, and grapefruit oil-like aroma. |
| Prepared according to Example XV(B). [structure with OCH₃] | An amber, woody, camphoraceous, fruity and sweet aroma profile. |
| Prepared according to Example XV(C). [structure with OH] Prepared according to Example XVI. | A woody, oily, slightly amber aroma profile. |

EXAMPLE XXXV A-F

The tricyclic alcohols, esters and ethers produced according to Examples XI(A)-XIII(A) have very long lasting, dry woody (cedary, vetiver), thymol-like, camphoraceous, amber, sandalwood-like, fresh, sweaty, fruity, castoreum-like, cedrus atlantica, patchouli-like, labdanum-like, green, fruity, woody, amber, cigar box-like, sandalwood-like, oriental, cedarwood-like, minty, spicy, floral (rose), aromas which are warm and rich on dryout. These aromas may be used to a great extent in inexpensive functional products. The following pine fragrance demonstrates the use of these materials in perfume compositions. In each of the cases, the tricyclic alcohols, esters and ethers of our invention are used in an amount of 47.9%:

| | Parts by Weight Example | | | | | |
|---|---|---|---|---|---|---|
| Ingredients | XXXVA | XXXVB | XXXVC | XXXVD | XXXVE | XXXVF |
| Isobornyl acetate | 100 | 100 | 100 | 100 | 100 | 100 |
| Camphor | 10 | 10 | 10 | 10 | 10 | 10 |
| Terpineol | 25 | 25 | 25 | 25 | 25 | 25 |
| Fir Balsam Absolute (50% in Diethyl Phthalate) | 20 | 20 | 20 | 20 | 20 | 20 |
| Coumarin | 4 | 4 | 4 | 4 | 4 | 4 |
| Linalool | 30 | 30 | 30 | 30 | 30 | 30 |
| Anethol | 2 | 2 | 2 | 2 | 2 | 2 |
| Fenchyl Alcohol | 10 | 10 | 10 | 10 | 10 | 10 |
| Lemon Terpenes Washed | 50 | 50 | 50 | 50 | 50 | 50 |
| Borneol | 5 | 5 | 5 | 5 | 5 | 5 |
| Galbanum Oil | 5 | 5 | 5 | 5 | 5 | 5 |
| Turpentine Russian | 150 | 150 | 150 | 150 | 150 | 150 |
| Pinus Pumilionus | 50 | 50 | 50 | 50 | 50 | 50 |
| Eucalyptol | 50 | 50 | 50 | 50 | 50 | 50 |
| 2,2,6-trimethyl-1-cyclohexene-1-carboxaldehyde | 5 | 5 | 5 | 5 | 5 | 5 |
| Maltol 1% in Diethyl Phthalate | 5 | 5 | 5 | 5 | 5 | 5 |
| Product produced according to Example XI(A) having the structure: | 479 | 0 | 0 | 0 | 0 | 0 |

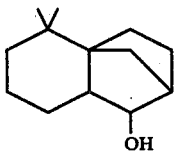

| | | | | | | |
|---|---|---|---|---|---|---|
| Product produced according to Example XI(B) having the structure: | 0 | 479 | 0 | 0 | 0 | 0 |

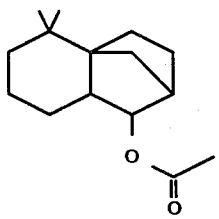

| | | | | | | |
|---|---|---|---|---|---|---|
| Product produced according to Example XI(C) having the structure: | 0 | 0 | 479 | 0 | 0 | 0 |

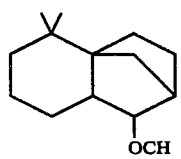

OCH

| | | | | | | |
|---|---|---|---|---|---|---|
| Product produced according to Example XII(A) having the structure: | 0 | 0 | 0 | 479 | 0 | 0 |

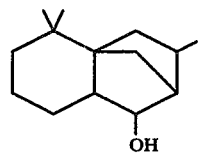

| | | | | | | |
|---|---|---|---|---|---|---|
| Product produced according to Example XII(B) having the structure: | 0 | 0 | 0 | 0 | 479 | 0 |

-continued

| | Parts by Weight Example | | | | | |
|---|---|---|---|---|---|---|
| Ingredients | XXXVA | XXXVB | XXXVC | XXXVD | XXXVE | XXXVF |
| 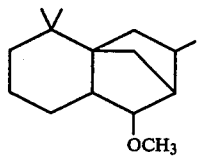 Product produced according to Example XIII(A) having the structure: | 0 | 0 | 0 | 0 | 0 | 479 |
| 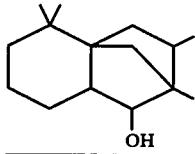 | | | | | | |

EXAMPLE XXXV G-N

The tricyclic alcohols, esters and ethers produced according to Examples XIII(B)–XVI have very long lasting, dry woody, (cedary, vetiver), thymol-like, camphoraceous, amber, sandalwood-like, fresh, sweaty, fruity, castoreum-like, cedrus atlantica, patchouli-like, labdanum-like, green, fruity, woody, amber, cigar box-like, sandalwood-like, oriental, cedarwood-like, minty, spicy, floral (rose), aromas which are warm and rich on dryout. These aromas may be used to a great extent in inexpensive functional products. The following pine fragrance demonstrates the use of these materials in perfume compositions. In each of the cases, the tricyclic alcohols, esters and ethers of our invention are used in an amount of 47.9%:

| | Parts by Weight Example | | | | | | |
|---|---|---|---|---|---|---|---|
| Ingredients | XXXVG | XXXVH | XXXVJ | XXXVK | XXXVL | XXXVM | XXXVN |
| Isobornyl acetate | 100 | 100 | 100 | 100 | 100 | 100 | 100 |
| Camphor | 10 | 10 | 10 | 10 | 10 | 10 | 10 |
| Terpineol | 25 | 25 | 25 | 25 | 25 | 25 | 25 |
| Fir Balsam Absolute (50% in Diethyl Phthalate) | 20 | 20 | 20 | 20 | 20 | 20 | 20 |
| Coumarin | 4 | 4 | 4 | 4 | 4 | 4 | 4 |
| Linalool | 30 | 30 | 30 | 30 | 30 | 30 | 30 |
| Anethol | 2 | 2 | 2 | 2 | 2 | 2 | 2 |
| Fenchyl Alcohol | 10 | 10 | 10 | 10 | 10 | 10 | 10 |
| Lemon Terpenes Washed | 50 | 50 | 50 | 50 | 50 | 50 | 50 |
| Borneol | 5 | 5 | 5 | 5 | 5 | 5 | 5 |
| Galbanum Oil | 5 | 5 | 5 | 5 | 5 | 5 | 5 |
| Turpentine Russian | 150 | 150 | 150 | 150 | 150 | 150 | 150 |
| Pinus Pumilionus | 50 | 50 | 50 | 50 | 50 | 50 | 50 |
| Eucalyptol | 50 | 50 | 50 | 50 | 50 | 50 | 50 |
| 2,2,6-trimethyl-1-cyclo-hexene-1-carboxaldehyde | 5 | 5 | 5 | 5 | 5 | 5 | 5 |
| Maltol 1% in Diethyl Phthalate | 5 | 5 | 5 | 5 | 5 | 5 | 5 |
| Product produced according to Example XIII(B) having the structure: | 479 | 0 | 0 | 0 | 0 | 0 | 0 |
| 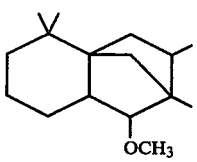 Product produced according to Example XIV(A) having the structure: | 0 | 479 | 0 | 0 | 0 | 0 | 0 |

|                                                                  | Parts by Weight Example | | | | | | |
|---|---|---|---|---|---|---|---|
| Ingredients | XXXVG | XXXVH | XXXVJ | XXXVK | XXXVL | XXXVM | XXXVN |
| 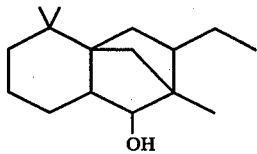 Product produced according to Example XIV(B) having the structure: | 0 | 0 | 479 | 0 | 0 | 0 | 0 |
| 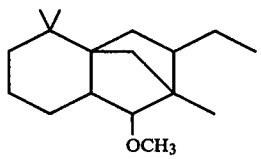 Product produced according to Example XV(A) having the structure: | 0 | 0 | 0 | 479 | 0 | 0 | 0 |
| 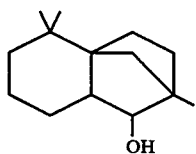 Product produced according to Example XV(B) having the structure: | 0 | 0 | 0 | 0 | 479 | 0 | 0 |
| 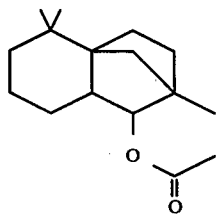 Product produced according to Example XV(C) having the structure: | 0 | 0 | 0 | 0 | 0 | 479 | 0 |
| 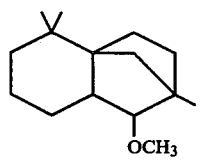 Product produced according to Example XVI having the structure: | 0 | 0 | 0 | 0 | 0 | 0 | 479 |

|            | Parts by Weight Example | | | | | | |
|---|---|---|---|---|---|---|---|
| Ingredients | XXXVG | XXXVH | XXXVJ | XXXVK | XXXVL | XXXVM | XXXVN |

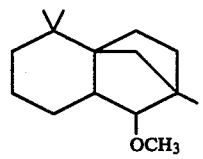

The presence of the various tricyclic alcohols, esters and ethers of our invention, supports various notes as indicated below, and produces a considerable savings in the cost of the formulations.

| Example | Additional Nuances Added to the Piney, Herbaceous Aroma of the Fragrance |
|---|---|
| XI(A) | A dry woody, thymol-like and camphoraceous-like fragrance with long lasting patchouli undertones. |
| XI(B) | A dry woody (cedary, vetiver) amber-like and sandalwood-like aroma. |
| XI(C) | A fresh camphoraceous, woody, sweaty and fruity aroma. |
| XII(A) | A dry woody, amber-like, castoreum-like, cedrus atlantica, and patchouli aroma. |
| XII(B) | A sweet, woody, patchouli-like labdanum and green aroma. |
| XIII(A) | A woody, amber, cedar aroma with green and fruity undertones. |
| XIII(B) | A woody, amber, cigar box-like, sandalwood-like, oriental aroma. |
| XIV(A) | A woody, cedarwood-like and minty aroma profile. |
| XIV(B) | A woody, patchouli aroma profile |
| XV(A) | A dry woody, spicy, minty, floral (rose) aroma becoming warm and rich on dryout. |
| XV(B) | A dry woody, camphoraceous, sweaty, vetiver-like and grapefruit oil-like aroma. |
| XV(C) | An amber, woody, camphoraceous, fruity and sweet aroma profile. |
| XVI | A woody, oily, slightly amber aroma profile. |

EXAMPLE XXXVI

WALNUT FLAVOR COMPOSITION

The following basic walnut flavor formulation is prepared:

| Ingredients | Parts by Weight |
|---|---|
| Ethyl-2-methyl butyrate | 10 |
| Vanillin | 40 |
| Butyl valerate | 40 |
| 2,3-Diethyl pyrazine | 5 |
| Methyl cyclopentenolone | 80 |
| Benzaldehyde | 60 |
| Valerin oil Indian | 0.5 |

| Ingredients | Parts by Weight |
|---|---|
| (1% in 95% aqueous ethanol alcohol) Propylene Glycol | 764.5 |

The compound having the structure:

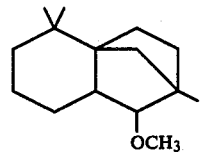

produced according to Example XV(C) is added to the above formulation at the rate of 1.5%. This formulation is compared to a formulation which does not have the compound having the structure:

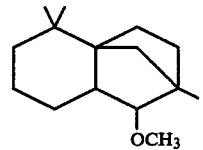

added to it at the rate of 20 ppm in water. The formulation containing the compound having the structure:

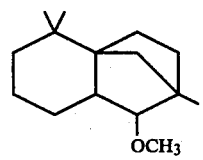

has a "woody-balsamic" fresh walnut kernel and walnut skin-like taste and, in addition, has a fuller mouth feel and longer lasting taste. The flavor that has added to it the compound having the structure:

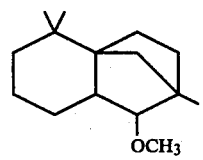

is preferred by a group of flavor panelists and they consider it to be a substantially improved walnut flavor.

EXAMPLE XXXVII

BEVERAGE

The addition of the compound having the structure:

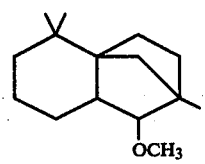

prepared by the process of Example XV(C) at the rate of 0.3 ppm to a commercial cola beverage gives the beverage a fuller "woody-balsamic" long lasting taste and adds to the pleasant top notes of the beverage. When comparing the cola beverage containing the compound having the structure:

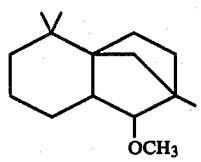

to one having the same formula but not containing the compound having the structure:

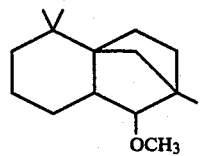

a 5 member bench panel prefers the beverage containing the compound having the structure:

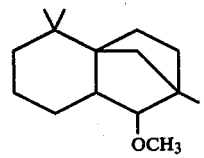

EXAMPLE XXXVIII

TOBACCO FLAVOR FORMULATION

Cigarettes are produced using the following tobacco formulation:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| H$_2$O | 5.3 |

At the rate of 0.2%, the following tobacco flavor formulation is applied to all of the cigarettes produced with the above tobacco formulation.

| Ingredients | Parts by Weight |
|---|---|
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| H$_2$O | 41.90 |

To 50% of the cigarettes, 10 and 20 ppm of one of the compounds set forth in Table XX are added. These cigarettes are hereinafter called "experimental" cigarettes and the cigarettes without the tricyclic alcohols, ethers or acetates in the following table are hereinafter called "control" cigarettes. The control and experimental cigarettes are then evaluated by paired comparison and the results are as set forth in Table XX below.

All cigarettes both control and experimental are evaluated for smoke flavor with 20 mm cellulose acetate filters.

TABLE XX

| Structure of Reaction Product | Smoking Tobacco Flavor Evaluation |
|---|---|
| Prepared according to Example XI(A). | Patchouli-like flavor and aroma both prior to and on smoking. |
| Prepared according to Example XI(B). | An oriental/incense aroma and taste prior to and on smoking causing the Virginia tobacco to have "Turkish tobacco" nuances on smoking. |
| Prepared according to Example XI(C). | An oriental aroma and taste prior to and on smoking in the main stream and the side stream causing the Virginia-like tobaccos to be more "Turkish-like". |
| Prepared according to Example XII(B). | Oriental aroma and taste both prior to and on smoking in the main stream and the side stream causing Virginia-like tobacco to be more "Turkish-like". |

TABLE XX-continued

| Structure of Reaction Product | Smoking Tobacco Flavor Evaluation |
|---|---|
| (structure with OCH₃)<br>Prepared according to Example XIII(B). | An oriental aroma and taste both prior to and on smoking in the main stream and the side stream causing Virginia-like tobaccos to be more "Turkish-like". |
| (structure with OCH₃)<br>Prepared according to Example XIV(B). | An oriental aroma and taste both prior to and on smoking in the main stream and in the side stream causing the Virginia-like tobaccos to be more "Turkish-like". |
| (structure with OH)<br>Prepared according to Example XV(A). | An oriental aroma and taste with interesting menthol-like and cooling undertones in both the main stream and the side stream on smoking. The combination of oriental and minty aroma nuances causes smoking tobacco to be "Turkish-like" and at the same time have pleasant cooling nuances. |
| (structure with O-acetyl)<br>Prepared according to Example XV(B). | A woody, oriental aroma and taste both prior to and on smoking in the main stream and in the side stream. |
| (structure with OCH₃)<br>Prepared according to Example XV(C). | A natural tobacco-like oriental, cedarwood-like and woody aroma and taste both prior to and on smoking in the main stream and in the side stream. |

What is claimed is:

1. A process for augmenting or enchancing the aroma of a perfume composition or cologne comprising the step of adding to a perfume base or a cologne base an aroma augmenting or enhancing quantity of at least one tricyclic compound having the structure:

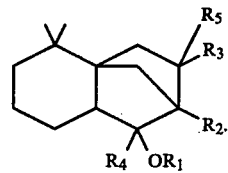

wherein $R_1$ represents hydrogen, methyl or acetyl and wherein $R_2$, $R_3$, $R_4$ and $R_5$ may be the same or different and each is hydrogen, methyl or ethyl.

2. The process of claim 1 wherein the tricyclic compound has the structure:

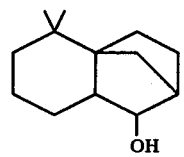

3. The process of claim 1 wherein the tricyclic compound has the structure:

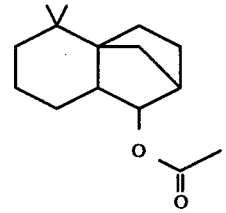

4. The process of claim 1 wherein the tricyclic compound has the structure:

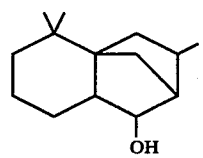

5. The process of claim 1 wherein the tricyclic compound has the structure:

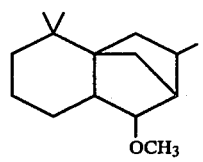

6. The process of claim 1 wherein the tricyclic compound has the structure:

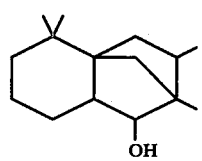

7. The process of claim 1 wherein the tricyclic compound has the structure:

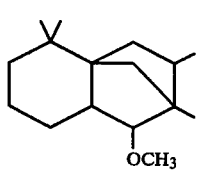

8. The process of claim 1 wherein the tricyclic compound has the structure:

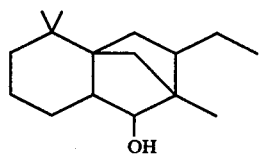

9. The process of claim 1 wherein the tricyclic compound has the structure:

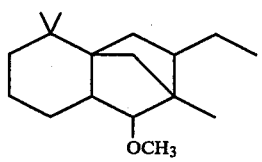

10. The process of claim 1 wherein the tricyclic compound has the structure:

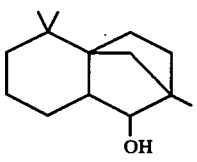

11. The process of claim 1 wherein the tricyclic compound has the structure:

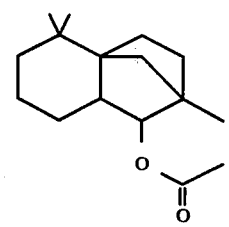

12. The process of claim 1 wherein the tricyclic compound has the structure:

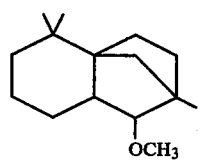

13. The process of claim 1 wherein the tricyclic compound has the structure:

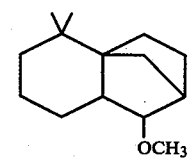

14. The process of claim 1 wherein the tricyclic compound has the structure:

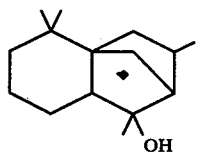

* * * * *